(12) United States Patent
Wiederkehr et al.

(10) Patent No.: US 8,951,746 B2
(45) Date of Patent: Feb. 10, 2015

(54) METHOD AND DEVICES FOR SCREENING CERVICAL CANCER

(75) Inventors: Urs G. Wiederkehr, Foster City, CA (US); Jian Ling, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 1756 days.

(21) Appl. No.: 11/718,695

(22) PCT Filed: Nov. 4, 2005

(86) PCT No.: PCT/US2005/040165
§ 371 (c)(1),
(2), (4) Date: Mar. 24, 2008

(87) PCT Pub. No.: WO2006/052822
PCT Pub. Date: May 18, 2006

(65) Prior Publication Data
US 2008/0262384 A1    Oct. 23, 2008

Related U.S. Application Data

(60) Provisional application No. 60/625,369, filed on Nov. 5, 2004.

(51) Int. Cl.
  *G01N 33/543* (2006.01)
  *G01N 33/574* (2006.01)

(52) U.S. Cl.
  CPC ............................. *G01N 33/57411* (2013.01)
  USPC .............. 435/7.23; 435/7.2; 435/40.5; 436/8; 436/63; 436/64; 436/164; 436/171; 422/406; 422/82.08

(58) Field of Classification Search
  USPC ......... 435/7.2, 7.23, 40.5; 436/8, 63, 64, 164, 436/171; 422/406, 82.08
  See application file for complete search history.

(56) References Cited

U.S. PATENT DOCUMENTS

| | | | |
|---|---|---|---|
| 4,852,579 A | | 8/1989 | Gilstad et al. |
| 5,089,416 A * | | 2/1992 | Schwartz et al. .................. 436/8 |
| 6,352,513 B1 | | 3/2002 | Anderson et al. |
| 6,405,070 B1 * | | 6/2002 | Banerjee ........................ 600/407 |
| 6,540,981 B2 * | | 4/2003 | Klaveness et al. .............. 424/9.6 |
| 6,692,702 B1 * | | 2/2004 | Burshteyn et al. .............. 422/101 |
| 2001/0023078 A1 * | | 9/2001 | Bawendi et al. .............. 436/524 |
| 2002/0057991 A1 * | | 5/2002 | Kelly et al. ...................... 422/56 |
| 2002/0106685 A1 | | 8/2002 | Henning et al. |
| 2003/0219726 A1 * | | 11/2003 | Doorbar ............................. 435/5 |
| 2004/0002125 A1 * | | 1/2004 | Gombrich et al. ........... 435/7.23 |
| 2004/0038320 A1 * | | 2/2004 | Banerjee ...................... 435/7.23 |
| 2004/0234623 A1 * | | 11/2004 | Munn et al. ..................... 424/649 |
| 2005/0048467 A1 * | | 3/2005 | Sastry et al. ....................... 435/5 |
| 2005/0207940 A1 * | | 9/2005 | Butler et al. ..................... 422/73 |

FOREIGN PATENT DOCUMENTS

WO    02 079752 A2   10/2002
WO    2004 038418 A1   5/2004

OTHER PUBLICATIONS

Corsetti et al. Correction of Cellular Autofluorescence in Flow Cytometry by Mathematical Modeling of Cellular Fluorescence, Cytometry 9: 539-547 (1988).*
Bibbo, et al., "p16INK4A as an Adjunct Test in Liquid-Based Cytology," Analytical and Quantitative Cytology and Histology, vol. 25, No. 1, Feb. 2003. pp. 8-11.
Bibbo, et al., "Procedure for Immunocytochemical Detection of p16INK4A Antigen in Thin-Layer, Liquid-Based Specimens," Acta Cytologica, vol. 46, No. 1, Feb. 2002. (5 pages).
Drezek, "Light scattering from cervical cells throughout neoplastic progression: influence of nuclear morphology, DNA content, and chromatin texture," Journal of Biomedical Optics 8(1), 7-16 (Jan. 2003) (10 pages).
Freeman, "Minichromosome Maintenance Proteins as Biological Markers of Dysplasia and Malignancy," Clinical Cancer Research vol. 5, 2121-2132, Aug. 1999, pp. 2121-2132.
Georgakoudi, et al., "NAD(P)H and Collagen as in Vivo Quantitative Fluorescent Biomarkers of Epithelial Precancerous Changes," Cancer Research 62,682-687, Feb. 1, 2002, pp. 682-687.
Hu, et al., "The P1 family: a new class of nuclear mammalian proteins related to the yeast Mcm replication proteins," Nucleic Acids Research, 1993, vol. 21, No. 23, pp. 5289-5293.
Pavlova, "Microanatomical and Biochemical Origins of Normal and Precancerous Cervical Autofluorescence Using Laser-scanning Fluorescence Confocal Microscopy," Photochemistry and Photobiology, 2003, 77(5): 550-555.
Saqi, et al., "Overexpression of p16INK4A in Liquid Based Specimens (SurePath™) as Marker of Cervical Dysplasia and Neoplasia," Diagnostic Cytopathology, vol. 27, No. 6, pp. 365-370.
Williams, et al., "A human protein related to yeast Cdc6p," Proc. Natl. Acad. Sci. USA vol. 94, pp. 142-147, Jan. 1997, Biochemistry.
Williams, et al., "Improved cervical smear assessment using antibodies against proteins that regulate DNA replication," Proc. Natl. Acad. Sci. USA, vol. 95, pp. 14932-14937, Dec. 1998, Medical Sciences.

* cited by examiner

*Primary Examiner* — Gail R Gabel

(74) *Attorney, Agent, or Firm* — Grossman, Tucker et al

(57) ABSTRACT

The present invention provides multi-parameter analysis methods for determining the presence or absence of precancerous or cancerous cells in a cervical sample and for screening cervical abnormality in a cervical sample. The invention also provides an apparatus and automated methods for screening cervical abnormality in a sample. The invention further provides a sampling device and a sample collection assembly for collecting cell samples, including cervical samples.

8 Claims, 27 Drawing Sheets

Figure 6.
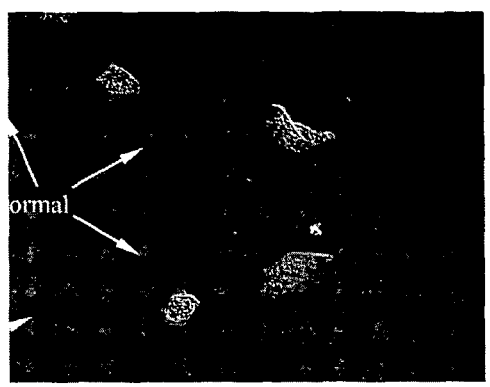
(a)
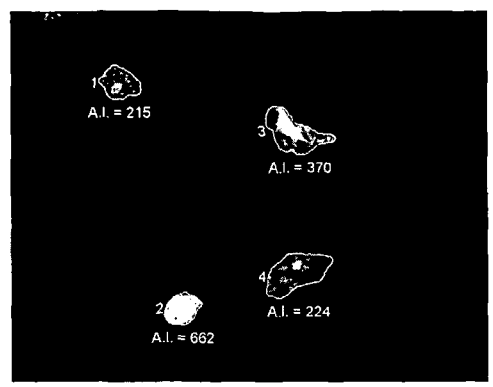
(b)
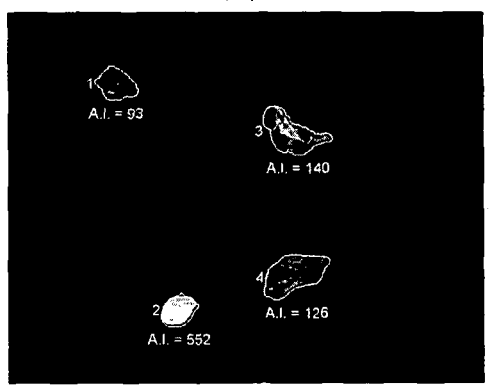
(c)
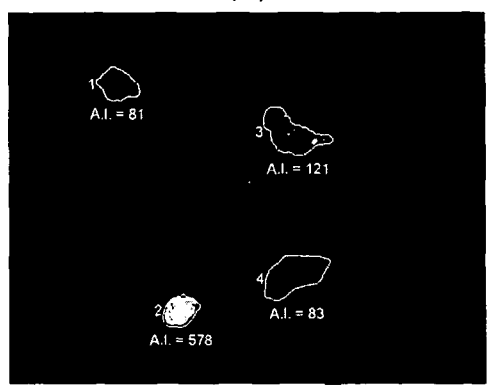
(d)

Figure 11
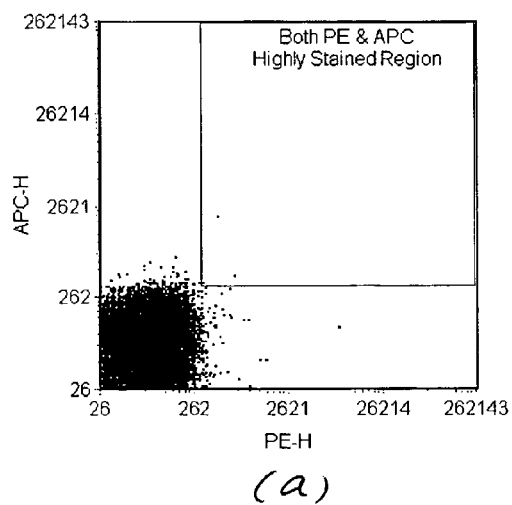
(a)
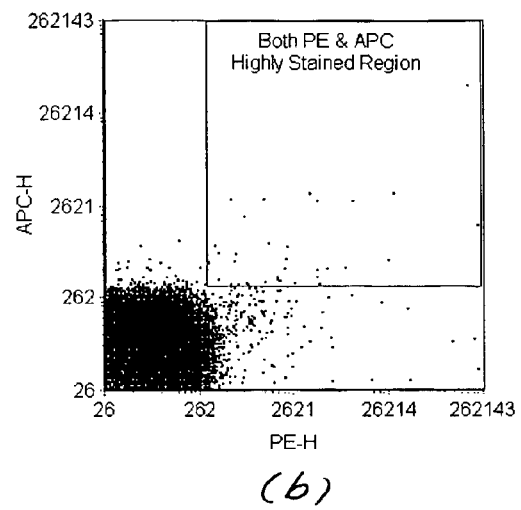
(b)

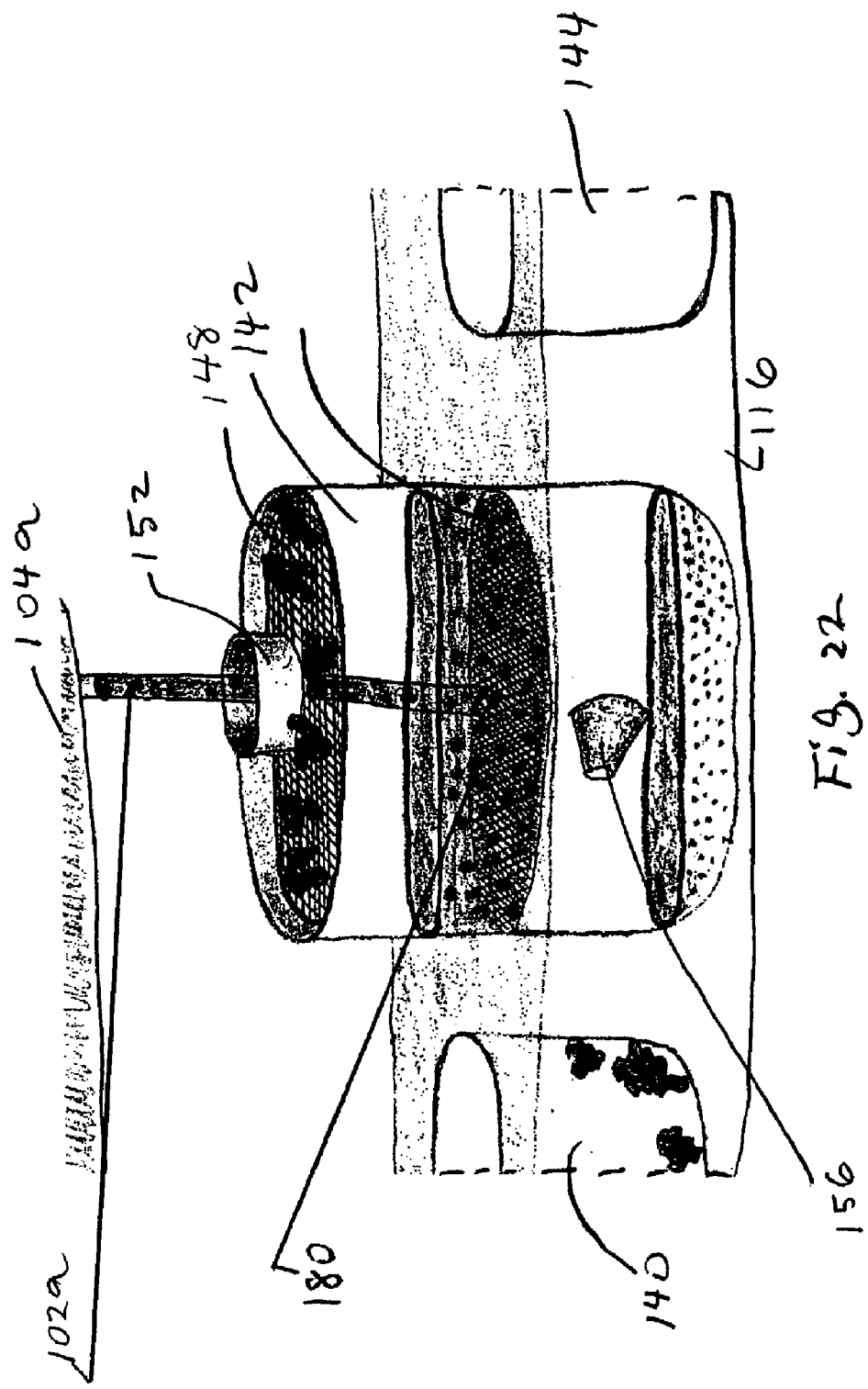

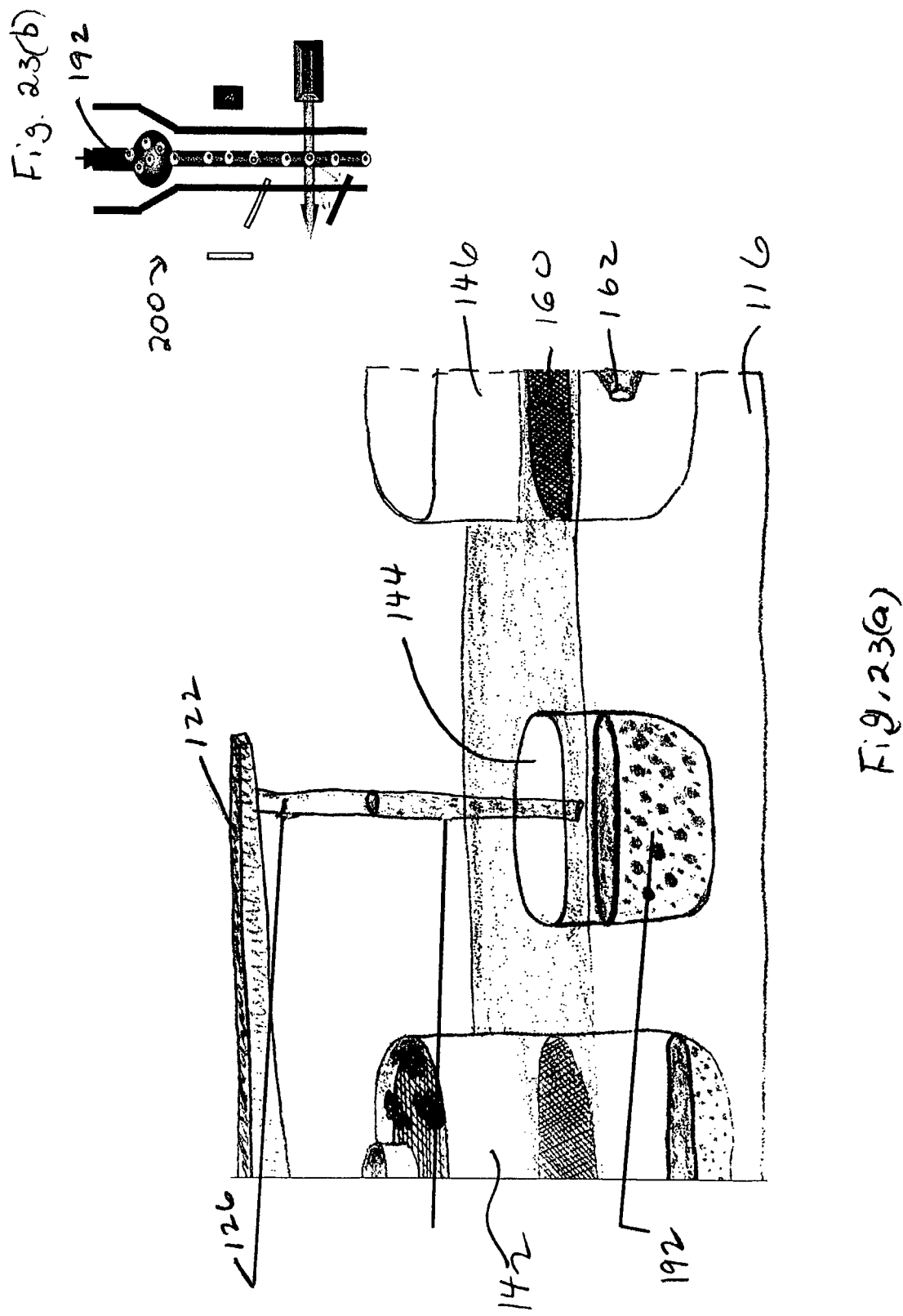

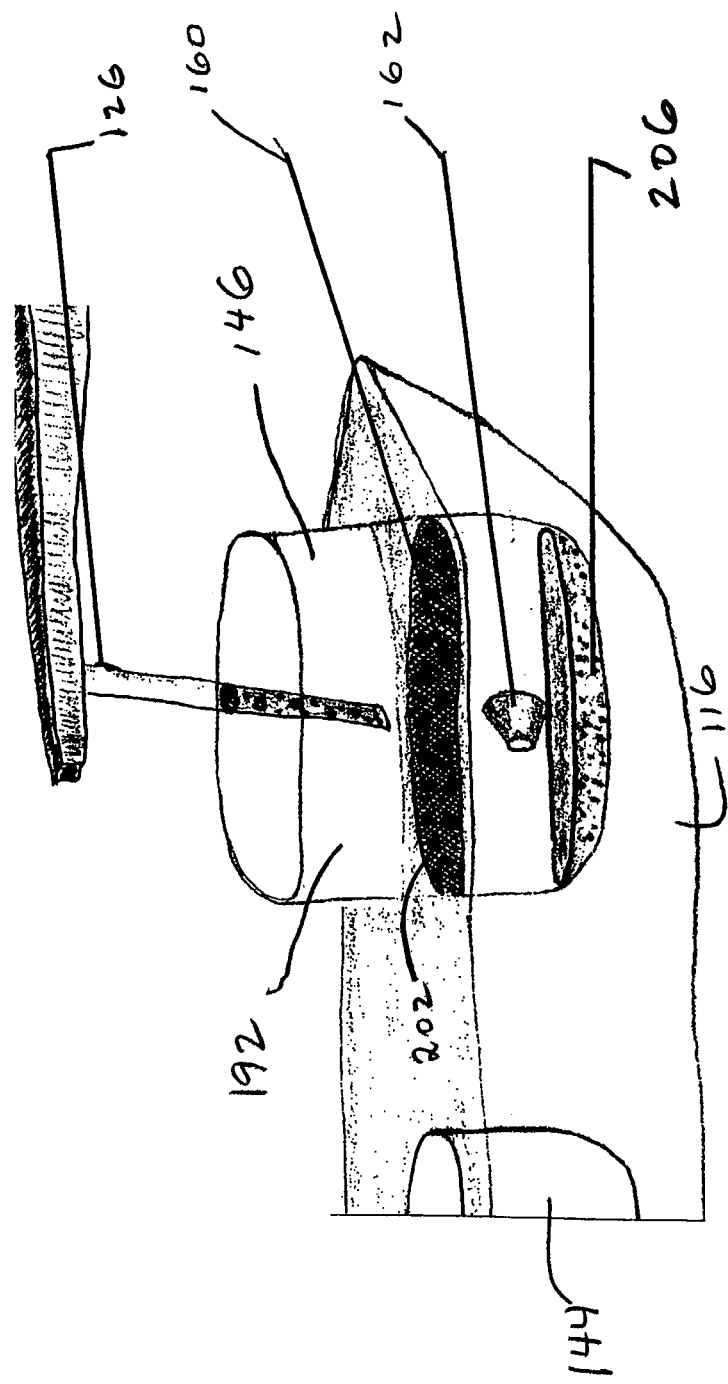

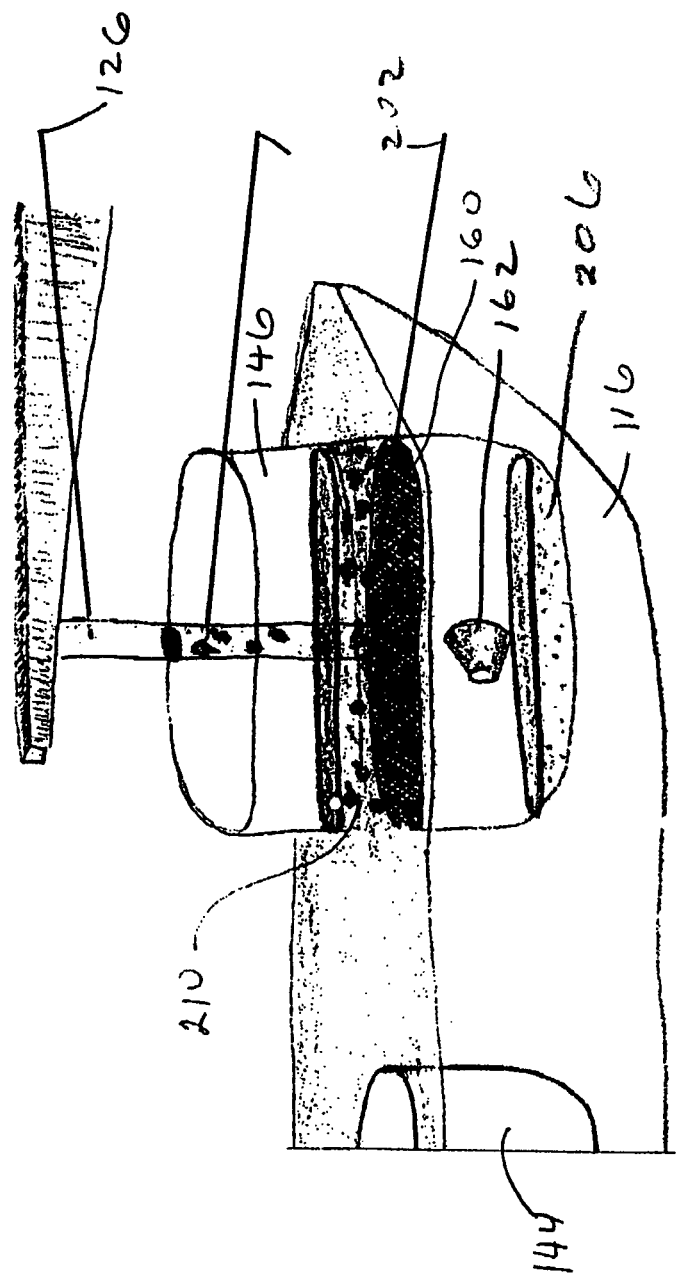

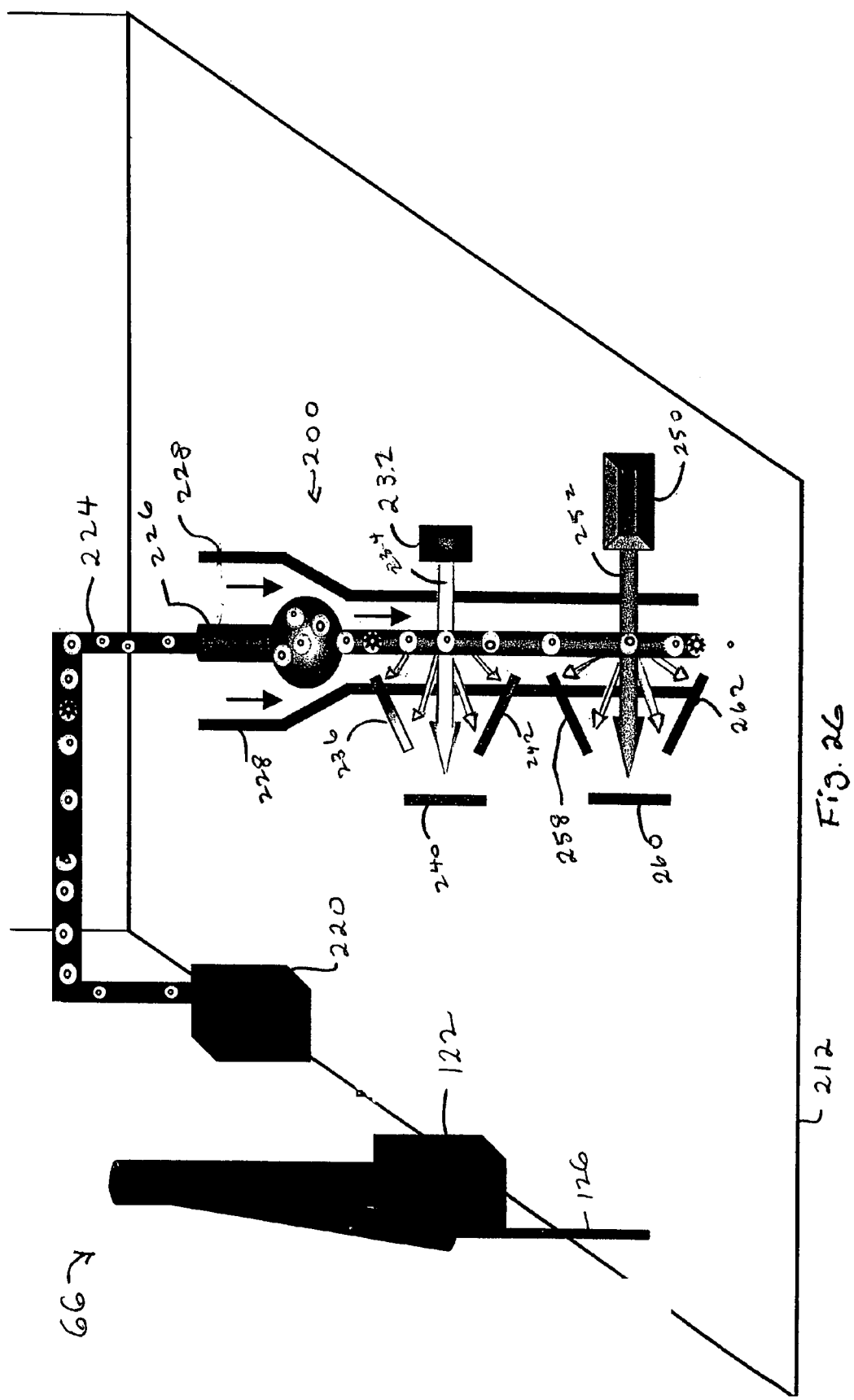

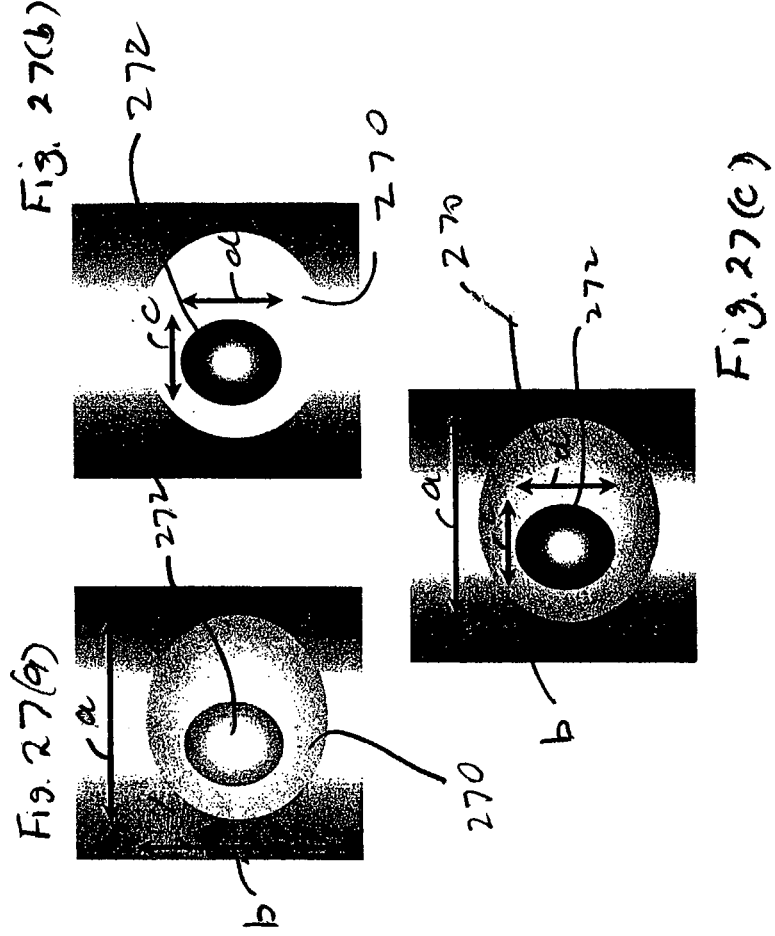

METHOD AND DEVICES FOR SCREENING CERVICAL CANCER

CROSS-REFERENCE TO RELATED APPLICATIONS

This application claims the priority benefit of U.S. Provisional Application 60/625,369, filed Nov. 5, 2004, which is hereby incorporated herein by reference in its entirety.

FIELD OF THE INVENTION

The methods and devices described herein relate generally to analyzing cellular materials such as cervical cells. In particular, the methods and devices relate to techniques and automated devices for detecting cervical abnormality.

STATEMENT REGARDING FEDERALLY SPONSORED RESEARCH OR DEVELOPMENT

Not applicable.

BACKGROUND ART

Cervical cancer is the second most common type of cancer in women worldwide, with about 500,000 new cases of cervical cancer and about 250,000 cervical cancer-related deaths reported each year. Cervical cancer develops in the epithelium layer of the cervix, and usually begins slowly with precancerous abnormalities, or cervical dysplasia. The most common (75%) cervical cancer, called squamous cell carcinoma, arises from changes in the squamous cells of the epithelium. Another 20% of the cervical cancers, called endocervical adenocarcinomas, arise from changes in cervical glandular cells. In rare cases, cancer can occur in the stroma, cells that form the supportive tissue around the cervix.

Cervical intraepithelial neoplasia (CIN) is characterized by squamous cells of the epithelium becoming abnormal in size and shape and beginning to multiply. CIN may become cancerous. Progression of CIN to cancer is characterized by the ability of the cells to actually invade into surrounding tissues. To help determine the risk of progressing into cancer, CIN is further categorized into three levels of severity. CIN I refers to mild abnormalities that rarely (1%) develop into cervical cancer. This condition may progress if untreated but is often self-limiting, usually returning to normal without treatment. CIN II refers to the lesions that often appear more aggressive under the microscope and may progress to cancer unless treated. In women with untreated CIN II, the risk for progression is 16% by two years and 25% after five years. CIN III refers to the most aggressive form of CIN, and carries the highest chance of progressing to invasive cancer if not removed. CIN III includes Carcinoma In Situ (CIS). CIS is characterized by cells that look cancerous under the microscope but have not yet invaded the surrounding tissue. Most untreated CIS will develop into invasive cancers over a period of 10 to 12 years.

Human papillomavirus (HPV) has been detected in virtually all invasive cervical cancers. It is spread mainly by sex with an infected partner and is now considered to be the primary risk factor for this disease. More than 30 genetic variants of HPV can be passed through sexual contact from one person to another. However, only high-risk HPV (HR-HPV) types (16, 18, 31, 33, 35, 39, 45, 51, 52, 56, 58, 59, 68, and 69) are associated with moderate dysplasia (CIN II) and carcinoma in situ (CIN III). HPV type 18 and HPV type 16 are particularly dangerous.

When a cervical abnormality is detected and treated in precancerous stages, cervical cancer is preventable. A cytological staining of simple cervical smears was developed by Dr. George Papanicolaou in the 1930's and named after him as the Pap Smear. In the Pap Smear method, live cells are collected by gently scraping the surface of the cervix with a sampling device, such as a plastic spatula or a cytobrush. Cells from the spatula or cytobrush are directly smeared on a slide and then fixed and stained using the Papanicolaou stain. Physicians transfer the slides to a pathology lab for microscopic viewing.

Specimens are reviewed by cytotechnologists and cytopathologists under microscope. Malignant cells can be detected based on their morphological differences from the normal cells. A system called the Bethesda system is used to categorize the malignant cells into four malignancy levels: 1) atypical squamous cells of undetermined significance (ASCUS), which are mildly abnormal cells on the surface of the cervix; 2) low-grade squamous intraepithelial lesions (LSIL), which could associate with CIN I, CIN II; or CIN III on biopsy; 3) high-grade squamous intraepithelial lesions (HSIL), which are associated with moderate and severe dysplasia and associated with CIN II or CIN III on biopsy; and 4) squamous cell carcinoma (SCC). Cells at different levels differ in cell morphology, and their nucleus to cytoplasm ratio increases as the malignancy level increases.

Liquid-based cytology (LBC) is an improvement over the conventional Pap smear. In LBC the sampling device is first rinsed in a liquid preservative solution to thin the mucous and eliminate debris that can obscure the cells. The cells are then mechanically dispersed into a liquid medium. A representative aliquot of samples is transferred to a slide to form a clear, thin monolayer using an automatic machine such as the ThinPrep (Cytyc Corp., Boxborough, Mass.). The slides are then examined the same way as described above.

The Pap smear and LBC methods are based on subjective visual readings of cell morphologies. The sensitivity of the test is relatively low, which results in a high false-negative rate. In addition, these tests require highly trained staff and adequate laboratories, which make the tests labor-intensive and expensive.

Various methods for detecting cervical abnormalities (such as cervical dysplasia) are described in WO04/038418, US2002006685, and US20040002125. There is a need for more accurate, affordable, and automated methods and devices for cervical cancer screening.

All references, publications, patents, and patent applications disclosed herein are hereby incorporated by reference in their entirety.

SUMMARY OF THE INVENTION

The present invention provides methods (including automated methods) and apparatus for analyzing cervical samples. In one aspect, the invention provides multi-parameter analysis methods for analyzing cervical cells. The methods can be useful for determining the presence or absence of one or more precancerous or cancerous cells in a sample and/or for screening for a cervical abnormality in a cervical sample. The methods can also be useful for classifying cells in a cervical sample, for example by categorizing the cells as either precancerous/cancerous or normal.

In some embodiments, the invention provides a method of determining the presence or absence of one or more precancerous or cancerous cells in a cervical sample, comprising measuring multiple parameters comprising at least two fluorescent activities and at least two types of light scattering for cells in the sample, wherein at least one of the fluorescent activities is produced by a fluorescently labeled probing agent that specifically recognizes a biomarker. Presence or absence of precancerous or cancerous cells may then be determined, as described herein.

In some embodiments, the invention provides a method of determining the presence or absence of one or more precancerous or cancerous cells, comprising a) contacting the cervical sample with at least one fluorescently labeled probing agent that specifically recognizes a biomarker; b) measuring multiple parameters comprising at least two fluorescent activities and at least two types of light scattering for cells in the sample, wherein at least one of the fluorescent activities is produced by the fluorescently labeled probing agent; and c) determining the presence or absence of precancerous or cancerous cells.

Generally, in the methods described herein, cells are stained (labeled) with at least one probing agent that specifically recognizes a biomarker. Generally, a determination of the presence or absence of precancerous or cancerous cells is carried out by analyzing the multiple parameters obtained for each cell analyzed to generate one or a set of values and comparing the value or set of values with one or a set of threshold values, wherein a value or a set of values above the threshold value(s) is indicative that the cell is precancerous or cancerous. Conversely, a value or set of values below the threshold value(s) is indicative that the cell is normal, i.e., not precancerous or cancerous. The threshold values are generally determined empirically by using pre-classified samples.

In another aspect, there is provided a method of screening a cervical abnormality in a cervical sample, comprising: a) measuring multiple parameters comprising at least two fluorescent activities and at least two types of light scattering for cells in the sample, wherein at least one of the fluorescent activities is produced by a fluorescently labeled probing agent that specifically recognizes a biomarker; and b) determining whether the cervical sample is positive or negative for a cervical abnormality.

In another aspect, the invention provides a method of screening a cervical abnormality in a cervical sample, comprising: a) contacting the sample with at least one fluorescently labeled probing agent that specifically recognize a biomarker; b) measuring multiple parameters comprising at least two fluorescent activities and at least two types of light scattering for cells in the sample, wherein at least one of the fluorescent activities is produced by the fluorescently labeled probing agent; and c) determining whether the cervical sample is positive or negative for a cervical abnormality.

In some embodiments, the determination of whether the sample is positive or negative for cervical abnormality is carried out by first quantifying precancerous or cancerous cells in the sample, and a sample is deemed positive if a certain number of precancerous or cancerous cells are present in the sample. Thus, in one embodiment, the method of screening a cervical abnormality in a cervical sample comprises: a) analyzing at least about 50,000 cells in the cervical sample stained with at least one fluorescently labeled probing agent that specifically recognizes a biomarker by measuring multiple parameters comprising at least two fluorescent activities and at least two types of light scattering, wherein at least one of the fluorescent activities is produced by the fluorescently labeled probing agent; b) determining the number of precancerous or cancerous cells in the sample, wherein the presence of about 10 or more precancerous or cancerous cells in the sample is indicative that the sample is positive for cervical abnormality.

In another aspect, there is provided an automated method for screening a cervical abnormality in a cervical sample with an automated apparatus, comprising: a) processing the sample, wherein the processing comprises contacting the sample with at least one fluorescently labeled probing agent that specifically recognizes a biomarker; b) measuring multiple parameters comprising at least two fluorescent activities and at least two types of light scattering for cells in the sample, wherein at least one of the fluorescent activities is produced by the fluorescently labeled probing agent; and c) analyzing data obtained from b), wherein the automated apparatus automatically performs a) through c).

In another aspect, there is provided an automated method for screening a cervical abnormality in a cervical sample with an automated apparatus, comprising: a) processing the sample in a pre-analytical unit of the automated apparatus, wherein the processing comprises contacting the sample with at least one fluorescently labeled probing agent that specifically recognizes a biomarker; b) transferring all or an aliquot of the processed sample to an analytical unit of the automated apparatus; c) measuring multiple parameters comprising at least two fluorescent activities and at least two types of light scattering for cells in the sample, wherein at least one of the fluorescent activities is produced by the fluorescently labeled probing agent; and d) analyzing data obtained from c), wherein the automated apparatus automatically performs a) through d).

In some embodiments, the invention provides an automated method for screening a cervical abnormality in a cervical sample with an automated apparatus, comprising: a) transferring the sample to a pre-analytical unit of the automated apparatus; b) processing the sample in a pre-analytical unit of the automated apparatus, wherein the processing comprises contacting the sample with at least one fluorescently labeled probing agent that specifically recognizes a biomarker; c) transferring all or an aliquot of the processed sample processed to an analytical unit of the automated apparatus; d) measuring for cells analyzed in the analytical unit multiple parameters comprising at least two fluorescent activities and at least two types of light scattering, wherein at least one of the fluorescent activities is produced by a fluorescently labeled probing agent that specifically recognizes a biomarker; and e) analyzing the data obtained from d), wherein the automated apparatus automatically performs a) through e).

In another aspect, the invention provides an automated method for screening a cervical abnormality in a cervical sample with an automated apparatus, comprising: a) processing the sample in a pre-analytical unit of the automated apparatus, wherein the processing comprises contacting the sample with at least one fluorescently labeled probing agent that specifically recognizes a biomarker; b) transferring all or an aliquot of the processed sample to an analytical unit of the automated apparatus; c) measuring multiple parameters comprising at least two fluorescent activities and at least two types of light scattering for cells in the sample, wherein at least one of the fluorescent activities is produced by the fluorescently labeled probing agent; d) analyzing data obtained from c); and e) reporting the cervical sample as positive or negative, wherein the automated apparatus automatically performs a) through e).

In some embodiments, the invention provides an automated method for screening a cervical abnormality in a cervical sample with an automated apparatus, comprising: a) transferring the sample to a pre-analytical unit of the automated apparatus; b) processing the sample in a pre-analytical unit of the automated apparatus, wherein the processing comprises contacting the sample with at least one fluorescently labeled probing agent that specifically recognizes a biomarker; c) transferring all or an aliquot of the processed sample processed to an analytical unit of the automated apparatus; d) measuring for cells analyzed in the analytical unit multiple parameters comprising at least two fluorescent activities and at least two types of light scattering, wherein at least one of the fluorescent activities is produced by a fluorescently labeled probing agent that specifically recognizes a biomarker; e) analyzing the data obtained from d); and f) reporting the cervical sample as positive or negative, wherein the automated apparatus automatically performs a) through f).

The automated methods may also be directed to any one or more of the methods directed to any one or more of the methods described herein, such as multi-parameter analysis and detecting presence or absence of precancerous or cancerous cell. In some embodiments, the processing of the above-described automated methods comprises one or more of the following: disaggregating cell clusters in the sample to generate a cell suspension, filtering the sample to reduce obscuring factors in the sample, fixing/permeablizing cells in the sample, and measuring cell density in the sample.

The multiple parameters described herein may comprise at least two types of light scattering. In some embodiments, one type of the light scattering is forward light scattering. In some embodiments, one type of the light scattering is side light scattering. In some embodiments, one type of the light scattering is near infrared light scattering. In some embodiments, one type of the light scattering is forward light scattering, and another type of the light scattering is side light scattering. In some embodiments, the light scattering parameter(s) are used to estimate the size of the cell, estimate the nucleus to cytoplasm ratio of the cell, and/or serve as gating parameter(s) to exclude non-cell particles or cell debris.

The multiple parameters described herein may comprise at least two fluorescent activities. In some embodiments, at least one of the fluorescent activities is autofluorescence. Autofluorescence can be used as a gating parameter to exclude non-cell particles or cell debris, used to calibrate fluorescent activities of at least one fluorescently labeled probing agent, and/or used to reflect fluorescent activities arising from a marker for precancerous or cancerous cells.

In some embodiments, at least one of the fluorescent activities is produced by a fluorescently labeled probing agent specifically recognizing a biomarker. In some embodiments, at least two of the measured probing agents are produced by fluorescently labeled probing agents specifically recognizing different biomarkers. In some embodiments, one of the probing agents specifically recognizes p16INK4a. In some embodiments, one of the probing agents specifically recognizes a biomarker selected from the group consisting of Mcm5, Cdc6, PCNA, Ki-67, EGFR, Mcm2, Cyclin E, CKI WAF1, CKI KIP1, and telomerase. In some embodiments, one of the probing agents specifically recognizes p16INK4a, and another one of the probing agents specifically recognizes Cdc6. In some embodiments, one of the probing agents specifically recognizes p16INK4a, and another one of the probing agents specifically recognizes Mcm5. In some embodiments, one of the probing agents specifically recognizes p19INK4a, another one of the probing agents specifically recognizes Mcm5, and another one of the probing agents specifically recognizes Cdc6.

In some embodiments, the invention provides a method of determining the presence or absence of one or more precancerous or cancerous cells in a cervical sample, comprising: a) contacting a cervical sample with a fluorescently labeled probing agent specifically recognizing p16INK4a and a fluorescently labeled probing agent specifically recognizing Mcm5; b) measuring multiple parameters comprising fluorescent activities produced by the two probing agents, forward light scattering, and side light scattering; and c) determining the presence or absence of precancerous or cancerous cells.

In some embodiments, there is provided a method of screening a cervical abnormality in a cervical sample, comprising: a) contacting a cervical sample with a fluorescently labeled probing agent specifically recognizing p16INK4a and a fluorescently labeled probing agent specifically recognizing Mcm5; b) measuring multiple parameters comprising fluorescent activities produced by the two probing agents, forward light scattering, and side light scattering; and c) determining whether the cervical sample is positive or negative for a cervical abnormality.

In some embodiments, there is provided an automated method for screening a cervical abnormality in a cervical sample with an automated apparatus, comprising: a) transferring the sample to a pre-analytical unit of the automated apparatus, wherein the sample is processed by a method comprising 1) permeablizing cells in the sample, 2) contacting cells in the sample with a fluorescently labeled probing agent specifically recognizing p16INK4a and a fluorescently labeled probing agent specifically recognizing Mcm5; b) transferring all or an aliquot of the processed sample to an analytical unit of the automated apparatus, wherein cells are analyzed by measuring multiple parameters comprising fluorescent activities produced by the probing agents, forward light scattering, and side light scattering; c) analyzing the data obtained from b); and d) reporting the cervical sample as positive or negative based on the analysis of c), wherein the automated apparatus automatically performs a) through d). In some embodiments, the multiple parameters further comprise autofluorescence.

The probing agents specifically recognizing p16INK4a, Mcm5 or other biomarkers described herein can be antibodies recognizing p16INK4a, Mcm5, or other markers. In some embodiments, the probing agent specifically recognizing p16INK4a is a PE-anti-p16INK4a antibody conjugate. In some embodiments, the probing agent specifically recognizing Mcm5 is an APC-anti-Mcm5 or PerCP-anti-Mcm5 antibody conjugate.

The present invention also provides methods of evaluating results of the analytical methods described herein. Such evaluation generally entails reviewing such results and can assist, for example, in advising regarding clinical and/or diagnostic follow-up and/or treatment options. The present invention also provides kits containing reagents such as probing agents recognizing biomarkers for use in methods described herein.

In another aspect, there is provided an apparatus for carrying out any one or more of the above described and related methods for screening cells, including screening for precancerous or cancerous cervical cells in a sample of cervical cells. The apparatus in one embodiment is automated and integrated for processing a large number of samples.

In one embodiment, the invention provides an apparatus for cell sample screening, comprising: means for processing a sample of cells; means for transferring all or an aliquot of the sample processed in the means for processing to an analytical unit; means for measuring for each cell analyzed in the analytical unit at least two fluorescent activities, wherein at least one of the fluorescent activities is produced by a fluorescently labeled probing agent that specifically recognizes a biomarker and at least two types light scattering from each cell; and means for analyzing data obtained from the means for measuring, wherein the apparatus is controlled by a computer unit.

In one embodiment, the invention provides an apparatus for screening a cervical abnormality in a cervical sample, comprising: a pre-analytical unit wherein the sample is processed by 1) permeablizing cells in the sample, 2) contacting the sample with a fluorescently labeled probing agent specifically recognizing p16INK4a and a fluorescently labeled probing agent specifically recognizing Mcm5; an analytical unit coupled to the pre-analytical unit and wherein the processed cells are analyzed by measuring multiple parameters comprising fluorescent activities produced by the fluorescently labeled probing agents, forward light scattering, and side light scattering from the cells; a data management unit coupled to the analytical unit and reporting the sample as positive or negative based on the analysis of the processed cells.

In one embodiment, the invention provides an apparatus comprising a sample processing mechanism adapted to filter cells from a sample; a flow cell adapted to carry a stream of cells from the sample processing mechanism; a first light source directing a first light beam onto the stream of cells in the flow cell; and a plurality of detectors associated with the light beam.

In one embodiment, the invention provides an apparatus comprising a loader mechanism adapted to hold a plurality of sample vials; a sample processing mechanism coupled to the loader mechanism and adapted to filter cells from samples in the sample vials; and a flow cell coupled to the sample processing mechanism and adapted to carry a stream of the cells supplied from the sample processing mechanism for screening. In one embodiment, the invention provides an apparatus including interconnected elements including a sample loader for storing and handling a number of samples each sample being provided in a vial, a pre-analytical unit for preparing the samples including staining and filtering all or an aliquot of each sample, an analytical unit including a flow cytometer, and a post-analytical sample management unit for storing the sample vials with remaining portions of the samples. In some embodiments, the post-analytical sample management unit identifies sample vials containing positive samples and/or sort sample vials based on the positive or negative samples contained therein.

In some embodiments, the sample processing mechanism prepares cells for analysis by contacting cells with one or more of the labeled probing agents described herein.

In another aspect, the invention provides a reaction cartridge for use in the pre-analytical unit and which is used there for the cell sample preparation. The reaction cartridge is a sample cup unit including a plurality of chambers defined in a member (in some embodiments, one or more chambers; in some embodiments, one chamber), whereby the sample is prepared in the various chambers and transferred therebetween by the apparatus. At least one chamber includes two stacked filters for separating out the cells to be screened from larger and smaller particles found in the sample. Typically each reaction cartridge is used for only one sample and is disposable. In some embodiments, the reaction cartridge is adapted for use in conjunction with a flow cytometer.

In some embodiments, the invention provides a sample cup unit comprising: a member; a plurality of chambers defined in the member; at least one of the chambers having a first filter extending across the chamber and a second filter spaced apart from the first filter and extending across the chamber, wherein the first filter has a pore size differing from that of the second filter, the filters being adapted to filter cells; and wherein the first filter defines an opening to allow passage of a pipettor tip therethrough. In one embodiment, each chamber has a volume in the range of about 0.1 to about 10 milliliters. The invention further provides kits comprising one or more sample cup units.

In another aspect, there is provided a sampling device for collecting cell samples comprising: a sampling head having a shaft whose interior is hollow or pierceable; a middle portion coupled to the sampling head and having in its interior a pierceable portion; and a handle detachable from the middle portion. There is also provided a sample collection assembly comprising a vial cap ring, a vial adapted to be closed by the vial cap ring, and sampling device comprising a sampling head having a shaft whose interior is hollow or pierceable; a middle portion coupled to the sampling head and having in its interior a pierceable portion; and a handle detachable from the middle portion. There is also provided a method of using the sample collection assembly described herein for collecting cell samples, comprising: a) collecting a cell sample from a patient using the sampling device; b) attaching the sampling device to the vial cap ring; c) placing the sampling head of the sampling device in the vial; and d) detaching the handle, whereby the vial cap ring and the middle portion of the sampling device seal the vial. The present invention also provides kits comprising the sampling device or the sample collection assembly and instructions for use of the sampling device or sample collection assembly.

Although the methods and devices are sometimes described in the context of a multi-parameter analysis comprising measurements of at least two fluorescent activities and at least two types of light scattering, it is understood that any other aspects of the multi-parameter analysis described herein can be used in the methods.

BRIEF DESCRIPTION OF THE DRAWINGS

FIGS. 6(a)-6(d) show microscopic images of normal and dysplastic (precancerous) cells from a HSIL cervical specimen stained with the cocktail antibodies (PE-p16INK4a and APC-Mcm5). FIG. 6(a) is a DIC (Differential Interference Contrast) image. FIG. 6(b) is a FITC image. FIG. 6(c) is a PE image. FIG. 6(d) is an APC image. The numbers under the cells are the average fluorescence intensities of the cells.

FIGS. 11(a) and 11(b) shows dot plots of PE versus APC immunofluorescent intensities (logarithmic scale) of cells in a negative cervical specimen (11(a)) and HSIL cervical specimen (11(b)). The cells were stained with PE-p16INK4a and APC-Mcm5 antibodies and analyzed by flow cytometry. About 75,000 cervical cells are included in each plot.

FIG. 22 shows a resuspension of cervical cells using the reaction cartridge of FIG. 19.

FIGS. 23(a) and 23(b). 23(a) shows cell staining involving transfer of cell suspension using the reaction cartridge of FIG. 19; FIG. 23(b) shows cell density measurement of the cell suspension of FIG. 23(a).

FIG. 24 shows eliminating of unbound antibodies in chamber 4 of the of the reaction cartridge of FIG. 19.

FIG. 25 shows resuspension of stained cells after elimination of unbound conjugated antibodies using chamber 4 of the reaction cartridge.

FIG. 26 shows the internal mechanism of the analytical unit of the apparatus of FIG. 15 wherein cells are analyzed in a flow cell.

FIGS. 27(a)-27(c). 27(a) shows graphically analysis of cell morphology, e.g., cytoplasm size, using the apparatus of FIG. 26; FIG. 27(b) shows nucleus size analysis using the apparatus of FIG. 26; FIG. 27(c) shows calculation of cytoplasm to nucleus ratio using the measurements of FIGS. 27(a) and 27(b).

DETAILED DESCRIPTION OF THE INVENTION

Figure 1:
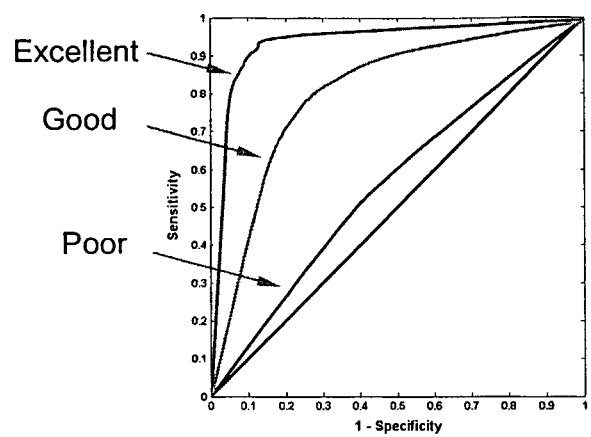
FIG. 1 shows representative ROC curves for excellent, good, and poor diagnostic tests.

The present invention provides methods of screening cervical samples for cervical cell abnormalities (such as cervical dysplasia, cervical neoplasia, or cervical cancer). The methods use multiple parameters to analyze cells in a cervical sample. Generally, a sample is contacted with one or more probing agents that recognize biomarkers differentially expressed on precancerous or cancerous cells. The probing agents are labeled (e.g., with fluorochrome) before or after they are brought into contact with the sample. The stained sample is then analyzed in a detection instrument, wherein measurements of fluorescence intensities (and/or other labels) and light scattering are taken for cells examined. The measurements or parameters taken for each examined cell may be stored in a data storage and analysis system and analyzed in real time or at a later time. By analyzing these multiple parameters, the condition of each examined cell can be assessed and classified as normal or precancerous or cancerous, and the sample can be determined to be negative or positive for one or more cervical cell abnormalities. In some embodiments, the methods are automated with two or more (in some embodiments, all) steps performed by an automated instrument. By integrating these steps, screening becomes efficient, convenient, and not as reliant on more traditional methods known in the art, such as inspection of slides.

The present invention also provides an integrated apparatus for carrying out the methods described herein and related processes. Automated cervical cancer screening and related cell screening devices are described which accept a sample of cervical cells, automatically label, prepare and examine cells in the sample, and provide an output. In one embodiment, the automated device indicates if a sample is "positive" or "negative" and may give a more- or less-detailed description of the cells in the sample based on cellular morphology and/or the presence of markers correlated to cervical cancer.

Definitions

As used herein, "cervical dysplasia" refers to a premalignant or precancerous change to the cells on the surface of the cervix. The term includes dysplasia at different levels, such as mild, moderate, and severe dysplasia.

As used herein, "cervical abnormality" or "cervical cell abnormality" refers to abnormality in a cervical sample, and includes, but is not limited to, cervical dysplasia, cervical neoplasia, and cervical cancer.

As used herein, "precancerous or cancerous" cervical cells refer to cells of mild to severe cervical dysplasias and their precursory stages, cervical neoplasia, as well as carcinomas such as carcinoma in situ, invasive carcinoma, and disseminated tumor cells. Precancerous or cancerous cells can arise from any type of cells from a cervical sample, such as squamous cells (such as ASCUS, LSIL, HSIL, and SCC), glandular cells (such as atypical glandular cells, atypical glandular cells that favor neoplastic, and endocervical adenocarcinoma in situ), or stroma cells (such as stroma cancer cells).

As used herein, "cell debris" refers to non-cellular portions of a cervical cell sample, including parts of cells independent of an intact cell (e.g., membrane fragments), fibrous but non-cellular tissues, dusts, contaminants, and portions of any collector used to collect the cervical cell sample.

As used herein, "biomarker" refers to a marker that indicates, alone or in combination with other parameters, one or more aspects of a cervical cell abnormality. For example, the biomarker may be differentially expressed (either overexpressed or underexpressed) in precancerous or cancerous cells, at the transcription level or at the translation level. Thus, a biomarker may be any molecule transcribed from a gene, such as an mRNA, or any molecule translated from such transcript, such as proteins, proteoglycans, polypeptides, etc. Detection of various biomarkers as indicating one or more aspects of a cervical abnormality may be qualitative and/or quantitative.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "near infrared light scattering" refers to light scattering that uses near infrared light as an incident light.

A probing agent (such as an antibody) "specifically recognizes" a biomarker if it binds to the biomarker with greater affinity, avidity, more readily, and/or with greater duration than it binds to other molecules.

As used herein, "autofluorescence" or "cellular autofluorescence" refers to the emission of fluorescence from intrinsic molecules in the cell. Autofluorescence molecules in the cell include, but are not limited to, tryptophan, NADH, and flavin.

Two or more biomarkers are detected "simultaneously" means that these biomarkers are detected in a single multi-parameter analysis.

As used herein, the singular form "a", "an", and "the" include plural references unless indicated otherwise. For example, "an" antibody includes one or more antibodies and "a cervical abnormality" means one or more cervical abnormalities.

A. Methods of Detecting Cervical Abnormality by Multi-Parameter Analysis of Cervical Cells The present invention provides multi-parameter analysis methods for analyzing cervical cells.

In one aspect, the method comprises measurement of at least two fluorescent activities and at least two types of light scattering. In some embodiments, at least one fluorescent activity is produced by a fluorescently labeled probing agent that specifically recognizes a biomarker. In some embodiments, at least two of the measured fluorescent activities are produced by fluorescently labeled probing agents that specifically recognize different biomarkers. In some embodiments, at least one of the measured fluorescent activities is produced by a fluorescently labeled probing agent that specifically recognizes a biomarker, and at least one of the measured fluorescent activities is cellular autofluorescence. In some embodiments, at least one of the measured light scattering is forward light scattering. In some embodiments, at least one of the measured light scattering is side light scattering. In some embodiments, at least one of the measured light scattering is near infrared light scattering. In some embodiments, at least one of the measured light scattering is forward light scattering and at least one of the measured light scattering is side scattering.

In another aspect, the method comprises measurements of at least three fluorescent activities and at least two types of light scattering. In some embodiments, at least three of the measured fluorescent activities are produced by fluorescently labeled probing agents that specifically recognize different biomarkers in the cell. In some embodiments, at least two of the measured fluorescent activities are produced by fluorescently labeled probing agents that specifically recognize different biomarkers in the cell, and at least one of the measured fluorescent activities is cellular autofluorescence. In some embodiments, at least one of the measured light scattering is forward light scattering. In some embodiments, at least one of the measured light scattering is side light scattering. In some embodiments, at least one of the measured light scattering is near infrared light scattering. In some embodiments, at least one of the measured light scattering is forward light scattering and at least one of the measured light scattering is side scattering.

In another aspect, the method comprises measurement of at least two fluorescent activities and at least one type of light scattering, wherein at least one of the fluorescent activities is produced by fluorescently labeled probing agent that specifically recognizes a biomarker in the cell and at least one of the fluorescent activities is cellular autofluorescence. In some embodiments, at least one of the measured light scattering is forward light scattering. In some embodiments, at least one of the measured light scattering is side light scattering. In some embodiments, at least one of the measured light scattering is near infrared light scattering.

In another aspect, the method comprises measurement of at least three fluorescent activities and at least one type of light scattering, wherein at least two of the fluorescent activities are produced by fluorescently labeled probing agents that specifically recognize different biomarkers in the cell and at least one of the fluorescent activities is cellular autofluorescence. In some embodiments, at least one of the measured light scattering is forward light scattering. In some embodiments, at least one of the measured light scattering is side light scattering. In some embodiments, at least one of the measured light scattering is near infrared light scattering.

In another aspect, the method comprises measurement of at least one fluorescent activity and at least two types of light scattering, wherein at least one of the measured fluorescent activity is cellular autofluorescence.

In some embodiments, the methods comprise a multi-parameter analysis of cells in a cervical sample, wherein these multiple parameters comprise forward light scattering, side light scattering, a fluorescent activity produced by a fluorescently-labeled probing agent recognizing p16INK4a, and a fluorescent activity produced by a fluorescently-labeled probing agent recognizing Mcm5. In some embodiments, the multi-parameters include forward light scattering, side light scattering, a fluorescent activity produced by a PE-p16INK4a antibody, and a fluorescent activity produced by a PerCP (peridinin chlorophyll)-Mcm5 (or APC-Mcm5) antibody.

In some embodiments, the methods comprise a multi-parameter analysis of cells in a cervical sample, wherein these multiple parameters comprise forward light scattering, side light scattering, autofluorescence, and a fluorescent activity produced by a fluorescently-labeled probing agent recognizing p16INK4a. In some embodiments, the multiple parameters comprise forward light scattering, side light scattering, autofluorescence, a fluorescent activity produced by probing agent recognizing p16INK4a, and a fluorescent activity produced by a probing agent recognizing Mcm5.

In some embodiments, the multi-parameters comprise forward light scattering, side light scattering, autofluorescence, and a fluorescent activity produced by PE-p16INK4a antibodies and a fluorescent activity produced by PerCP-Mcm5 (or APC-Mcm5) antibodies. In some embodiments, the first three of the five parameters provided above (i.e., forward light scattering, side light scattering, and autofluorescence) are used as gating parameters to exclude data from non-cell materials, non-epithelial cervical cells, and cell debris from further analysis, while the other two parameters (i.e., the fluorescence intensities from p16INK4a and Mcm5 antibodies) are used to determine if a cell is normal or precancerous/cancerous.

In some embodiments, the multiple parameters include a 488 nm forward light scattering, a 488 nm side light scattering, autofluorescence at the FITC (fluorescein isothiocyanate) channel, a fluorescent activity produced by PE-p16INK4a antibodies, and a fluorescent activity produced by PerCP-Mcm5 (or APC-Mcm5) antibodies. The 488 nm forward scattering is used as a registration signal as well as a threshold signal. Only cells with a forward signal brighter than the defined channel threshold will be selected. The signals from the rest of the parameters that are registered (occurring time) with the selected forward scattering signal will be analyzed. The use of a forward scattering threshold can avoid the analysis of signals from dust or debris (usually with very low forward scattering). The intensity of the 488 nm forward scattering also correlates with the rough size of the cells. Therefore, it may also be used to reject small cells (e.g. red blood cells).

The 488 nm side scattering is used as a secondary gating parameter which, in combination with forward light scattering, to distinguish cells of the cervical origin from other types of cells such as blood cells, cell debris, and non-cell particles. Side scattering increases with cell's internal granularity and surface roughness. Cell internal granularity is closely related to the cell nuclear size, nuclear contents, and the number of cell organelles." Side scattering also provides information of cervical cell types, such as superficial squamous cells, intermediate cells, parabasal cells, endocervical cells, and endometrial cells. The information of cervical cell types will help identify precancerous or cancerous cervical cells. For example, parabasal cells usually have a relatively larger nucleus/cytoplasm ratio than normal superficial cells, but those cells are not "precancerous or cancerous".

The fluorescence intensity of the FITC channel may correlate with the autofluorescence of each cell. Using this intensity, the autofluorescence in the PE and PerCP (or APC) bands of this cell can be removed. The average autofluorescence of a specimen also provides the amount of flavin molecules of the specimen. This information is likely related to the precancerous or cancerous change of the cells.

The fluorescence intensity of PE may be used to give the expression status of p16INK4a in appropriately labeled probing agents. The fluorescence of PerCP (or APC) provides the abundance of Mcm5 protein in a cell.

This discussion describes using fluorescently labeled markers (probing agents) to identify levels of biomarkers associated with (or correlated with) cervical cancer. However, it is not intended that this description is limited to fluorescent labeling and detection methods. Other methods of labeling and detecting biomarkers are also contemplated, including at least: radiolabeling (e.g. $P^{32}$, $S^{35}$, $I^{125}$, etc.), magnetic labeling, enzymatic labeling (e.g. HRP, etc.), and the like. These methods may be used in stead of, or in addition to, fluorescent labeling and detection.

As described herein, one or more of these parameters (such as forward light scattering, side light scattering, and/or autofluorescence) may be used as gating parameters to exclude data from non-cell materials, non-epithelial cervical cells, and cell debris from further analysis.

The multi-parameter cell analysis methods described herein can be useful for classifying a cell in a cervical sample as precancerous or cancerous or determining the presence of absence of precancerous or cancerous cell(s) in a sample. The methods may be useful for the identification of squamous cells of different malignancy levels including, but not limited to, ASCUS, LSIL, HSIL, and SCC. The methods may also be useful for the identification of abnormal cervical glandular cells (such as atypical glandular cells, atypical glandular cells that favor neoplastic, and endocervical adenocarcinoma in situ) and abnormal stroma cells (such as stroma cancer cells). The methods can also be used for screening for a cervical abnormality in a sample. For these methods, a cervical sample (a sample that contains cervical cells such as cervical epithelial cells) is provided. Obtaining and processing such samples are described herein. Processing may include any of a number of pre-analytical manipulations, which, in some embodiments, are integrated (in some embodiments, by automation) with the analytical methods described herein.

The different components of the multi-parameter analysis methods described herein are discussed below in further detail, with the understanding that the discussion is applicable to all aspects and embodiments described herein.

Biomarkers

Biomarkers useful for cervical cancer screening are known in the art, and include, but are not limited to, p16INK4a, Mcm5, Cdc6, p53, PCNA, Ki-67, EGFR, Cyclin E, Cyclin A, Cyclin B, MN, her2/neu, Mdm-2, Bcl-2, EGF receptor, CKI WAF1, CKI KIP1, telomerase, Rb, Mcm proteins (such as Mcm2, Mcm3, Mcm4, Mcm6, Mcm7), p14ARF, Cdc7, Dbf4, Cdc14, Cdc45, Mcm10, claudlin-1, replication protein A (RPA), replication factor C (RPC), Unc53, FEN1, transferring receptor, GAPDH, Ki-S5, and Ki-S2.

Additional biomarkers can also be identified using methods known in the art. For example, biomarkers can be identified by looking at differential expression between normal and cancerous/precancerous cells at the mRNA level, by methods such as nucleic acid-based microarrays and differential screening methods. Biomarkers can also be identified by looking at differential expression between normal and cancerous/precancerous cells at the protein level, by methods such as mass-spectrometry-based proteomics methods and protein chips or microarrays.

In some embodiments, the biomarker is specifically expressed in cells at certain malignancy levels. For example, the biomarker may be specifically expressed in any one or more of the following types of cells: ASCUS, LSIL, HSIL, and SCC. In some embodiments, the biomarker is specific to any one or more of the following types of cells: atypical glandular cells, atypical glandular cells that favor neoplastic, endocervical adenocarcinoma in situ, and stroma cancer cells.

In some embodiments, the biomarker is a molecule involved in cell cycle control. These include, for example, molecules required for cell-cycle progression, DNA replication, DNA synthesis, and cell cycle control. In some embodiments, the biomarker is a molecule encoded by a gene belonging to one of the following gene classes: oncogenes, tumor suppressor genes, apoptosis genes, proliferation genes, repair genes, and viral genes. In some embodiments, the biomarker is a marker of active cell proliferation. A proliferating cell can be a cell that is proliferating as a result of normal cellular activity or as a result of dysplasia or other cellular abnormality that may or may not progress into a cancerous cell.

P16INK4a

In some embodiments, a biomarker for detection is p16INK4a. The p16INK4a protein, also named p16, is a Cyclin-dependent kinase inhibitor that maintains Rb in the hypophosphorylated active state. In cervical carcinomas, viral DNA from HPV is integrated into the host genome at the E2 region, resulting in assimilation of HPV oncogene E6 and E7 into host DNA and upregulation of p16INK4a. See Saqi et al., Diagn Cytopathol., 27(6):365-70 (2002). Several studies have shown an increase in p16INK4a expression in cervical carcinomas and squamous intraepithelial lesions. For example, Bibbo et al. have shown that almost 100% of high-grade cervical dysplasia and invasive cancers express very high levels of p16INK4a, whereas nonprecancerous or cancerous cervical epithelia do not test positive for p16INK4a. See, e.g., Bibbo et al., Anal. Quant. Cytol. Histol., 25(1):8-11 (2003); Bibbo et al., Acta. Cytol., 46(1):25-9 (2002).

Other mRNAs transcribed from the p16INK4a gene locus or polypeptides translated from such an mRNA may also be used as biomarkers. In one embodiment, the biomarker is an expression product encoded by the p16INK4a gene that exhibits molecular weights of about 5 to about 49 kDa, about 10 to about 20 kDa, about 14 to about 19 kDa. In one embodiment, the biomarker is the p14ARF protein. In some embodiments, more than one different gene products of the p16INK4a gene are detected simultaneously, for example, the presence of p16INK4a and p14ARF can be simultaneously detected.

Mcm Proteins

In some embodiments, a biomarker for detection is a Mcm protein. Mcm proteins are members of the pre-replication complex that are essential for licensing DNA replication and limiting replication to only one per cell cycle. Mcm2, Mcm3, Mcm4, Mcm5, Mcm6 and Mcm7 form a hetero-hexamer that is believed to act as a replicative DNA helicase. Mcms are abundant in the nucleus throughout the cell cycle but are degraded on exit from the cell cycle, with rapid breakdown following differentiation and slower breakdown in quiescence and senescence.

All six Mcm members show essentially similar distributions. They are restricted to normal epithelial proliferative compartments, but are rapidly lost from differentiating cell. By contrast, there is abundant expression of Mcms in malignancy and pre-malignancy at numerous sites, including in surface epithelial layers from which cells can exfoliate spontaneously or be sampled. For example, it was found that around 50% of cells in the most superficial layers of CINI lesions were positive for Mcm5, and more than 90% of superficial cells in CINIII lesions express Mcm2, Mcm5, and Mcm7. Freeman et al., Clinical Cancer Research, 5:2121-2132 (1999).

In some embodiments, the biomarker is Mcm5. Mcm5 is disclosed in Hu et al., 1993, Nucleic Acid Res., 21, 5289-93, GenBank Acc. No. X74795, and has been shown to mark precancerous or cancerous cells. See, William et al., Proc. Natl. Acad. Sci. 95(25):14932-7 (1998).

Cdc6

In some embodiments, a biomarker for detection is Cdc6. Cdc6 is involved in the regulation of DNA replication, and has been shown to mark precancerous or cancerous cells. The amino acid sequence of human Cdc6 is disclosed in Williams et al., Proc. Natl. Acad. Sci. 94:142-147 (1997), GenBank Acc. No. U77949. An indirect immunoperoxidase method to stain tissues for Cdc6 protein showed that Cdc6 staining was exclusively nuclear and was rarely present in specimens of normal cervical squamous mucosa or endocervical glands. Staining was present in most (65%) cases of CINI, in the majority (89%) cases of CIN II, and in all (100%) cases of CIN III and squamous cell carcinomas. The proportion of cells staining for Cdc6 increased with the grade of dysplasia, and the proportion of stained cells in squamous cell carcinomas was similar to that in lesions of high-grade dysplasia.

HPV Molecular Markers

In certain embodiments, a detection of HPV associated marker molecules or makers for viral activity may be used for a detection of a dysplasia. For example, HPV molecular markers such as E6, E7 oncoproteins can be used.

Two or More Biomarkers

Two or more different biomarkers may be detected simultaneously. These biomarkers may provide the same information about the cell, or may be complementary to each other, i.e., the two biomarkers provide different information about the cells. For example, the different biomarkers that are complementary to each other may be expressed in different kinds of precancerous or cancerous cells, reflect different functional aspects of a cell, or vary in their abundance and distribution, either temporally (for example, as being present in different phases of the cell cycle) or spatially (for example, as being in the nucleus or in the cytoplasm).

In some embodiments, p16INK4a is detected simultaneously with a cell proliferation marker. In normally controlled cells, p16INK4a inhibits Cdk4 and thus inhibits cell proliferation. In contrast, in precancerous or cancerous cells this regulation is impaired. Thus, despite of high p16INK4a expression level, the precancerous or cancerous cells can still undergo proliferation and express cell proliferation markers. The combination of p16INK4a and cell proliferation marker expression therefore differentiates normal cells from precancerous or cancerous cells. Suitable cell proliferation markers that can be simultaneously detected with p16INK4a for the present invention are described, for example, in WO04/03848.

In some embodiments, p16INK4a is detected simultaneously with Mcm5 and/or Cdc6. Mcm5 and Cdc6 proteins were found to be able to detect ASCUS, while p16INK4a is more sensitive and specific for the detection of LSIL and HSIL. Thus, co-expression of p16INK4a and Mcm5 and/or Cdc6 correlates well with the precancerous or cancerous condition of a cell.

Mcm5 and Cdc6 may also provide information complementary to each other. While Cdc6 is usually overexpressed on highly dysplastic cells, Mcm5 is also overexpressed on less severely dysplastic cells. Mcm5 and Cdc6 may therefore collectively serve as biomarkers for the identification of precancerous or cancerous cells (such as dysplastic cells). Thus, in some embodiments, Mcm5 is detected simultaneously with Cdc6. In some embodiments, p16INK4a, Mcm5, and Cdc6 are detected simultaneously.

In some embodiments, other additional marker molecules such as markers for arrested cells, markers for terminally differentiated cells, markers for apoptotic cells, markers for viral infection or for viral activity in cells or cell cycle regulatory proteins can be detected simultaneously with p16INK4a, Mcm5, or Cdc6 in various combinations.

In some embodiments, other additional agents can be used to differentiate epithelial cells from non-cell debris and PMNs (polymorphonuclear leukocytes). For example, nuclear dyes can be used to stain cellular DNA and used to differentiate intact cells from non-cell debris. CD16 staining only tags PMNs and thus can be used to differentiate PMNs from epithelial cells. CAM5.2, a low-molecular-weight keratin protein, is only expressed in endocervical glandular cells. An antibody recognizing CAM5.2 can therefore be used to differentiate endocervical cells from squamous cells.

Fluorescently Labeled Probing Agents
Probing Agents

Probing agents used in the present invention may be any agents binding specifically to a biomarker molecule. In the case of detecting nucleic acids, the probing agent may be a complementary nucleic acid probe, a protein with binding specificity for the nucleic acids, or any other agents specifically recognizing and binding to the nucleic acids. In the case of detecting polypeptides or proteins, the probing agent may be a binding agent such as an antibody, a ligand, or a protein that specifically interacts with the polypeptides or proteins.

In some embodiments, the probing agent is an antibody that specifically recognizes a biomarker. The antibodies used herein can be monoclonal antibodies, polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize biomarker(s). Antibodies used herein also include an antibody fragment, such as Fab, Fab', F(ab')2, Fv fragments, diabodies, single chain antibody molecules and multispecific antibodies formed from antibody fragments, and a single-chain Fv (scFv) molecules.

In some embodiments, the probing agent is an antibody recognizing p16INK4a. Antibodies for p16INK4a are known in the art, and include clone E6H4 (MTM Laboratories, Heidelberg, Germany), clone DSC-50 (Oncogene Research Products, Cambridge, Mass.), clone ZJ11 (LabVision, Fremont, Calif.), clone JC8 (LabVision, Fremont, Calif.), clone G175-405 (PharMingin, San Diego, Calif.), and mouse monoclonal anti-p16INK4a (Biosource, Camarillo, Calif.). P16INK4A antibodies obtained from other sources or generated using methods known in the art can also be used.

In some embodiments, the probing agent is an antibody that recognizes Mcm5. Antibodies for Mcm5 are known in the art, and include mouse mAb Mcm5 (DBS, Pleasanton, Calif.), clone CRCT5.1 (LabVision, Fremont, Calif.), and ab6164 (Novus Biologicals, Inc.). Mcm5 antibodies obtained from other sources or generated using methods known in the art can also be used.

In some embodiments, the probing agent is an antibody that recognizes Cdc6. Antibodies for Cdc6 are known in the art, and include clone DSC-180 (LabVision, Fremont, Calif.), anti-Cdc6 (human), and mouse IgG2a monoclonal 37F4 (Molecular Probes, Eugene, Oreg.). Cdc6 antibodies obtained from other sources or generated using methods known in the art can also be used.

In some embodiments, each probing agent recognizes a single biomarker. In some embodiments, each probing agent recognizes a group of two or more biomarkers. For example, the probing agent can be an antibody recognizing a group of cell proliferation proteins sharing a common epitope.

In some embodiments, two or more probing agents may be used for the detection of a single biomarker or a single group of biomarkers. For example, two or more different probing agents against a single biomarker (e.g., antibodies directed against different epitopes of the biomarker; oligonucleotide probes hybridizing to different sequences of the biomarker, or various combinations thereof) can be used. These probing agents may be (but not necessarily) labeled with a same fluorochrome, and thus produce the same fluorescent signal and provide cumulative information about the biomarker or the group of biomarkers.

Fluorescent Label

The probing agents may be labeled with fluorochromes. Suitable fluorochromes include, but are not limited to, phycoerythrin (PE), peridinin chlorophyll (PerCP), and allophycocyanin (APC). The FITC, PE and PerCP fluorochromes can be excited with an Argon or a solid-state laser system emitting a 488 nm wavelength. The emission of the PE and PerCP are 575±25 nm (yellow) and 677±25 nm (red), respectively. APC can be excited by an air-cooled HeNe laser (633 nm). The emission wavelength of APC is at 660±20 nm. The fluorochromes may be chosen according to the set-up of the detection instrument used. For example, when a single-excitation flow cytometer is used, the fluorochromes are preferably those that can be excited by a single wavelength. Other fluorochromes suitable for the methods are known in the art. Exemplary fluorochromes are provided in Table 1.

TABLE 1

Useful Exemplary Fluorochromes

| Fluorochrome | Excitation wavelength ($\lambda$max)(nm) | Emission wavelength ($\lambda$max)(nm) | probing agent or agent that binds to probing agent |
|---|---|---|---|
| FTIC | 488 | 525 | protein |
| PE | 488 | 575 | protein |
| APC | 630 | 650 | protein |
| PerCP ™ | 488 | 680 | protein |
| Cascade Blue | 360 | 450 | protein |
| Coumerin-phalloidin | 350 | 450 | protein |
| Texas Red ™ | 610 | 630 | protein |
| Tetramethylrhodamine-amines | 550 | 575 | protein |
| CY3 (indotrimethine-cyanines) | 540 | 575 | protein |
| CY5 (indopentamethine-cyanines) | 640 | 670 | protein |
| CY2 | 488 | 506 | protein |
| TRITC | 568 | 577 | protein |
| PE-TXR | 488 | 615 | Protein |
| PE-Cy5 | 488 | 667 | protein |
| PE-Cy5.5 | 488 | 695 | protein |
| PE-Cy7 | 488 | 767 | protein |
| PerCP-Cy5.5 | 488 | 695 | protein |
| APC-Cy5 | 647 | 667 | protein |
| APC-Cy5.5 | 647 | 695 | protein |
| APC-Cy7 | 647 | 767 | protein |

TABLE 1-continued

Useful Exemplary Fluorochromes

| Fluorochrome | Excitation wavelength ($\lambda$max)(nm) | Emission wavelength ($\lambda$max)(nm) | probing agent or agent that binds to probing agent |
|---|---|---|---|
| Hoechst 33342 (AT rich)(uv) | 346 | 460 | DNA/RNA |
| DAPI (uv) | 359 | 461 | DNA/RNA |
| POPO-1 | 434 | 456 | DNA/RNA |
| YOYO-1 | 491 | 509 | DNA/RNA |
| Acridine Orange (RNA) | 460 | 650 | RNA |
| Acridine Orange (DNA) | 502 | 536 | DNA |
| Thiazole Orange (vis) | 509 | 525 | DNA/RNA |
| TOTO-1 | 514 | 533 | DNA/RNA |
| Ethidium Bromide | 526 | 604 | DNA/RNA |
| PI (uv/vis) | 536 | 620 | DNA/RNA |
| 7-Aminoactinomycin D (7AAD) | 555 | 655 | DNA/RNA |

In some embodiments, at least one of the probing agents is labeled with quantum dot. Quantum dots are color-tunable semiconductor nanocrystals with a wide absorption and narrow emission spectrum. The larger the quantum dot the longer wavelength emitted. The broad absorption spectrum allows many different quantum dots to be excited with one excitation source. Efficient optical excitation is possible with a variety of laser source, including the standard 488 nm excitation light source. The emission spectrum for each dot is typically very narrow, on the order of 30 nanometers, which provides high spectral resolution. The quantum dots used herein are typically water soluble, and are capable of being conjugated to the probing agent or an agent binding to the probing agent. This can be achieved, for example, by functionalizing the nanocrystal surface of the quantum dot with water-soluble, reactive chemical moieties.

The probing agents may be directly conjugated to a fluorochrome or labeled indirectly. Methods of making direct fluorochrome conjugated probing agents are known in the art. For example, antibodies can be conjugated to corresponding fluorochromes using commercially available labeling kits such as those provided by ProZyme Inc. After conjugation, the free fluorochromes can be removed by methods known in the art such as size exclusion chromatography. The fluorochrome may also be conjugated to DNA/RNA probes using methods known in the art.

In some embodiments, the probing agents are labeled indirectly. For example, an antibody can be indirectly labeled by a secondary antibody that is conjugated to a fluorochrome. Other interactions, such as biotin-avidin interaction, may also be utilized.

Sample Collection and Device for the Same

Any suitable sample from the cervical region can be analyzed using the methods described herein. For example, the sample may comprise biopsies or microbiopsies of the cervix or swabs taken from the cervical region. Cervical swabs as used herein are samples that may be obtained using a suitable device such as a brush, a broom, a tampon, a spatula, or the like, which is contacted with the uterine cervix during the sampling procedure. In another embodiment, the sample can be collected using a personal sampling device such as the collector described in U.S. Pat. No. 6,352,513, or by using a physician's collector. In some embodiments, the sample is collected by a sampling device or sample collection assembly described further below.

Figure 12:
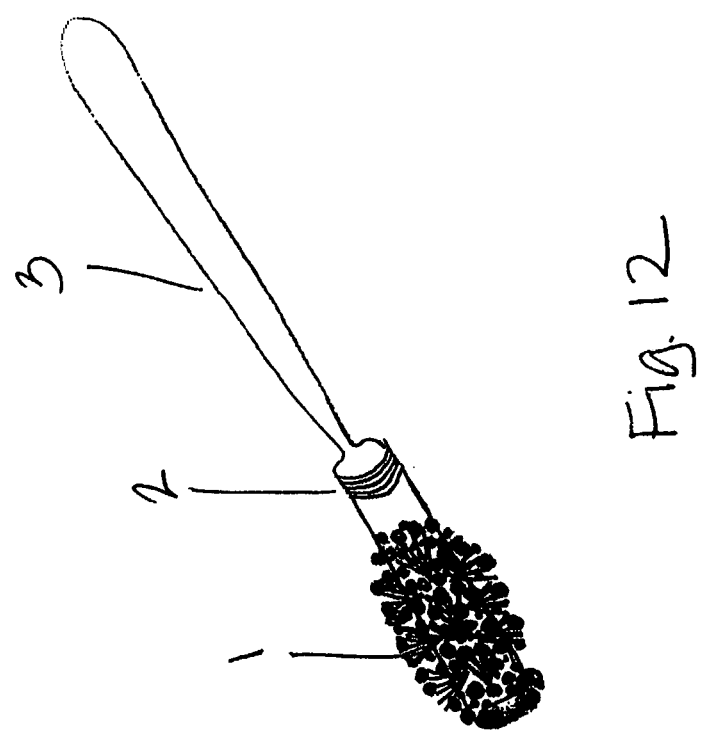
FIG. 12 shows a brush for collecting cervical cells.

The invention provides a sampling device for collecting cell samples, such as cervical samples. Examples of other samples include skin, oral, bladder, and lung samples. FIG. 12 shows one embodiment of such device. As shown in FIG. 12, the device comprises sampling head 1 having a shaft whose interior is hollow or pierceable, a middle portion 2 coupled to the sampling head and having in its interior a pierceable portion, and a handle 3 detachable from the middle portion.

Figure 13:
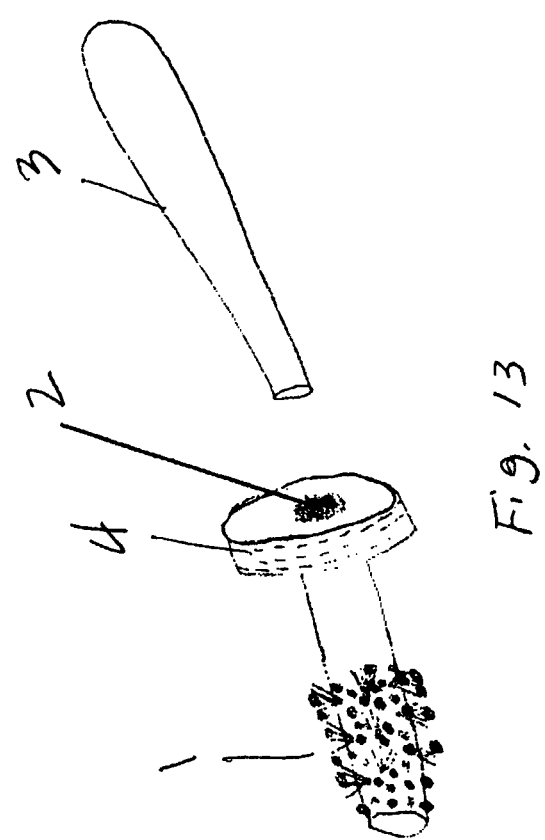
FIG. 13 shows the brush of FIG. 12 in use.
Figure 14:
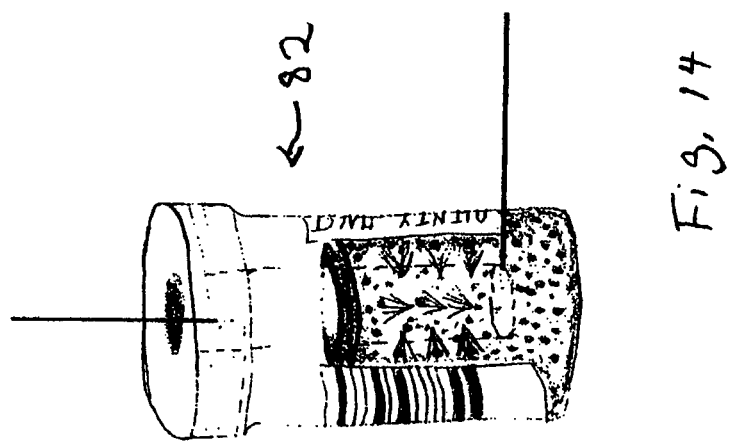
FIG. 14 shows a collection vial for use with the brush of FIG. 12.

There is also provided a sample collection assembly including a sampling device described herein, a vial, and a vial cap ring. As exemplified in FIG. 13, the sampling device can be inserted into the vial cap ring 4 from either end and thereby attach to the vial cap ring. The handle can be detached from the rest of the device before or after the sampling device (or part of the device) is attached to the vial cap ring. After the handle is detached, the vial cap ring and the middle portion of the device form a closure that seals the sampling head in vial 82 (see FIG. 14).

The sampling head is the part of the device that is brought into contact with the sample source (such as the cervix) and used to collect the sample (such as a cervical sample). The sampling head has a shaft whose interior is hollow or pierceable, e.g., by a pipettor tip. In some embodiments, the interior of the shaft in the sampling head is hollow. In some embodiments, the interior of the shaft is partially hollow. For example, one or more portions of the interior of the shaft may contain pierceable materials. In some embodiments, the entire interior of the shaft is filled with or made of pierceable materials. Pierceable used herein refers to allowing a sharp object such as a pipettor tip to go through. The sharp object, when removed, may or may not leave an opening behind. For example, when the pierceable material is resealable, the sharp object would not leave an opening behind.

The inner diameter of the shaft can be any dimension that is sufficient to allow penetration of a pipettor tip, and is typically more than 0.5 mm, such as any of about 0.8 mm, about 1 mm, about 2 mm, about 5 mm, about 8 mm.

The sampling head described herein can be in any configuration known in the art. For example, in some embodiments, the sampling head is a cylindrical brush as depicted in FIG. 12. Typically, the brush is about 1 to about 3 cm long, with an outer diameter of about 0.2 to about 1.6 cm, such as about 0.5 to about 1 cm.

In some embodiments, the sampling head is a broom shape. A broom in the context of the present invention typically has a shaft and a shoulder, wherein the shoulder has multiple bristles attached thereto. In some embodiments, the part of the shoulder that connects to the shaft is hollow or pierceable. In some embodiments, the part of the shoulder that connects to the shaft is free of bristles. The broom is typically about 0.2 to 5 cm long, such as about 0.5 cm, about 1 cm, about 2 cm; and about 0.5 to about 2 cm wide, such as about 1 cm, about 1.5 cm, about 2 cm.

In some embodiments, the sampling head is a spatula shape. The spatula typically has a shaft and an end piece, which, when used to collect cervical samples, may be shaped to conform to the natural curvature of the cervix. In some embodiments, the part of the end piece that connects to the shaft is hollow or pierceable.

The bristles for the sampling head (for brush and broom, for example) typically have a round cross-section. However, bristles with other shapes of cross-sections such as square, rectangular, triangular, pie segment and cross-shape may also be used. The average diameters for the bristles can be between about 1 μm to about 300 μm, such as between about 5 μm to about 10 μm. The average length of the bristles depends on the particular configuration of the sampling head. Typically, the brush or broom bristles are about 0.02 to about 0.3 cm long.

Suitable materials for the sampling head include, but are not limited to, plastic, such as polypropylene, polyethylene, polycarbonate, polyimide, polyamide (e.g., nylon), PTFE (Teflon®), and polystyrene. Suitable materials for the bristles (if any) include, but are not limited to, plastic, such as polypropylene, polyethylene, polycarbonate, polyimide, polyamide (e.g., nylon), PTFE (Teflon®), and polystyrene.

The middle portion of the sampling device connects the sampling head to the handle. The middle portion may also be used to connect the sampling device (with or without the handle) to a vial cap ring. The sampling device can be connected to the vial cap ring through a variety of ways. For example, the sampling device can be screwed onto the vial cap ring, that is, the outer perimeter of the middle portion may have a series of threads that are complementary to threads on the inner perimeter of the vial cap ring. Alternatively, the middle portion of the sampling device can be snapped onto the vial cap ring, or connected to the vial cap ring by other means such as clips.

The middle portion of the sampling device has in its interior a pierceable portion. Any materials that can be pierced can be used, and include, for example, rubber, foil, or plastic. In some embodiments, the pierceable portion is made of rubber. In some embodiments, the pierceable portion is made of a material that is re-sealable. The pierceable portion in the middle portion is typically about 0.1 to about 1 cm thick, such as about 0.2 to about 0.4 cm.

The handle of the sampling device allows a human to manipulate the sampling device when taking sample from the sample source (such as the cervix). The handle is typically about 10 to about 25 cm long. The handle can be made of any material that is compatible with its intended use, for example, plastic, such as polypropylene, polyethylene, polycarbonate, polyimide, polyamide (e.g., nylon), PTFE (Teflon®), and polystyrene.

The handle may be detached from the rest of the sampling device by various ways. For example, the handle can be snapped away from the middle portion, cut off from the middle portion, or released from the rest of the sampling device by a built-in manually actuated release mechanism. In some embodiments, the handle and the middle portion are screwed together, and can be separated by screwing off the handle.

The vial cap ring can be attached to the vial before or after it is attached to the sampling device. In some embodiments, the vial cap ring is an integral part of the vial. Typically, the inner perimeter of the vial cap ring is the same as or slightly bigger than the outer perimeter of the middle portion of the device, so that upon attachment of the vial cap ring to the sampling device and removal of the handle, the vial cap ring and the middle portion of the sampling device form a closure that seals the vial.

The vial cap ring can be made of any material that is suitable for its intended purpose, for example, plastic, such as polypropylene, polyethylene, polycarbonate, polyimide, polyamide (e.g., nylon), PTFE (Teflon®), and polystyrene. In some embodiments, parts or the entire vial cap ring is pierceable.

The vial is used to receive the sampling head of the device and the sample. Typically, the vial has an internal diameter of about 2 to about 3 cm, and an internal depth of about 6 to about 7 cm. The vial typically has a volume of about 30 ml to about 35 ml, but other volumes may also be used. The vials as supplied can contain sample processing solutions such as preservation solutions, cell fixation agents, and/or cell permeabilization agents, before the sampling head is placed in the vial. In other embodiments, these solutions are added to the vial after the sampling head is placed in the vials. The solutions contained in the vial can be of any practically allowable volume. Typically, about 10-30 ml, such as about 15 to 20 ml of solution is contained in each vial.

The vials can be bar coded to facilitate the identification of the samples in the vials. The vials may further be notched so that they can be inserted into a vial rack (see below) in a specific orientation. This may ensure that the barcodes on the vials all face the same direction so that they can be automatically scanned.

The invention also provides methods of using the sampling device described herein to collect cell samples (such as cervical samples). The sampling device can be used in combination with the vial cap ring and the vial, or it can be used separately. Thus, in some embodiments, the method of using the sampling device includes a) collecting a cell sample from a sample source (such as a cervix) using the sampling device, b) rinsing the cells from the sampling device to a vial, and c) placing a vial cap having a pierceable top to the vial.

In some embodiments, the method of using the sampling device or the sample collection assembly includes: a) collecting a cell sample from a sample source (such as the cervix) using the sampling device, b) attaching the sampling device to a vial cap ring, c) placing the sampling device in the vial, and d) detaching the handle, so that the vial cap ring and the pierceable portion of the middle portion of the device form a closure that seals the vial. The method can further include rinsing the cervical cells from the sampling head and/or retrieving samples from the vial, for example by inserting a pipettor tip through the pierceable portion in the middle portion and the shaft of the sampling head and aspirating the sample out of the vial. The sample thus can be retrieved from the vial without opening the vial cap, which significantly reduces the risk of contamination. Furthermore, the pierceable portion of the middle portion of the sampling device may be resealable, which allows the vials to be sealed immediately after the sample has been aspirated from the vial.

The steps described in the methods can be carried out in various orders, and are not limited in terms of order. For example, the sampling head can be placed in the vial before the vial cap ring is attached. Similarly, the handle may be removed before a vial cap ring is attached to the device. Furthermore, depending on the particular sampling device used, two or more steps may be merged. For example, in some embodiments, the vial cap ring is an integral part of the vial. Attaching the sampling device to the vial cap ring thus might merge with the step of placing the sampling head in the vial.

Sample Processing

The sample can be processed in any of a variety of ways. For example, as described above, the sampling device can be rinsed into a tube containing a liquid preservation solution to thin the mucus and eliminate debris that can obscure the cells. The sample or an aliquot of the sample may be further processed (such as by passing the sample suspension through needles of 1.0, 0.8, and/or 0.65 mm inner diameter) to disaggregate cell clusters and prepare a single-cell suspension. The cell sample may be filtered (such as by a 60-100 µm pore-size mesh) to remove residual cell clusters and large debris. The sample can also be filtered (such as by a 5-20 µm pore-size mesh) to partially remove small debris, red blood cells, PMN, and inflammatory cells.

Cells in the cleaned single-cell suspension may be fixed and permeabilized before they are brought into contact with probing agents. Alternatively, cells can be stained with one or more probing agents before they are permeabilized and further stained with additional probing agents. For example, in some embodiments, one or more probing agents recognizing cell surface biomarkers are used. It may be possible to stain cells with those probing agents before cells are permeabilized. The cells may then be permeabilized and further stained with other probing agents, such as those that recognize biomarkers expressed in the cytoplasm or the nucleus.

Generally, any agent for fixing and/or permeablizing cells can be used, as long as it adequately preserves the cells of interest and it does not exhibit significant fluorescence at the emission wavelength of the fluorochrome or the autofluorescence. Suitable agents include, for example, 100% methanol, 4% paraformaldehyde followed with saporin detergent, 95% ethanol containing 2-5% poly-ethyleneglycol, PreservCyt (Cytyc Corp., Boxborough, Mass.), Cytorich (AutoCyt, Burlington, N.C.), and others known to those skilled in the art.

In some embodiments, the agents for fixation and/or permeabilization can be washed away from the cells before staining with probing agents proceeds. For example, after fixation, the cells can be sedimented to form a pellet and resuspended in a medium such as PBS. This process can be repeated several times if necessary.

In some embodiments, the cells are subject to a blocking step prior to staining to suppress non-specific binding and to increase the sensitivity of the signal. Numerous methods for blocking non-specific binding are known to those skilled in the art and are suitable. Exemplary blocking agents include a dilute (such as 2%) solution of a protein such as bovine serum albumin, casein, fetal bovine serum, and fish skin gelatin.

Methods of staining samples with probing agents are known in the art. Generally, the steps involve contacting the sample with one or more probing agents. In cases wherein the probing agents are not labeled prior to the contact, the sample can be further subject to a labeling step. The staining conditions (such as concentrations of various agents, temperature of the staining, etc.) are known in the art, and depend on the nature of the probing agents, the condition of the sample, and the biomarker to be detected. In some embodiments, the sample is pre-analyzed to determine the condition of the sample (e.g., how many cells are in the sample), and the staining condition can be adjusted accordingly. In some embodiments, the unbound probing agents are removed before the sample is further analyzed in a detecting instrument.

Negative and positive cervical specimen (as determined by the pathologist) can be used as controls to select and titrate the concentration of the probing agents. Probing agents and corresponding controls may be used to stain the negative and positive specimens. Fluorescent images or flow cytometry measurements of the negative and positive specimens stained by probing agents and corresponding isotype controls can be obtained. Probing agents that render distinguishing fluorescent activities between negative and positive specimens as well as between probing agent-stained and control-stained specimens can be selected. Optimal concentrations can be determined for each probing agent that maximally distinguishes between the negative and positive specimens.

In embodiments when more than one probing agent is used, the different probing agents may be added sequentially or simultaneously to the sample. In some embodiments, a mixture of probing agents (such as an antibody cocktail) is made. Optimal concentrations can first be determined for each probing agent individually, and the probing agents at optimal concentration can then be mixed together. The cocktail of probing agents can be evaluated the same away as described above. The staining result can be compared to the staining result of each individual probing agent to determine whether the probing agents in the cocktail function independently and do not interfere with one another. The sensitivity ad specificity of the staining can also be evaluated.

The reagents making up the cocktail can be provided as a pre-combined composition or can be combined before the staining (generally, but not necessarily just before staining). For example, in one embodiment, the cocktail can be provided as a single composition including each of the reagents. In other embodiments, some, but not all, of the probing agents are provided in a pre-mixed cocktail. In some embodiments, the cocktail can be provided as separate containers for each of reagent. Mixing of the reagents can be done right before the staining experiment, for example by a person or a machine such as a device described herein.

In some embodiments, a cocktail of probing agent comprising an anti-p16INK4a antibody and/or an anti-Mcm5 antibody is used for the staining. In some embodiments, the cocktail further comprises an anti-Cdc6 antibody. In various embodiments, the concentration of the p16INK4a antibody is any of about 0.1 to about 20 µg/ml, about 0.1 to about 10 µg/ml, about 0.1 to about 5 µg/ml, about 0.1 to about 3 µg/ml, about 0.1 to about 2 µg/ml, about 0.1 to about 1 µg/ml, about 0.1 to about 0.5 µg/ml, about 0.15 µg/ml, about 0.25 µg/ml, about 0.35 µg/ml, about 0.45 µg/ml, about 0.2 to about 20 µg/ml, about 0.5 to about 10 µg/ml, about 1 to about 10 µg/ml, about 2 to about 5 µg/ml, about 2 µg/ml, about 3 µg/ml, about 4 µg/ml, about 5 µg/ml. Other concentrations are also contemplated.

In various embodiments, the concentration of the Mcm5 antibody is any of about 0.1 to about 20 µg/ml, about 0.1 to about 10 µg/ml, about 0.1 to about 5 µg/ml, about 0.1 to about 3 µg/ml, about 0.1 to about 2 µg/ml, about 0.1 to about 1 µg/ml, about 0.1 to about 0.5 µg/ml, about 0.15 µg/ml, about 0.25 µg/ml, about 0.35 µg/ml, about 0.45 µg/ml, about 0.2 to about 20 µg/ml, about 0.5 to about 10 µg/ml, about 1 to about 10 µg/ml, about 2 to about 5 µg/ml, about 2 µg/ml, about 3 µg/ml, about 4 µg/ml, about 5 µg/ml. Other concentrations are also contemplated.

In some embodiments, one or more steps of sample process are carried out by using the automatic cervical cancer screening device described herein.

Autofluorescence

The methods and devices as described herein may comprise measurement of cellular autofluorescence. Molecules that give rise to autofluorescence include, but are not limited to, tryptophan, NAD(P)H, and flavins (including riboflavin, flavin mononucleotide (FMN), flavin adenine dinucleotide (FAD), and proteins bonded with FMN and FAD). The excitation/emission wavelengths of these three sources are 290 nm/330 nm, 350 nm/450 nm, and 450~490 nm/500~560 nm, respectively.

Autofluorescence may be used the same way as biomarkers are used for identifying precancerous or cancerous cells. For example, it has been observed that flavin fluorescence intensity increases in inflammatory, LSIL to HSIL cells. This could relate to an increase in cellular metabolism in precancerous or cancerous cervical cells. See, e.g., Pavlova et al., Photochem Photobiol, 77(5):550-5 (2003). Similarly, NAD(P)H can be used as quantitative fluorescent biomarkers for LSIL and HSIL. Georgakoudi et al., *Cancer Res.* 62, 682-687 (2002). Thus, in some embodiments, flavin fluorescence activity is measured. In some embodiments, NAD(P)H fluorescence activity is measured. These measurements are then subject to the multi-parameter data analysis to determine whether the cell is precancerous or cancerous.

In some embodiments, cellular autofluorescence may serve as a gating parameter to exclude non-cell particles or cell debris with relatively low or no autofluorescence and those with high autofluorescence. Autofluorescence may also be used to estimate the size and shape of the cell, which in turn is used to calculate the average fluorescent activity of each cell.

In some embodiments, autofluorescence is used to calibrate the fluorescent activities of the fluorescent labeled probing agents. Due to the broadband of autofluorescence, autofluorescence activities may spread into other channels dedicated to detecting probing agents and increase the background of those channels. This is particularly problematic when the fluorescent signal for the probing agent is relatively low. In some embodiments, a separate channel is dedicated to the measurement of cellular autofluorescence activity, and the measurement is used to estimate the amount of autofluorescence spread-over in other channels. For example, it was found that the flavin autofluorescence intensities in the FITC, PE, and APC bands are approximately linear. This linear relationship makes it possible to estimate the autofluorescence intensity in the PE and APC bands from the autofluorescence intensity in the FITC band. Thus, in one embodiment, the FITC band measures a cell's autofluorescence from its intrinsic fluorochrome flavins. The PE and APC bands are used to measure probing agents bound to biomarkers. The signals in the PE and APC bands can be calibrated using the autofluorescence intensity in the FITC band.

In some embodiments, autofluorescence is used for two or more purposes as indicated above.

Light Scattering

Morphology of cells has been the basis for traditional cervical cancer screening. Light scattering is known to be affected by the morphology of cells. The amount of light scattered at small angles (0.5° to 5°), also referred to forward light scattering, gives a rough measure of cell size. The amount of light scattered at large angles (15° to 150°), also referred to as side scattering, increases with the cells internal granularity, i.e., the nuclear size, the nuclear content, the number of organelles present in the cell, and the surface roughness.

The amount of near infrared light scattering correlates with the nuclear size of a cell. For example, Drezek et al. investigated the properties of near infrared light scattering of Feulgen-thionon stained cervical cells and found that scattering cross-section significantly increases as the grade of dysplasia increases. This was due to an increase in nuclear size, optical density, and texture in dysplasia. The increased size and elevated DNA content of nuclei in high-grade lesions causes significant changes in scattering intensity. Furthermore, the spatial dimensions of chromatin texture features and the amplitude of refractive index fluctuations within the nucleus impacted both the distribution of scattering angels and the total amount of scattered light. Drezek et al., J. Biomed. Opt, 8(1):7-16 (2003).

In some embodiments, light scattering is used to determine cellular morphology. In some embodiments, the methods and devices as described herein utilize forward side scattering, side light scattering, or both, with visible excitation to determine cellular morphology and differentiate cell types. In some embodiments, forward light scattering is measured. In some embodiments, side light scattering is measured. In some embodiments, both forward and side scattering are measured. In some embodiments, the light scattering parameters are used to estimate cell nucleus to cytoplasm ratio. For example, the side light scattering intensity relative to the cell size estimated by pulse width generated by the cell in a detector (such as a flow cytometer) can be used to estimate the cell nucleus to cytoplasm ratio and therefore provide information for distinguishing between normal and precancerous or cancerous cells. The side light scattering together with forward light scattering can also be used to estimate the nucleus to cytoplasm ratio.

In some embodiments, near infrared light scattering is measured. Such near infrared light scattering can be either near infrared forward light scattering or near infrared side light scattering, or both. In some embodiments, near infrared light scattering is measured together with visible forward light scattering to determine both the size of the nucleus and the size of the cell. In some embodiments, near infrared light scattering is measured together with both visible forward light scattering and visible side light scattering.

The light scattering measurements provide information about cell morphology, which, in combination with information about fluorescent activities of the cell, can lead to the identification of precancerous or cancerous cells. For example, in some embodiments, the nucleus to cytoplasm ratio can be estimated, and a high nuclear/cytoplasm ratio indicates more advanced dysplasia.

The light scattering measurements (such as light scattering intensities) and/or nuclear/cytoplasm ratios can also be used as gating parameters to exclude non-cell particles or cell debris. The gating threshold can be based on absolute values and/or nucleus/cytoplasm ratios.

The morphology information obtained through the measurement can also be used to calculate average fluorescence intensity of the labeled biomarkers.

Detection of Multiple Parameters

Detection may be carried out by any method that can measure (or determine the presence or absence of) a given parameter. In some embodiments, the detection instrument for detecting multiple parameters comprises a flow cytometer. In some embodiments, the detection instrument for detecting multiple parameters is part of a cell screening apparatus described herein.

In some embodiments, the flow cytometer or the cell screening apparatus is equipped with a single laser to excite the fluorescent activities of the cells. The fluorescent label for the biomarkers and/or the autofluorescence therefore must be excitable at a single wavelength. In other embodiments, the flow cytometer is equipped with more than one laser, and the fluorescent labels may be excited at different wavelengths. For example, the flow cytometer may comprise a solid state laser at 488 nm, which provides the excitation for visible scattering and three fluorochromes in the FITC, PE, and PerCP band. It may further comprise an air-cooled HeNe laser around 633 nm, which provides the excitation for near-infrared scattering as well as the fluorochrome such as APC. The flow cytometer used herein may have additional cell sorting function, but cell sorting is not essential for the detector.

During data acquisition, the flow rate is typically set at a constant rate to ensure a consistent measurement. For each cell passing through a laser beam in a flow cytometer, a pulse-like signal is generated in the detector corresponding to each parameter. The pulse starting time can be used to register the multi-parameter channels. Multiple features (such as height, area, and width) can be measured on the pulse to quantify the parameter. The pulse height and area measure the peak intensity and total intensity of the parameter, respectively. The pulse width measures the duration of the cell that passes through the laser beam. This duration is related to the cell size, the flow rate, and the height of the laser beam. The pulse width can also be used to reject erroneous measurements such as non-cell debris or cell clusters (overlap of two or more cells). For example, the typical size of epithelial cells in cervical specimens ranges from about 15 to about 60 µm.

Particles that fall outside of the range may be non-cell debris or cell clusters and thus can be rejected.

When laser beam dimension along the axis of flow is larger than a cell diameter, the peak intensity should be proportional to the total scattering of fluorescence intensity. When laser beam dimension is smaller, the average pulse height has a better estimation of the average scattering or fluorescence intensity, and is thus more preferred.

The sensitivity and accuracy of the flow cytometry measurement can be determined in a spiking experiment. Unstained negative or positive cervical specimens can be spiked (added) by biomarker-positive cervical cancer cells (such as HeLa or Ca Ski cells). Cervical cancer cells with different numbers (such as different dilutions from a single cell stock) are added to unstained cervical specimens. The sensitivity of the flow cytometry measurement is determined by the minimum number of cancer cells that can be detected. The accuracy of the flow cytometry measurement can be determined by the number of cancer cells detected relative to the number of cancer cells spiked.

The flow cytometer can be calibrated prior to its use. In this section, a calibration procedure for the BD FACSAris flow cytometer is described, which can be easily adapted for any other flow cytometers. The fluid levels of the flow cytometer are first inspected, then the sheath flow is started. The 488 nm (blue) and 633 nm (red) lasers will be turned on and given 30 minutes to warm up. Before data acquisition, CaliBRIGHT beads or equivalent can be used as quality control (QC) samples to optimize the photomultiplier tube (PMT) voltages, the laser delays and the area-scaling values. The QC sample will include unlabeled, FITC labeled, PE labeled, and APC labeled micro beads. The calibration procedure is briefly described as follows. First, set the BD FACSDiVa software to display one dot plot of FCS versus SSC and six histograms of FITC-H, FITC-A, PE-H, PE-A, APC-H, and APC-A, respectively (-H indicates pulse height measurement; -A indicates pulse area measurement). Second, start the sample injection and set the flow rate to the lowest possible rate (1.0). All the data will be acquired in linear mode. Third, adjust the FSC and SSC voltages to appropriately display the scatter that is suitable for cervical specimens. Fourth, adjust the FITC, PE, and APC PMT voltages to place the mean of the pulse height signals at approximately $100 \times 10^3$ (on a linear scale between $0-260 \times 10^3$) on the histogram. Adjust the area-scaling coefficient to place the mean of the area signals also near $100 \times 10^3$. The spread of the signals indicates the coefficient of variation (CV) of each fluorescence band. Fifth, adjust the red laser delay setting to obtain the highest mean channel for the APC signal. Sixth, establish the fluorescence compensations using control samples such as the COMP beads (BD Science). To minimize the day-to-day variations, the calibration procedures will be performed before each experiment to ensure the data is acquired under the same conditions.

Data Analysis

The data obtained from detection (such as by a detection instrument) can be displayed and visually analyzed. For example, for each selected parameter, such as a fluorescence intensity of a biomarker, a monoparametric histogram can be used to show the selected parameter on the x axis and the relative cell number on the y axis. Similarly, measurements of two parameters can be shown in a biparametric histogram (such as a dot plot or a density plot), which shows cells distributed as a function of their signal intensity with respect to each parameter. Cells located in the upper left quadrant are positive for the parameter represented in the y axis, cells located in the upper right quadrant are positive for both parameters, cells located in the lower left quadrant are positive for the parameter represented in the y axis, cells located in the lower left quadrant are double negative, while cells located in the lower right panel are positive for the parameters on the x axis. Similarly, measurements for three parameters can be shown in a three-dimensional representation, wherein the z axis can represent a third parameter.

The data can also be further processed to integrate multiple parameters obtained from the multi-parameter analysis into one or a set of values for each cell analyzed. In one embodiment, principal component analysis can be used to linearly combine multiple parameters to one or more independent principal components. These principal components reproduce the largest variance among the data and therefore have the potential to separate normal and precancerous or cancerous cells. An analysis of the principal components often reveals relationships that are not observed in single parameter. Furthermore, factor analysis, correlation analysis, linear and nonlinear multiple regression analysis are all multivariate analysis tools that can be used herein for data analysis.

After each analyzed cell in cervical sample is assigned one or a set of numeric (or Boolean) value(s), the cells can (but not necessarily) be classified as "normal" or "precancerous or cancerous." In some embodiments, the cells are further classified into different levels of dysplasia. Discrimination functions can be established using methods known in the art.

A cell can be classified by comparing the value(s) assigned to the cell to a predetermined threshold or a set of thresholds. For example, when two biomarkers are used simultaneously in the analysis, two cut-off thresholds for the two biomarkers will be moved along the two axes on of a biparametric histogram. If the stain intensities of a cell for both biomarkers exceed the thresholds, then the cell will be classified as precancerous or cancerous cells. In other embodiments, the threshold is based on the collective information on multiple parameters. For example, each cell may be assigned a single value obtained by the integration of multiple parameters, and the value can be compared with a single threshold value to determine whether the cell is normal or precancerous or cancerous (or different levels of dysplasia). Thresholds are typically, but not always, determined empirically, for example by using pre-classified cervical samples.

Once cells in a sample have been analyzed, the sample can be classified as positive or negative. The number of cells to be analyzed before a classification of the sample can be obtained depends on the condition of the subject, the parameters analyzed, the probing agents used (if any), and other factors. Typically, the classification of the sample can be based on the analysis of more than about 50,000 cells, such as any of more than about 100,000 cells, about 200,000 cells, about 300,000 cells, about 400,000 cells, or about 500,000 cells.

One method of sample classification depends on the number cells in the sample that are determined to be precancerous or cancerous. For example, the identification of one (or some other predetermined number of) precancerous or cancerous cells in a sample may be sufficient to cause the sample to be classified as being positive. In some embodiments, a sample is classified as positive if about 10, about 15, about 20, about 25, or about 30 cells (out of an average of about 50,000-100,000 cells) are detected as precancerous or cancerous cells.

Another method is to look at the statistical distribution of all the cells in a sample and compare the distribution of the cells with that of positive and negative samples. A statistical difference in the distribution (such as means and variance distributions of the sample) from a negative sample would indicate that the sample is positive. In some embodiments, the classification is determined empirically through sample training.

In some embodiments, it is initially assumed that every sample is positive and then to reclassify as negative only those samples that contain little or no precancerous or cancerous cells. This "select out" approach ensures that even borderline cases are identified for further evaluation. Procedural controls can be included to ensure that the sample preparation, staining and data capture have been performed correctly and that the data meet certain minimum criteria of acceptability.

In some embodiments, cells analyzed as above are further sorted, for example, using a cell sorter built into the device described herein or a fluorescent activated cell sorter. Cells that are determined to be precancerous or cancerous can be isolated accordingly and directly subject to further analysis. For example, the isolated precancerous or cancerous cells can be loaded onto a microscopic slide and analyzed using routine cytological methods.

Evaluation of the Discrimination Power of the Methods

With the change of different cut-off thresholds, the classifications as well as the sensitivity and specificity of "positive" sample discriminations will be changed. A good tool to evaluate the discrimination power of these methods is to use the Receiver Operating Characteristics (ROC) curve.

For each cut-off threshold, the true positives, true negatives, false positives, and false negatives can be identified using the cytopathologist's classification as the reference. There will be reference positive cases correctly classified as "positive" by the test (True Positive or TP). However, some reference positive cases may be classified as "negative" by the test (false negative or FN). On the other hand, some reference negative cases may be classified as "negative" by the test (true negative or TN), but some reference negative cases may be classified as "positive" by the test (false positive or FP). The sensitivity and specificity of a test at a specific cut-off threshold can be calculated as Sensitivity=TP/(TP+FN); Specificity=TN/(TN+FP). The sensitivity and specificity of a test change with the cut-off threshold.

ROC curves represent the trade-off between the sensitivity and specificity values at different cut-off thresholds. It is constructed by all the possible sensitivity and specificity values as illustrated in FIG. 1. An important property of the ROC curve is that the greater the overlap between the two test results, the closer the ROC curve is to the diagonal line, which results in a smaller area under the ROC curve. In this case the discriminating power of the test is also worse. In other words, the ROC curve and the area under the curve is a good measure of the discriminating power of the diagnostic test. Usually, if the area under the ROC curve is between 0.9-1, it is an excellent test; between 0.8-0.9, it is a very good test; between 0.7-0.8, it is a good test; between 0.6-0.7, it is a fair test; and between 0.5-0.6, it is a poor test.

As will be apparent by people skilled in the art, the larger the number of samples, the smaller the standard error in ROC curves. Thus, for example, when 30 negative and 30 positive samples are involved in a test, and the area under the ROC curve is measured to be 0.9, then the standard error will be less than 5%.

Once a ROC curve has been established for the method, a threshold value can be chosen based on the desired sensitivity and specificity. For example, in some embodiments, high sensitivity is preferred. In those embodiments, a sensitivity of about 85% to about 99% may be desired. In some embodiments, specificity is a priori to sensitivity. In those embodiments, a specificity of about 80% to about 95% specificity may be desired.

B. Automated Cell Screening Apparatus

There is also provided a cell screening apparatus in which a sample of cells (e.g. a cell sample taken from a patient) is prepared (including, in some embodiments staining) and analyzed by the apparatus. The apparatus gives a report indicating numerical results or histograms and/or that the sample is "positive" (such as having threshold number of abnormal cells) or "negative" (such as having below threshold level of abnormal cells). The cells need not be cervical, and the screening need not even be for cancer or precancerous or cancerous cells. Examples of other types of cancerous cells to be screened include (not limiting) skin (melanoma), oral, bladder, and lung. Cervical cells are described as exemplary cells below. Labeling using antibodies is also described as exemplary.

The report from the apparatus may further guide the physician or cytotechnologist in determining patient treatment. For example, cell samples that are classified "negative" can be reported and generally do not require a pathologist to inspect the sample again. The samples that are classified "positive" are then subject to conventional cytology examination by a pathologist for reflex or confirmatory testing. The quantitative results from the apparatus for "positive" samples may assist the pathologist in this testing to analyze the degree of abnormality.

Figure 15:
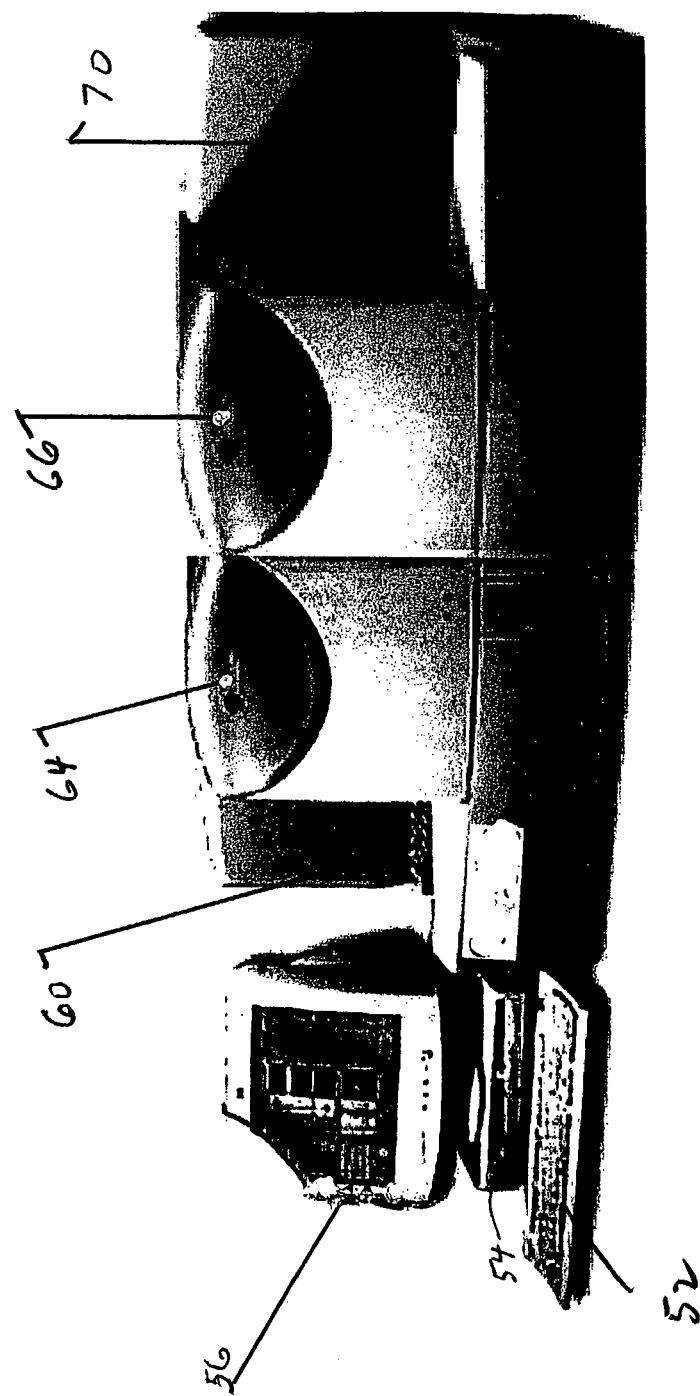
FIG. 15 shows an overview of an apparatus for detecting cell abnormalities as disclosed herein.

In one example described herein, the apparatus utilizes flow cytometry. FIG. 15 shows such an apparatus for cervical cancer screening adapted to carry out methods in accordance with this disclosure for cell screening and analysis. This apparatus is not limited to cervical cancer screening or to cancer screening, but is generally suitable for cell analysis. As shown in FIG. 15, the apparatus is a largely conventional instrumentation arrangement suitable for location, for instance, on a tabletop and includes largely conventional subsystems and components of the type generally commercially available.

The system includes, at the far left side, a standard personal computer system shown here to be a desktop type computer including a keyboard 52, central processing unit (CPU) 54 and monitor 56. The computer system itself is conventional and the software running thereon to support operation of the apparatus of FIG. 15 is readily coded in accordance with the following disclosure by one of ordinary skill in the art of instrumentation. The computer system including components 52, 54 and 56 performs the data management function and data analysis as further described herein. The computer system is the primary interface with the apparatus operator. The computer is also linked to the LIS (Laboratory Information System) to download work orders and upload final results. Post analytical unit manages sample vials after they have been processed and physically separates them into two groups 1) negative samples and 2) positive samples which will be used for confirmatory testing. The computer system is operatively connected by conventional means to the remainder of the apparatus which includes, in terms of subsystems, a sample loader 60, pre-analytical unit 64, analytical unit 66, and post-analytical sample management unit 70.

The various associated drive mechanisms, sample and reagent and vacuum tubing, etc, for the FIG. 15 apparatus all of which are conventional, are not shown for simplicity. Various servo motors and drive motors are used to drive the components, and all of these are conventional and of the type used in medical and other instrumentation for testing small size liquid samples. Also provided is a standard pneumatic unit for applying air pressure/vacuum for aspirating and dispensing fluids as typical in medical instrumentation. The pneumatic unit is coupled to the various portions of the system to supply the required pressure/vacuum by a conventional network of tubing not shown. Typically, the computer system is coupled to the operative portions of the apparatus by a serial data link, using for instance, a high-level data link protocol, such as, but not limited to, RS232 serial link, USB, Can-bus, and LAN. The system conventionally includes its own power supply, transducers, solutions reservoirs, fluidic systems, and electronics as is typical of medical instrumentation. Typically, a microprocessor(s) or microcomputer(s) is provided embedded in the system for control purposes, in addition to the computer system 52, 54, 56. The pneumatic unit is typically coupled via a serial data link to the microprocessor/microcontroller, which in turn is coupled to the CPU 54. The computer system 52, 54, 56 portion typically includes a microprocessor, display, disk drives, hard disk drive, a pointing device, and local area network connection and conventional memory and associated software.

The CPU 54 and/or other embedded microprocessor or microcontroller in the apparatus provide an operator interface, control the mechanical system including all physical parts movements and the electronic system, including the firmware for instance for controlling the cell staining process. Also the onboard fluidic systems are controlled in the same way including sample movement and solutions and additions. Environmental factors such as temperature and humidity may also be controlled. Biological waste management is also included for the waste products. Also included is a power supply for the apparatus.

Generally in terms of ambient conditions, the inside temperature and humidity of the apparatus of FIG. 15 are controlled but the apparatus is typically not hermetically sealed, although of course care is taken to prevent any contamination from entering into the samples at any stage.

Figure 16:
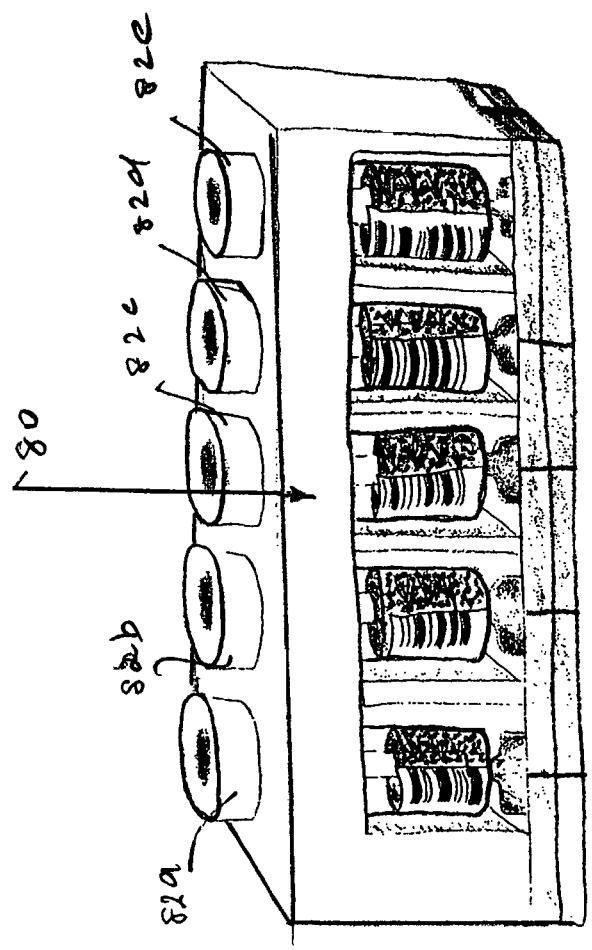
FIG. 16 shows a sample rack holding a number of sample vials of the type shown in FIG. 15.

The samples of cells (such as cervical cells) which have been collected using the technique(s) as described above, or a conventional technique for cell collection, are loaded with one sample per sample vial into a sample vial rack 80 as in FIG. 16, which in this case holds five sample vials 82*a*-82*e*, of the type described above or similar. The sample vial rack 80 is of any convenient size to hold one or more vials. The particular number of vials held is not limiting. The sample vial rack is made of any convenient material, such as rigid plastic. Typically the sample vials are manually loaded into the sample rack by the operator of the apparatus. The patient identification and other relevant information may be manually entered into the computer system by the operator. The work-order (individual order for a patient) which is part of the work list (all work-orders for the to-be processed batch) consists of patient/sample identification and some additional work-order related information such as "urgent" will either be downloaded from the LIS or entered manually by the operator. At the time when the sample is processed this information is in the computer system memory of the apparatus. Then the barcode scanner scans the barcode and checks if the work-order for this sample is in the computer memory. If yes, the sample is being processed, if no the sample will be flagged and without processing being put back into the queue.

Figure 17:
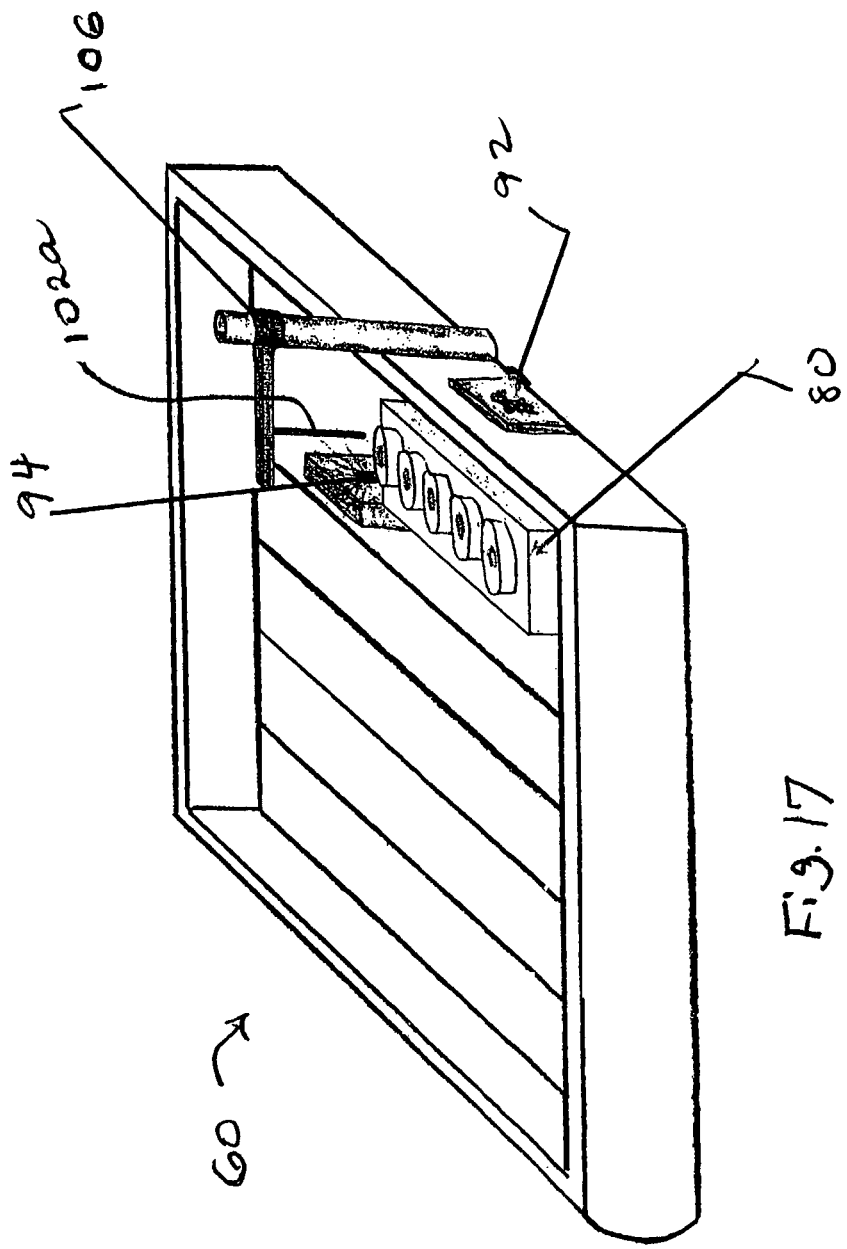
FIG. 17 shows a sample rack of the type shown in FIG. 16 loaded into a sample loader for use with the apparatus of FIG. 15.

As shown in FIG. 17, the sample vial rack 80 is loaded into sample loader 60, which is a relatively large rigid chassis or framework made of any convenient material such as plastic or metal. As shown in FIG. 17, the sample loader 60 accommodates from one to, for instance, 12 sample vial racks. Typically, guides are provided on the bottom inner surface of the sample loader 60 to guide the sample vial racks and hold them in a proper position. The sample loader 60 is also provided with a mixer 92, which is, for instance, a conventional vortex mixer of the type conventionally available. The sample may also be mixed by repetitive aspiration/dispension.

Also provided mounted on the sample loader 60 is a conventional bar code scanner 94 for scanning the bar codes typically present on the outside of each sample vial, and a conventional sample pipettor (aspirator) 106 for aspirating the samples from the vials. In other embodiments no sample loader is provided and the sample vials are individually placed manually in a single vial closed sampler. A closed sampler is a component that is mounted to the apparatus and holds a single sample vial in a fixed position. The operator places the vials individually into the closed sampler. A vortex mixer can be part of the closed sampler to provide equal cell suspension. In this position the pipettor 106 will pierce the vial cap and aspirate the sample. After that the operator removes the sample and loads the next sample vial manually. In this configuration a barcode scanner can be incorporated into the closed sampler or the operator uses a handheld barcode scanner that is coupled to the computer system and scans the sample vial bar code before it is placed into the closed sampler. This results in a simpler apparatus, but with somewhat less capacity and processing capability. An alternate to the fixed bar code scanner 94 thus is a hand-held bar code scanner used by the operator.

Typically the sample loader 60 is also coupled to the associated computer system so as to download a work list, for instance, via the LIS interface to provide a patient work list associated with each of the samples. The LIS as mentioned above (Laboratory Information System) conventionally manages all clinical laboratory work. All the sample and information management remains on the computer system memory of the apparatus. The computer system is interfaced to the LIS. To create a work-list it is either downloaded from the LIS or it is entered manually at the computer system of the apparatus. Firmware for operation of the sample loader resides in the microprocessor/microcontroller associated with the sample loader. The sample loader is not individually or directly linked to the computer system of the apparatus. Alternatively, this work list is entered manually into the computer system.

Typically a conventional conveyor system (not shown) moves the sample vial rack 80 from its position in the sample loader 60 to aspirator 106 to aspirate the sample from each sample vial for further processing. The vertical tip 102*a* of pipettor 106 penetrates the pierceable portion of the vial cap. Typically only approximately half of each sample is aspirated at this step in order to reserve the remainder for later reprocessing or offline testing if needed. A typical sample volume is 15 to 20 ml total, of which approximately 7.5 ml to 10 ml is subject to testing by the apparatus. These sample volumes are merely illustrative. The pipettor 106 aspirates and dispenses all or, as indicated above, a portion of each sample, in and out of the sample vial until an equal suspension of the cells and obscuring factors in the sample is achieved. At that point all of the sample is fully dispensed in the vial. This step may also be accomplished by the vortex mixer 92 or shared between the vortex mixer 92 and aspirator 106. The aspirator 106 then aspirates about half the sample from the vial as described above, and transfers it to the adjacent pre-analytical unit 64. As an alternative, a closed sampler aspirates the sample and transfers it to the pre-analytical unit 64.

Figure 18:
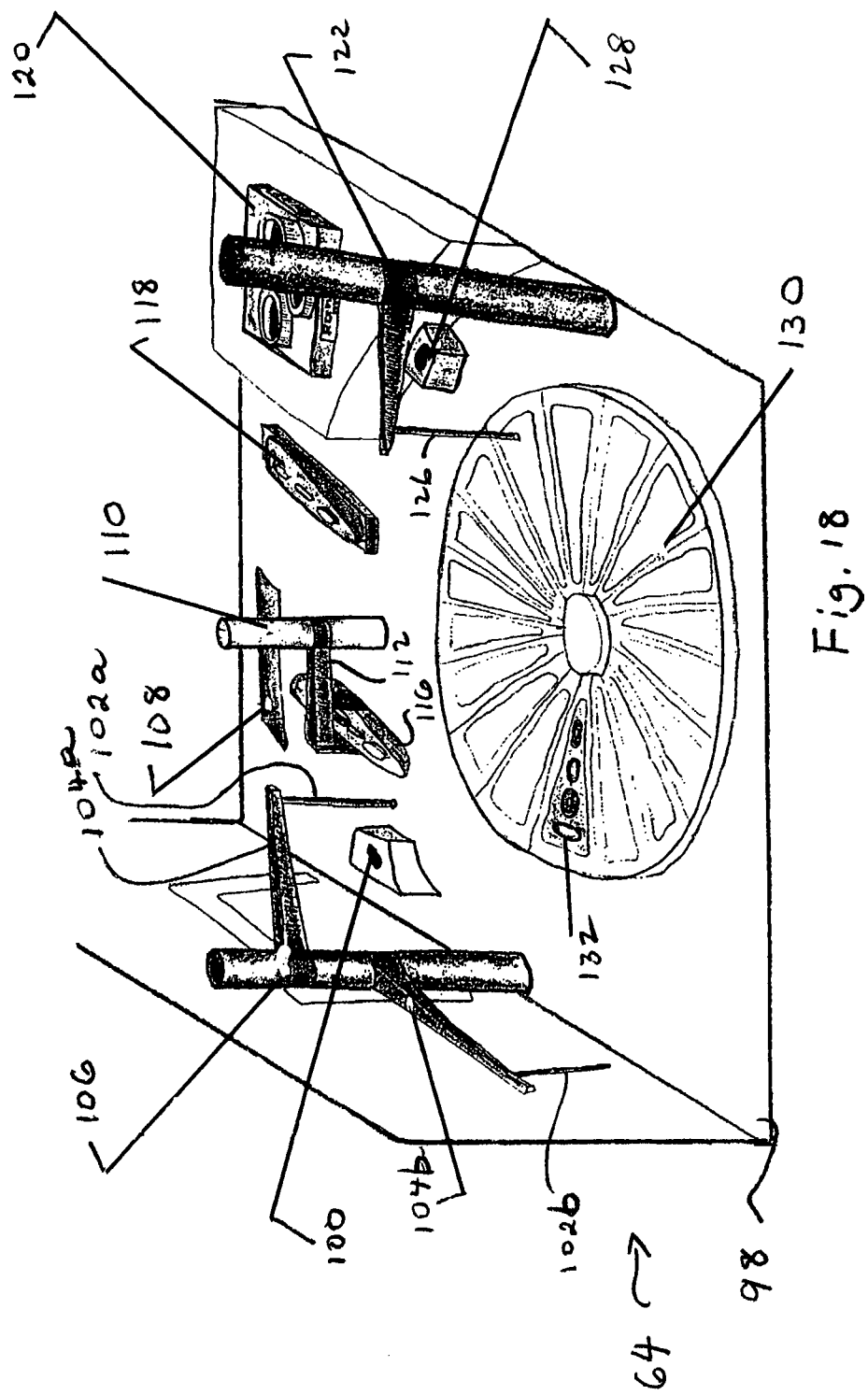
FIG. 18 shows the pre-analytical unit for sample pre-treatment and staining in with the apparatus of FIG. 15.

Further operation of the apparatus occurs in the pre-analytical unit 64, the internal mechanism of which is shown (without its housing) in FIG. 18. Pre-analytical unit 64 includes chassis 98 on which is mounted a first wash station 100, the first pipettor 106 with pipettor tip 102*a* and needle syringe 102*b*, supported respectively on arms 104*a*, 104*b*, and both connected to pipettor 106 by suitable internal fluid channels. (Pipettor 106 is shared between the sample loader and pre-analytical unit and may be mounted on either.) Arms 104*a*, 104*b* horizontally pivot on pipettor 106, and also move vertically on pipettor 106 as described further herein. Reaction cartridge disposal slot 108 is adjacent to a robotic pick and place shaft 110 on which is mounted a robotic arm 112, which is capable of grasping a reaction cartridge 116. The reaction cartridges 116 (also referred to as sample cup units) are dispensed from a dispenser 118, which accepts a magazine of same. (Only one of the reaction cartridges is shown in the dispenser 118 and this is the top most one in the dispenser.) Adjacent to dispenser 118 is a conventional reagent pack 120 including several containers of suitable reagents and solutions of the types described above. Adjacent is a second pipettor 122 with an associated arm and vertical tip 126. Adjacent to pipettor 122 is a second wash station 128. Both of the pipettors have arms that swing on a pivot and move vertically. The pipettor tip (the vertical part that enters into the liquids), thereby pivots forth and back on the horizontal arm of the pipettor and thereby reaches the individual chambers of the reaction cartridge, the individual reagent containers and the wash stations.

In the central portion of the chassis 98 is mounted a rotatable reaction cartridge carousel 130 having a number of roughly wedge-shaped slots, each of which accommodates one reaction cartridge 132. Only one such cartridge is shown for simplicity. However, typically, there would be a reaction cartridge in each of the slots in carousel 130. The carousel 130 is rotatably driven by a suitable motor, e.g., a stepper motor. Mechanisms such as shown in FIG. 18 are known in the medical instrumentation field for handling of large number of samples.

Figure 19:
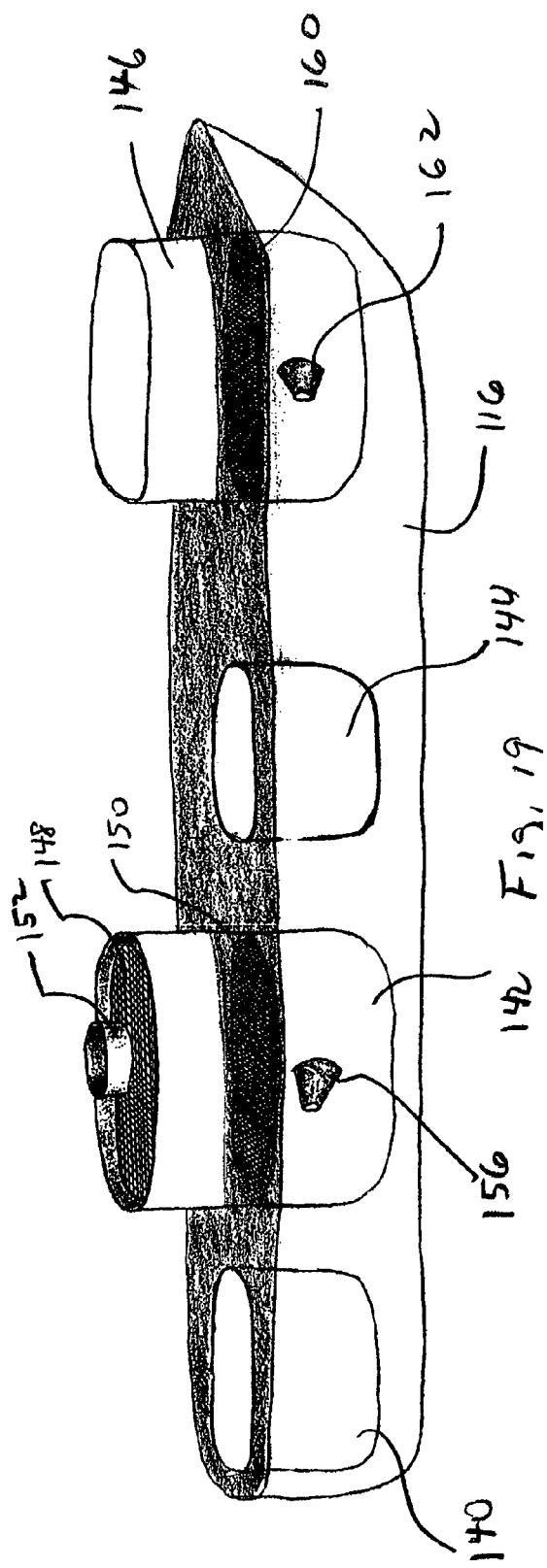
FIG. 19 shows a reaction cartridge of the type shown in FIG. 18 including four chambers.

Operation of the preanalytical unit of FIG. 18 employs the reaction cartridge, several of which are shown in FIG. 18 at for instance 116 and 132. Detail of a reaction cartridge 116 (or 132) is shown in FIG. 19. Typically the reaction cartridge is a molded plastic structure approximately 4 to 10 centimeters long and 1 to 3 centimeters wide and 1.5 to 5 centimeters high. It is made of any suitable rigid plastic, or glass or other material suitable to hold cellular samples. The body of the reaction cartridge is typically made by plastic molding and/or extrusion. The body (member) of the reaction cartridge 116 defines four chambers (sample cups) respectively, 140, 142, 144 and 146. The second chamber 142 includes two small pore filters 148, 150 each located transversely in the chamber. Port 152 extends vertically through the uppermost filter 148. A vacuum nozzle 156 is provided in the lower portion of the second chamber 142.

The fourth chamber 146 includes also a transverse small pore filter 160 and a vacuum nozzle 162. All the sample pretreatment and staining processes are performed in the various chambers in the reaction cartridge as disclosed following. Operation of the FIG. 18 unit is depicted in the following figures, each of which depicts a cutaway portion of the reaction cartridge 116 of FIG. 19, showing only the relevant portions in somewhat enlarged form. The structures shown in FIGS. 20-25 are those shown in FIGS. 18 and 19 and carry similar reference numbers.

Figure 20:
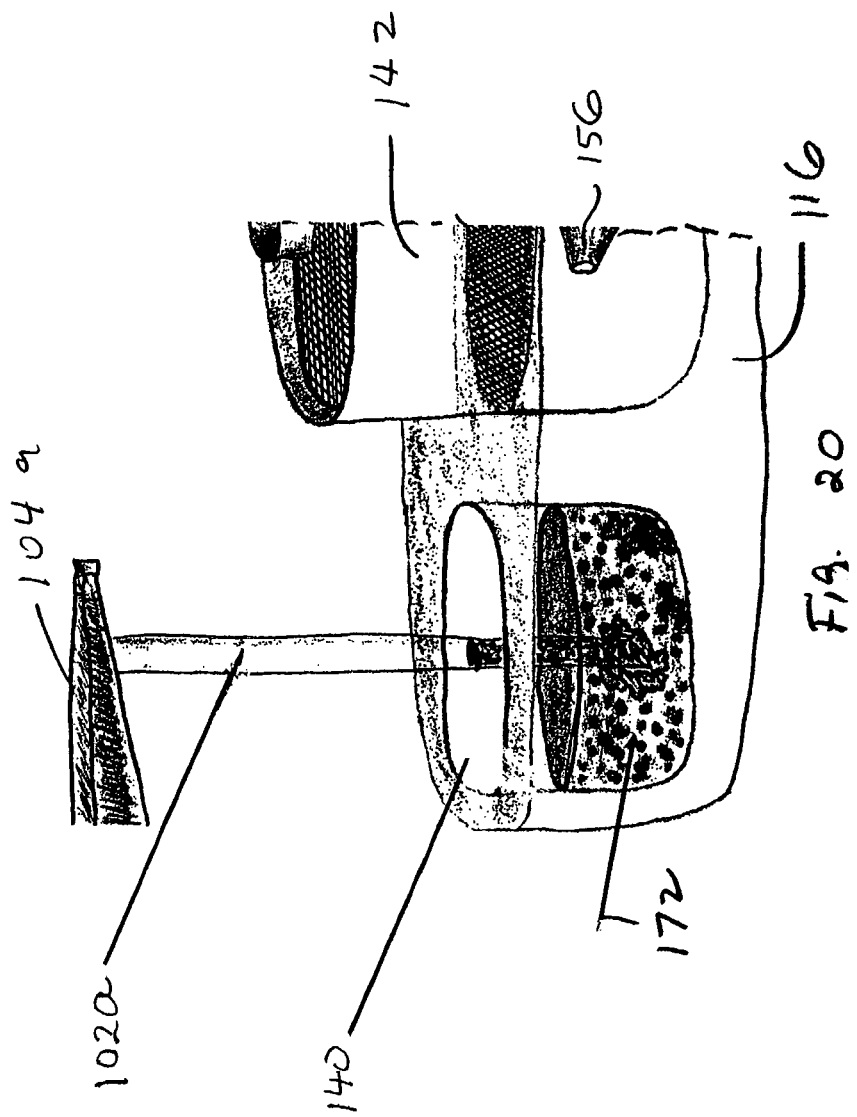
FIG. 20 shows cell cluster disaggregation performed using the reaction cartridge of FIG. 19 in the apparatus of FIG. 15.

First, robot arm 112 as shown in FIG. 18 picks up a reaction cartridge from the dispenser 118 and places it into the carousel 130 as shown by reaction cartridge 132. One reaction cartridge is provided for each sample to be tested, to avoid contamination between samples. The reaction cartridges are intended to be disposable medical testing items. The sample loader 60 of FIG. 15 includes the aspirator 106 which aspirates a sample from the sample vial via its pipettor tip 102*a* and transfers the sample to the preanalytical unit 64 as disclosed above. The fluidic system (not shown) then, after the pipettor tip 102*a* pivots into position, dispenses the sample through pipettor tip 102*a* into the first chamber 140 of the reaction cartridge 116, as shown in FIG. 20 which has been rotated into position by its supporting carousel 130. Thus in FIG. 20, the cervical cells, obscuring factors, cell clusters which form the sample 172 to be tested are dispensed into the first chamber 140. Note that during this time the cartridge 116 is in its slot in carousel 130. An alternative device to carousel 130 may be used to hold and move the reaction cartridges, as known in the field. After this aspiration, the pipettor tip 102*a* is pivoted to the orifice of wash station 100 to rinse out tip 102*a* conventionally using wash solution before the next sample is aspirated. (An alternative to the use of the wash station is use of disposable pipettor tips.)

Next, in one embodiment the cell clusters in the sample 172 are disaggregated using the needle syringe 102*b*. For instance, the needle syringe 102*b* may pivot and move into chamber 140 and aspirate/dispense the sample multiple times into and out of chamber 140 for disaggregation purposes. Alternatively, this disaggregation may be accomplished by mechanical agitation or addition of a suitable chemical solution.

Figure 21:
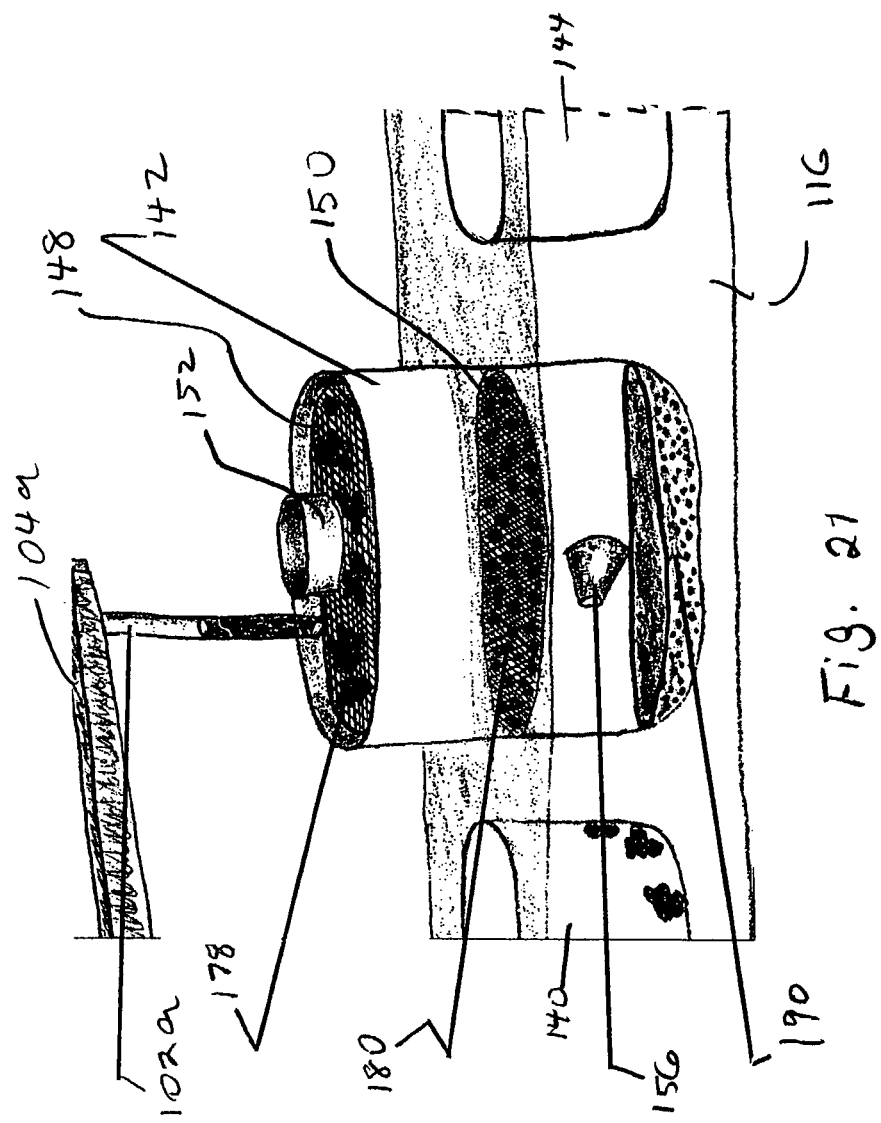
FIG. 21 shows the elimination of obscuring factors using a double filtered chamber in the reaction cartridge of FIG. 19.

Next, the needle syringe 102*b* is pivoted to and washed at wash station 100. The disaggregated sample 172 is then transferred, using pipettor tip 102*a*, from first chamber 140 to the upper part of the second chamber 142 as shown in FIG. 21. Then the pipettor tip 102*a* is pivoted to and washed at wash station 100. In another embodiment, the second chamber may be combined with the first chamber but there may be an alternative location for eliminating the obscuring factors. As shown in FIG. 21, the sample is dispensed onto the upper filter 148 in the second chamber 142. The second chamber is a double filter chamber, defined by upper filter 148 and lower filter 150. The second chamber 142 filters the sample 172 so the material in the sample which is larger than the desired single cervical cells to be screened remains as a residue 178 (to be disposed of) on the upper filter 148. Hence, the upper filter 148 has larger pores than the lower filter 150. A typical range of pore sizes for upper filter 148 is 60 to 100 μm and a typical range of pore sizes for lower filter 150 is 5 to 20 μm. These ranges are for cervical cells. Of course, the filter pore sizes are dependent upon the size of the cells to be tested. The filters can be made of a variety of materials, including different polymers such as nylon mesh, poretic polycarbonate films (such as those from Osmonic Inc.).

Double filter chamber 142 eliminates obscuring factors and allows one to obtain, for further testing, clean individual cervical cells. The larger residue particles 178 remaining on the upper filter 148 are to be disposed of. The desired single cervical cells 180 pass through the upper filter 148 onto the lower filter 150. Passage of the debris, red blood cells, PMNs generally pass through both filters, which is enhanced by vacuum (suction) supplied at vacuum nozzle 156 located in the lower portion of the second chamber 142 and coupled to the pneumatic unit of the apparatus. Alternatively, the entire filter process may be done offline prior to the sample being provided to the apparatus and a clean cervical cell sample being loaded into the sample loader. In this case the FIG. 21 filtering is not required. The obscuring factors 190 typically are red blood cells which are smaller than the single cervical cells and hence the lower filter 150 traps the cervical cells 180 thereon with the undesired obscuring factors 190 passing through to the lower portion of the second chamber 142 under the influence of the vacuum from the nozzle 156. The cervical cells remain as a supernatant on the lower filter 150 with smaller obscuring factors 190 and fluid passing through for later disposal.

After the vacuum supplied to the vacuum nozzle 156 is shut off, air flow is provided through nozzle 156 to close the vacuum nozzle and thereby close second chamber 142. A permeabilization solution (supplied from suitable reservoirs or bottles, similar to the other solutions) is added by the first pipettor 106 to the second chamber as shown in FIG. 22 with the pipettor tip 102a passing through the opening (port) 152 in the upper filter. This solution is added to the cervical cells 180 to permeabilize the cytoplasm and nucleus membrane of the cervical cells for subsequent staining. This permeabilization step may be omitted if the fixation carried out during the manual pretreatment of the cells (prior to entering into the apparatus) is deemed sufficient. Next, the pipettor 106 and tip 102a internal passages are washed at the first wash station 100 by pivoting the pipettor tip 102a to the wash station 100 and washing same.

At this point, vacuum is applied via vacuum nozzle 156 to eliminate the permeablizing solution from the lower part of chamber 142. A wash solution is added to chamber 142 via the pipettor tip 102a to chamber 142 to thoroughly wash the cells until the fixation solution is completely rinsed off. This washing/rinsing alternatively is performed by other means, such as an onboard centrifuge. This step cleans the cervical cells 180 of the permeabilization and fixation solutions.

Next the cervical cells 180 are suspended by adding a diluent thereto. With the vacuum off, air flows through the nozzle 156 to close up the chamber 142. Approximately 100 microliter of staining buffer or appropriate isotonic diluent (of the type described above) is added through pipettor tip 102a which still extends through the port 152 as shown. This diluent puts the cervical cells in suspension. Typically, the diluent is aspirated and dispensed multiple times in and out of pipettor tip 102a to properly dispense the cervical cells. Air pressure from nozzle 156 may aid in the cell suspension process. Alternatively, this suspension could be performed using the onboard centrifuge optionally installed as part of the apparatus, not shown or by ultrasonic energy. This completes the preanalytical processing to re-suspend the cervical cells.

Next is the preanalytical processing which accomplishes cell staining if staining is required. In this step the cervical cell suspension 192 is transferred to the third chamber 144, see FIG. 23(a). Sample 192, now in suspension, is dispensed into the third chamber 144 via the pipettor 106 and its tip 102a. Note that in other embodiments, rather than using an additional chamber this step could take place within the first, second, or fourth (146) chambers. The pipettor tip 102a is then pivoted to the wash station 100 and washed out as before. At this point, the cell density measurement is taken. This is also referred to as a cell density measurement. The cell density is measured to determine the amount of reagents used (the fewer cells the less antibodies are used for the incubation, hence less reagent is pipetted into the third chamber after the density measurement). In one embodiment, to measure the cell density, a small portion such as less than 10% of the volume of the cell suspension 192 is aspirated by the second pipettor 122 via its tip 126 (shown in FIG. 18) out of chamber 144 and injected into the flow cell in the analytical unit 66 of FIG. 15. This flow cell 200 is shown diagrammatically in FIG. 23(b). As shown, the small portion of the cell suspension 192 is passed through the flow cell 200 and its cell density is measured, using conventional flow cytometry techniques. In one embodiment no cell density measurement is taken if, given experimental experience, the cell density turns out to be non-problematic, that is the cell collection step from the patient is generally successful in providing an adequate number of cells or the volume of reagents to number of cells ratio turns out to be non-critical to the process. In yet another embodiment, the cell density is measured directly while the cell suspension is within third chamber 144 by, for instance, light absorption, light scattering or electrical resistance or other techniques.

Next, the tip 126 of the second pipettor 122 is moved to its wash station 128 and washed. Wash station 128, except for its location and the choice of washing fluid, is identical to the first wash station 100.

Next, the staining processing is performed to stain the cervical cells by transferring the above-described fluorochrome-conjugated antibody cocktail (mixture) from the reagent pack into the cell suspension 192 in chamber 144. This transfer takes place using the second pipettor 122 and its associated pipettor tip 126. There then is an incubation period in chamber 144 (as described above) typically carried out at approximately 4° C. or other suitable temperature to incubate the cell suspension with the antibody mixture for a period of time, for instance 30 minutes, or otherwise as suitable as described above. Next, the second pipettor tip 126 is moved to its wash station 128 and washed. This completes the processing in the third chamber 144.

Next, as part of the preanalytical process the unbound antibodies from the antibody mixture are eliminated from the sample. First the sample is transferred to the fourth chamber 146 as shown in FIG. 24. This transfer is done by aspirating the sample 192 into fourth chamber 146 via the second pipettor 122 and its tip 126. As shown in FIG. 24, the central portion of the fourth chamber 146 is occupied by a small pore filter 160 having a pore size in the range of 5 to 20 μm. The filter can be made of a variety of materials, including different polymers such as nylon mesh, poretic polycarbonate films (such as those from Osmonic Inc.). Alternatively, rather than using a filter in the fourth chamber, the onboard centrifuge may perform this separation activity. Also, rather than providing a fourth chamber 146, this step could be performed in one of the other chambers.

Filter 160 separates the unbound fluorochrome conjugated antibodies from the stained cells by retaining the relatively larger stained cells 202 on the upper surface of the filter 160 and allowing the unbound antibodies to pass through the filter 160 under the influence of vacuum supplied at vacuum nozzle 162. This results in the unbound antibodies 206 passing into the lower portion of fourth chamber 146, while the stained cervical cells remain as a supernatant on the upper surface of filter 160. While the vacuum is on, one adds staining solution or PBS (phosphate buffered saline solution) to complete the elimination of the unbound conjugated antibodies and make sure they pass into the waste fluid 206. It may be that adding the PBS is not necessary if filtration is adequate for separation of the cells from the unbound antibodies. After the vacuum is turned off at nozzle 162, air is injected therethrough to close the fourth chamber 146.

At this point isotonic diluent 210 is added through second pipettor 122 to re-suspend the cervical cells, as shown in FIG. 25. The goal is to suspend all of the cervical cells, typically by multiple aspirations and dispensing of the diluent 210 in and out of the second pipettor 122 to fully dispense the cells. This completes the processing in the preanalytical unit 64.

At this point, the stained cervical cells in suspension 210 are aspirated through second pipettor tip 126 and transferred from the analytical unit 66. The cervical cells are then dispensed from pipettor 122 into the flow cell injector 220 (see FIG. 26). As an alternative the cells are transferred as monolayer of cells onto a glass side for cell imaging. The second pipettor tip 126 is then pivoted to its wash station 128 and washed. Then (see FIG. 18) the used reaction cartridge 116 is picked up by the robotic pick and place arm 112 and disposed into the disposal slot 108. Instead of using a robotic pick and place, the operator may transfer the reaction cartridges manually.

Further processing takes place in the analytical unit 66 shown in FIG. 26. The chief element of analytical unit 66 is flow cell 200. The analytical unit 66 further includes a supporting chassis 212. The second pipettor 122 is shown in FIG. 26, even though this pipettor 122 is also part of the preanalytical unit 66; it is shared by both the preanalytical unit and the analytical unit for sample transfers.

Other elements shown in the analytical unit 66 in FIG. 26 are the flow cell injector 220 and the associated tubing 224 carrying the sample into the flow cell 200. Generally, the flow cell 200 is conventional, of the type known in the field, and further details of its construction are not provided here as being well known. A suitable flow cell is available from Becton Dickinson Biosciences. The flow cell 200 includes sample feed nozzle 226, stream sheath 228 (shown in cross section), and a first laser 232 (light source) which is for instance a solid state 488 nanometer (nm) wavelength laser as described above outputting a laser beam 234 which, after passing through the sample stream, has beam portions incident on a set of optical detectors 236, 240 and 242. The various light detectors include conventional photodetectors and photomultipliers to measure incident optical signals and convert them to electronic signals. Each of these detectors is a different type of optical detector. For instance, in one embodiment (see above) the first detector or detectors 236 are for measurement of fluorescence in the FITC or PE or PerCP bands, as described above. The second detector 240, is for instance, a 488 nanometer wavelength forward scattering detector. The third detector 242 is, for instance, a 488 nanometer wavelength side scattering detector. The optical detector arrangement shown here is illustrative, as are the types of detectors.

Also provided is a second laser 250, in this example a HeNe 633 nanometer wavelength red or near infra-red (NIR) laser outputting a laser beam 252 which after passing through the sample in the flow cell 200 is incident upon optical detectors 258, 260 and 262. Detector 258 may be multiple detectors. The first detector(s) 258 is for instance a fluorescence APC detector. The second detector 260 is, for instance, an NIR forward scattering detector. The third detector 262 is, for instance, an NIR side scattering detector. Other types of detectors and detector arrangements are possible. For instance there is no requirement that there be two lasers (or other light source) each with its own set of detectors; for some antibodies perhaps only a single laser or other light source is used, or there may be additional lasers.

The second pipettor 122 as stated above transfers the sample cells into the flow cell injector 220. Flow cell injector 220 passes the sample cells via the sample feed nozzle 226 from connecting tubing 224 into the flow cell 200. Typically the cells are passed at high speed, e.g., several thousand cells per second, as typical of flow cell cytometry. FIG. 26 shows how this effectively allows a single cell at a time to pass through the lower portion of the flow cell 200 so that each cell is individually subject to incident laser beams 234, 252 and the laser beams are subsequently subject to detection by the associated optical detectors. As shown in FIG. 26 at this point there are two types of cells in the sample, the ordinary cervical cells and (possibly) the precancerous or cancerous (cancer) cells shown by the enlarged nucleus. The goal of course is to detect any precancerous or cancerous cells. However, that is not limiting and this apparatus can be used to detect other than cervical cancer cells, including other types of cancer and also may be used for other types of cell detection, not limited to cancer screening.

The processing of the cells and the resulting data collection is as described above. In one embodiment, detector 240 can measure the forward scattering excited by laser beam 234 to provide data to eliminate non-cervical cells and debris particles from the data analysis. Alternatively, other laser sources may be used here. The side scattering detector 242, for instance, provides data that enables classification of various cervical cell types as described above. Information on cell morphology and potentially the nucleus/cytoplasm size ratio (described above) is an important measurement factor. The florescence detector or detectors 236 measure cell auto-florescence, which enables elimination of auto-florescence in other related bands or as a gating parameter as described above. In addition, the detected auto-florescence may be used to determine the presence of a precancerous or cancerous cell. Other laser sources or fluorescence microscopic imaging may be used here.

In one embodiment, the fluorescence detector or detectors 236 can also measure the presence of the antibody P16INK4a as described above. In one embodiment this is the most important determinant of normal vs. precancerous or cancerous cells.

The second laser 250 and its laser beam 252 are also used as described above. For instance, fluorescence intensity detected by detector 258 is a proliferation marker Mcm5 as a complementary marker to differentiate between normal and precancerous or cancerous cells. Different or additional proliferation markers may be used, for instance, Cdc6, and other types of laser sources may be used. The near infrared forward scattering detector allows estimation of the size of the nucleus of the cells which may provide a key parameter to calculate the cytoplasm/nucleus size ratio as described above. This determination also involves both the forward scattering detector 260 and the side scattering detector 262.

The remaining processing is largely conventional in terms of the data handling and is as described above. The data is acquired from the optical detectors 236, 240, 242, 258, 260 and 262 and, for instance, real time digital signal processing (DSP) circuitry processes the resulting data. Typically multivarious analysis algorithms, gating parameters, threshold values and classifications are applied to the resulting data in the computer system CPU 54. The raw and unprocessed data is typically stored in the CPU 54 memory and is accessible for presentation or further analysis, including a report for each sample of presence of precancerous or cancerous cells or not.

FIGS. 27(*a*)-27(*c*) show graphically individual cell size measurements to analyze cell morphology, e.g., the ratio of the size of a cell nucleus 272 and to the overall size of the cell 270 as described above. For instance, in FIG. 27(*a*) the width a and height b of the cell 270 are measured. In another measurement in FIG. 27(*b*), the width c and height d of the cell nucleus 272 are measured. In FIG. 27(*c*) the ratio of the size of the cytoplasm (the cell less the nucleus) is compared to the size of the nucleus. This ratio is in accordance with the above described method and provides an indication of cell morphology to identify an abnormal (precancerous or cancerous) cell.

A cell sorter may be included in the analytical unit. The cell sorter is a conventional flow-cytometer component that is built-in to the flow cell. The cell sorter is capable of physically sorting cells. The analysis of the cells is done extremely fast so that the result for each cell is available before the cell exits the flow cell. The criteria for cell sorting is set by the data processing algorithms. For example, the criteria is normal cells vs. dysplastic cells. The cell sorter then physically separates the dysplastic cells into a small container. These cells could then be put onto a slide and reviewed under the microscope by the pathologist. This has the advantage that the pathologist would only see the cells classified as dysplastic by the apparatus.

After passing through the flow cell 200, the sample is disposed of by the analytical unit. Of course, only part of the overall sample has been subject to the pre-analytical and analytical units and the remainder of the sample still remains in the original sample vial and that vial is transferred conventionally into the post-analytical sample management unit 70 shown in FIG. 15. At this point the apparatus is no longer used to process the sample remainder, but the sample remainder may be subject to a conventional manual examination by a cytotechnologist or a pathologist to confirm any findings by the apparatus as described above.

The pathologist normally confirms or reflex tests the "positive" samples. If using the residual sample from the sample vial, these samples still have all the obscuring factors included. The pathologist (would thus not be able to review these residual samples including the obscuring factors, under the microscope. Therefore it is necessary to remove the obscuring factors. One way to do that is using the pre-analytical unit of the apparatus. Therefore the operator has the option to re-run the sample remainder after the initial analysis is complete and the sample vial is likely still in the sample loader. The operator then initiates the re-run using the patient identification and runs it as a normal sample on the apparatus. The sample vials on the sample loader are scanned by the barcode scanner until the sample that is to be re-run is found. This sample is then processed exactly as the first time all the way to the third chamber and before the reagent (antibodies) is added. At that time the second pipettor transfers the re-suspended "clean" cells to a clean-cell station (physically located beside the second pipettor but not illustrated here) and at that location dispenses them directly onto a glass slide or alternatively into a small vial. From there the cytotechnologist can take the slide and hand it directly over to the pathologist or prepare a slide using the cell solution in the small vial. In both cases the cytotechnologist first stains the cells with the typical PAP stain.

Other functions carried out by the computer system 52, 54, 56 of the FIG. 15 apparatus are largely conventional and of the type carried out by other types of automated instrumentation and medical testing equipment. For instance, the keyboard 52 and any other operator input interface such as a computer mouse and display 56 serve as a communication platform between the operator and the apparatus. Work list management is carried out by software executed by the CPU 54 which allows a downloaded or entered list of active work orders to be processed. The result reporting of the testing samples is provided on the display 56 and/or printed out by an associated printer with the data analyzed in numeric and histogram format which can be presented on the display or printed, as is conventional in medical instrumentation. The data transfer is typically carried out by the LIS interface so that work orders can be down and uploaded and results uploaded to the LIS interface. Work lists, consisting of individual patient work orders can be downloaded from the LIS to the computer system of the apparatus using the LIS interface. The patient results including numeric data and histograms can be uploaded to the LIS from the computer of the apparatus using the LIS interface.

Patient report creation is carried out by software of conventional type operating on the CPU 54 so that the operator can generate a customized patient result report and print same.

CPU 54 also carries out, through appropriate software, calibration of functions such as alignment of the lasers and calibration of the pipettors and the robotic components so that they are operating properly. Also provided are calibrators and associated software which calibrate the data processing gate parameters and algorithms. Calibrators are artificially prepared samples with pre-determined and exact concentrations of single or multiple components (e.g., fluorescence pre-labeled or unlabeled microbeads, a solution that contains 100,000 normal cervical cells and 200 p16INK4a positive dysplastic cells). These pre-prepared calibrators are used by the operator to calibrate the apparatus. The data processing algorithms are adjusted according to these calibrators. Controls are provided which are basically the same as calibrators but they check the performance of the apparatus (e.g., the apparatus is calibrated at concentrations of 200 and 1,000 p16INK4a positive cells). The algorithms are adjusted according to the calibrators and controls. In order to check the apparatus, a control containing 500 p16INK4a positive cells is run on the apparatus exactly in the same mode as a patient sample to verify if the system actually reads 500 cells. Also provided is software to handle testing of method controls which are samples, but not from the patient, of known type, for instance standardized precancerous or cancerous samples, which are used to check performance of the apparatus, as is conventional in the field. Also provided is software for instrument maintenance which is both automated and operator guided, for instance for daily or weekly maintenance. Also provided is a security feature to control operator access via software. The operator manual and training are also provided in software form, for instance, including interactive onboard training programs, Q and A, and operator manuals. Also included is software for administrative purposes including billing and inventory management of supplies such as the reaction cartridges and reagent kits.

EXAMPLES

The following examples are given for the purpose of illustration only and are not intended to limit the scope of the methods and devices as disclosed herein. Examples 1 through 3 provide microscopic imaging-based experiments on cells or cervical samples. The sample preparation and staining protocols used in those experiments were designed with flow cytometry in mind and are different from the standard slide-based immunofluorescence imaging protocols. Examples 4 through 7 provide flow cytometry-based experiments on cervical cell samples.

Example 1

Microscopic Imaging of the Cervical Cancer Cell Lines Stained with a Cocktail of PE-p16INK4a and APC-Mcm5 Antibodies In this experiment, two cervical cancer cell lines HeLa (HPV18 positive) and Ca Ski (HPV16 positive) were stained by both an isotype and an antibody to compare their staining intensity. These two cell lines are good positive controls to test the effectiveness of the antibody staining. Two mouse monoclonal antibodies for p16INK4a (clone ZJ11) and for Mcm5 (clone CRCT5.1) were used. The p16INK4a antibody and corresponding IgG1 isotype were conjugated with PE fluorochrome to form a PE-p16INK4a antibody and a PE-IgG1 isotype. The Mcm5 antibody and corresponding IgG2b isotype were conjugated with APC fluorochrome to form an APC-Mcm5 antibody and an APC-IgG2b isotype.

HeLa cells and CaSki cells were fixed and permeabilized with a methanol-based solution. Before staining, the cells were washed with a staining buffer twice. Then the PE-p16INK4a and APC-Mcm5 antibodies were added to the HeLa cells simultaneously (both have the staining concentration of about 0.1 µg/10⁶-cell). The same amount of PE-IgG1 and APC-IgG2b isotypes were used to stain the same number of control cells in a separate experiment. The above staining procedures were repeated for Ca Ski cells.

Stained cells were transferred onto slides for fluorescence imaging. Four images were obtained from each cell in a field-of-view. Three fluorescence images of FITC, PE, and APC bands and one DIC image were obtained for each cell. A MATLAB program written for the multi-color image processing and analysis was used to estimate the average fluorescence intensity of each cell. The mean and standard deviation of the average fluorescence intensity of all the imaged cells are also listed in Table 1.

TABLE 1

HeLa and Ca Ski Cells Stained with a 0.1 µg per 10⁶-cell Antibodies and Isotypes Cocktail

| Specimens | FITC band Intensity | PE band Intensity | APC band Intensity |
|---|---|---|---|
| HeLa Cells Stained with PE-IgG1 + APC-IgG2b | 64.1 ± 27.1 (n* = 40) | 54.3 ± 12.9 (n = 40) | 52.7 ± 19.3 (n = 40) |
| HeLa Cells Stained with PE-p16INK4a + APC-Mcm5 | 77.9 ± 40.7 (n = 45) | 141.0 ± 40.0 (n = 45) | 335.7 ± 125.8 (n = 45) |
| Ca Ski Cells Stained with PE-IgG1 + APC-IgG2b | 58.1 ± 7.7 (n = 46) | 76.6 ± 21.1 (n = 46) | 85.6 ± 27.3 (n = 46) |
| Ca Ski Cells Stained with PE-p16INK4a + APC-Mcm5 | 61.3 ± 8.7 (n = 69) | 143.6 ± 36.5 (n = 69) | 429.5 ± 142.7 (n = 69) |

*n is the number of cells measured.

Figure 3:
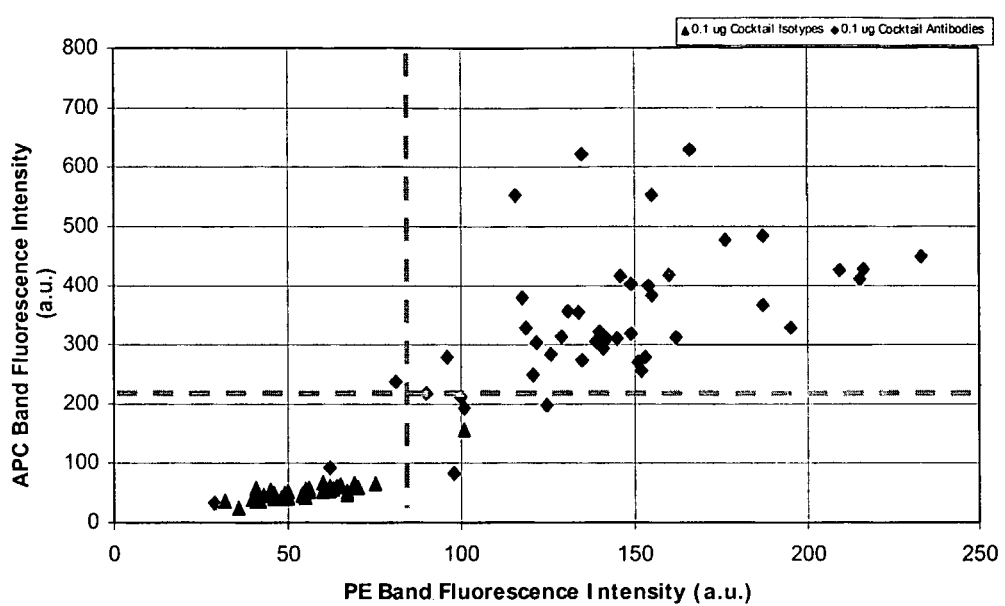
FIG. 3 shows a dot plot of PE (phycoerythrin) and APC (allophycocyanin) fluorescence intensities for HeLa cells stained with an antibody cocktail (0.1 µg per $10^6$ cells) containing PE-p16INK4a and APC-Mcm5 antibodies (shown in diamonds) or isotype antibodies (shown in triangles) and analyzed under a microscope. The x axis represents PE band fluorescence intensity (arbitrary unit). The y axis represents APC band fluorescence intensity (arbitrary unit).
Figure 4:
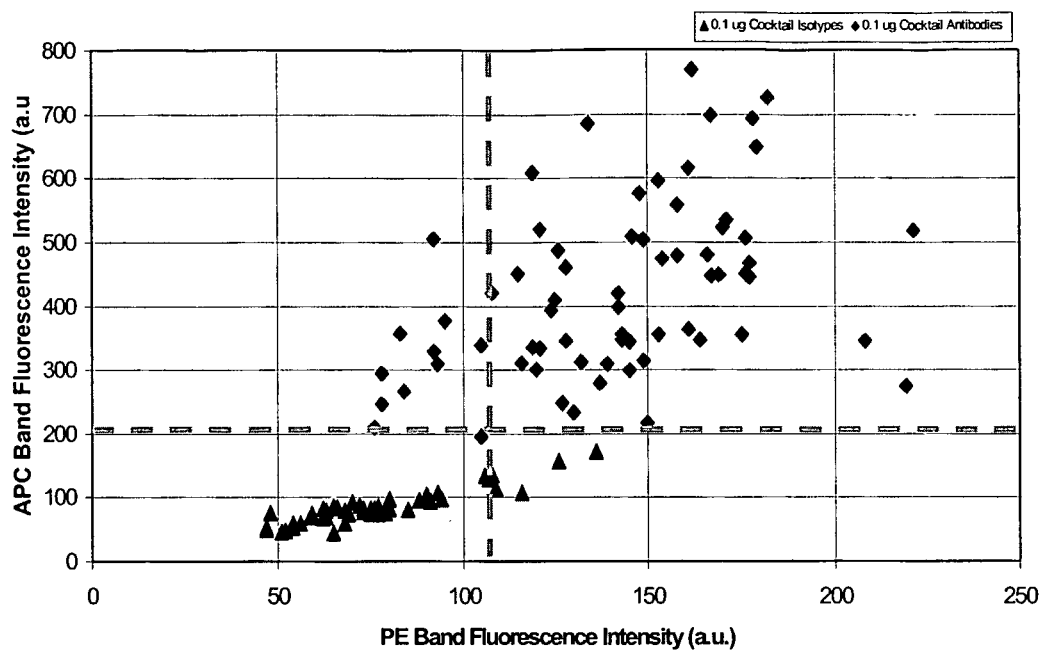
FIG. 4 shows a dot plot of PE and APC fluorescence intensities for CaSki cells stained with an antibody cocktail (0.1 µg per $10^6$ cells) containing PE-p16INK4a and APC-Mcm5 antibodies (shown in diamonds) or isotype antibodies (shown in triangles) and analyzed under a microscope. The x axis represents PE band fluorescence intensity (arbitrary unit). The y axis represents APC band fluorescence intensity (arbitrary unit).

As shown in Table 1, the antibody-stained cells had significantly higher intensities in both PE and APC bands, than that of the isotype-stained cells for both HeLa and Ca Ski cells. This result suggested that both biomarkers p16INK4a and Mcm5 are overexpressed in HPV18 and HPV16 positive cells. The dot plots in FIGS. 3 and 4 show the PE versus APC band fluorescence intensity of each cell (i.e., the staining intensities of the p16INK4a antibody versus the Mcm5 antibody for each detected cell in the HeLa and CaSki cell lines). The staining intensities of the p16INK4a antibody and Mcm5 antibody are not exactly linearly related across different cells. This suggests that the two antibodies play complementary roles.

Example 2

Microscopic Imaging of Negative and HSIL Cervical Specimens Stained with a Cocktail of PE-p16INK4a and APC-Mcm5 Antibodies A negative cervical specimen S7188 and a HSIL cervical specimen S7184 were stained with a cocktail of antibodies and isotypes, respectively. The negative and HSIL classifications of these two specimens were determined by experienced cytopathologists. The antibodies used herein for p16INK4a and Mcm5 proteins were the same as those used in Example 1. The p16INK4a antibody was conjugated with PE fluorochrome. The Mcm5 antibody was conjugated with APC fluorochrome. In the experiment, 8 µg/million-cell concentration of PE-p16INK4a and 8 ug/million-cell concentration of APC-Mcm5 were added to the samples simultaneously. The staining process lasted 30 minutes at 4° C. Then the samples were washed to remove unbound antibodies. The same concentration of PE-IgG1 and APC-IgG2b isotypes were also used to stain the samples.

The samples were transferred to the slides and imaged. Table 2 compares the average fluorescence intensities between the isotype-stained samples and the antibody-stained samples. The results clearly show that the isotype-stained samples have significant lower fluorescence intensities in the PE and APC bands than that of the antibody-stained samples, especially relative to the antibody-stained HSIL samples. The PE and APC bands fluorescence intensities of the isotype-stained samples indicate the non-specific binding of the antibodies to the cells. The data shows that the non-specific bindings of negative and HSIL specimens are similar.

In the FITC band, the isotype-stained samples have similar intensities than that of the antibody-stained samples. This is because the fluorescence intensity in this band is generated by the cell's autofluorescence. The autofluorescence intensity in the negative specimen is lower than that in the HSIL specimen.

In the PE band, the results show that the HSIL specimen has a higher average expression of p16INK4a proteins in cells than that of the negative specimen. However, in the APC band, the HSIL specimen has only a slightly higher average expression of Mcm5 proteins than that in the negative specimen.

Figure 5:
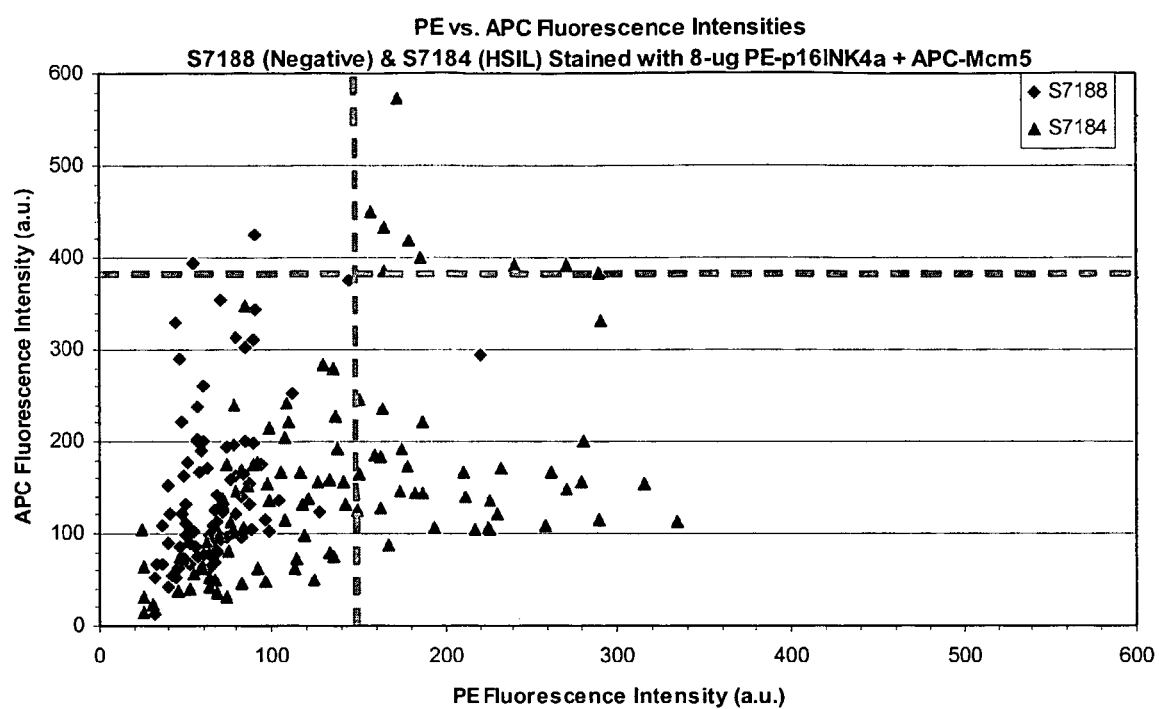
FIG. 5 shows a dot plot of PE and APC fluorescence intensities for S7188 (negative, shown as diamonds) and S7184 (HSIL, shown as triangles) cells stained with an antibody cocktail (8 µg) containing PE-p16INK4a and APC-Mcm5 antibodies and analyzed under a microscope. The x axis represents PE band fluorescence intensity (arbitrary unit). The y axis represents APC band fluorescence intensity (arbitrary unit).

FIG. 5 uses a dot plot to illustrate the staining intensity of PE and APC of each cell in the negative and HSIL samples. This plot clearly shows the percentage of cells that express high p16INK4a and Mcm5 proteins. Many of the cells in the HSIL specimen have a higher expression of p16INK4a proteins or have both a higher expression of p16INK4a and Mcm5 proteins than the negative specimens. The number of cells that have a high expression of p16INK4a and Mcm5 proteins can be used to differentiate a negative cervical specimen and a positive cervical specimen.

TABLE 2

Cervical Specimens Stained with 8 µg per 10⁶-cell of Antibody and Isotype

| Specimens | FITC band Intensity | PE band Intensity | APC band Intensity |
|---|---|---|---|
| S7188 Stained with Isotype | 115.4 ± 29.5 (n = 47) | 31.9 ± 9.0 (n = 47) | 26.9 ± 8.6 (n = 47) |
| S7184 Stained with Isotype | 141.7 ± 55.0 (n = 52) | 25.5 ± 9.6 (n = 52) | 25.8 ± 9.2 (n = 52) |
| S7188 Stained with Antibody | 121.8 ± 39.3 (n = 84) | 67.9 ± 27.0 (n = 84) | 150.8 ± 89.8 (n = 84) |
| S7184 Stained with Antibody | 144.0 ± 50.4 (n = 102) | 138.3 ± 74.0 (n = 102) | 158.9 ± 107.0 (n = 102) |

Experiment 3

Microscopic Imaging of Negative, ASCUS, LSIL, and HSIL Cervical specimens Stained with a Cocktail of PE-p16INK4a and APC-Mcm5 Antibodies In this experiment, we stained eleven cervical specimens using the p16INK4a-Mcm5 cocktail antibody. The eleven specimens included five negatives, one ASCUS, two LSIL, and three HSIL specimens.

Each specimen was divided into two parts. One part was unstained and used to establish autofluorescence compensation coefficients. Another part was stained with the cocktail of PE-p16INK4a and APC-Mcm5 antibodies. The stained cells were transferred to a slide for imaging. About 70 cells, including cells with different shapes, were imaged for each specimen. The average fluorescence intensities were computed for each cell imaged. FIGS. 6(a)-(d) give an example of the DIC and fluorescence images of a normal and a precancerous or cancerous HSIL cell in a HSIL cervical specimen. The average PE and APC intensities of the HSIL cell are significantly higher than that of the normal cells.

Most cells in the eleven specimens had low stain intensities in both PE and APC bands. There were a small number of cells, however, that either had a high stain intensity in PE, APC, or in both bands. These highly stained cells were mostly present in the ASCUS, LSIL, and HSIL specimens. In this experiment, we assume that if two cells (out of an average of 70 cells) are detected as precancerous or cancerous cells with high stain intensity in PE/APC bands, then the specimen is classified as "positive" (using two precancerous or cancerous cells instead of one for classification was considered more dependable).

Figure 2:
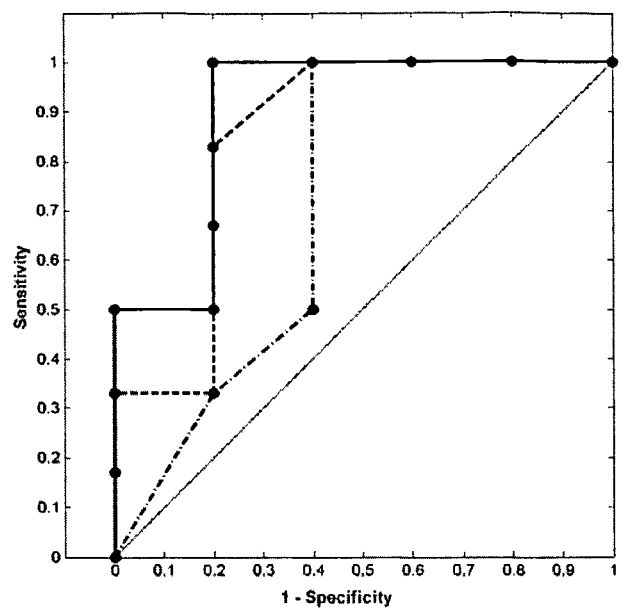
FIG. 2 shows ROC curves of discrimination on "negative" and "positive" cervical samples using Mcm5 marker only (dotted dash lines), p16INK4a only (dash lines), and both markers (solid lines). The x axis represents 1-specificity, the y axis represents sensitivity.

The discrimination power in this experiment is evaluated by using a ROC curve. FIG. 2 illustrates three ROC curves, which indicate the performance when using individual p16INK4a or Mcm5 markers and when using a combination. Although the ROC curves are very discrete due to the small number of samples, they suggest that the combination of the markers has a better performance than either individual marker. The p16INK4a marker appears to be better than the Mcm5. The areas under the ROC curves are 0.9, 0.85, and 0.72 for the combination of markers, the p16INK4a marker alone, and the Mcm5 marker alone, respectively. Mcm5 is a marker for cell proliferation. Negative but inflammatory specimens often contain proliferation cells with a high Mcm5 stain. Therefore, the Mcm5 marker has less power than the p16INK4a marker in discriminating negative and positive specimens. However, for the HSIL cells, both p16INK4a and Mcm5 markers are very highly expressed. This suggests that whether a cell is p16INK4a positive, Mcm5 positive, or both positive is related to the abnormality of the cell.

From our rough ROC curve, the combination of the markers can achieve a sensitivity of 1 with a specificity of 0.8. In this case, one negative specimen was mistakenly reported to be "positive". Such false positives would be referred to cytopathologists for further confirmation.

This experiment showed the expression of both p16INK4a and Mcm5 markers in cervical cells. It also showed the promise of using these two markers to differentiate between "negative" and "positive" cervical specimens.

Example 4

Flow Cytometry Measurement of the Cervical Cancer Cell Lines Stained with a Cocktail of PE-p16INK4a and APC-Mcm5 Antibodies In this experiment, cervical cancer cell line Hela, known to be HPV18 positive with high expression of both p16INK4a and Mcm5, was used to shown immunofluorescence detection by flow cytometry. Hela cells were divided into two samples, one was unstained, and the other was stained by a cocktail of PE-p16INK4a and APC-Mcm5 antibodies. The sample preparation and immunofluorescence staining of these two specimens followed the procedures described above. The concentration of the two antibodies used in the experiment was 0.5 μg per $10^6$ cells (suspended in one milliliter staining buffer).

Flow cytometry measurement was performed on two samples. Five parameters including forward light scattering (FSC), side light scattering (SSC), FITC, PE, and APC were measured by the flow cytometer. The flow cytometer was first calibrated with CaliBRIGHT beads (BD Bioscience). The COMP-beads (BD Bioscience) stained with the same antibodies used for cells, were then measured to determine the compensation ratios among the fluorescence bands. After calibration, the unstained samples were measured to estimate the cell autofluorescence in the FITC, PE, and APC bands. In the following analysis, the autofluorescence and spillover fluorescence intensities were subtracted from the total fluorescence intensities of each cell to obtain the immunofluorescence intensity in the PE and APC bands.

Figure 7:
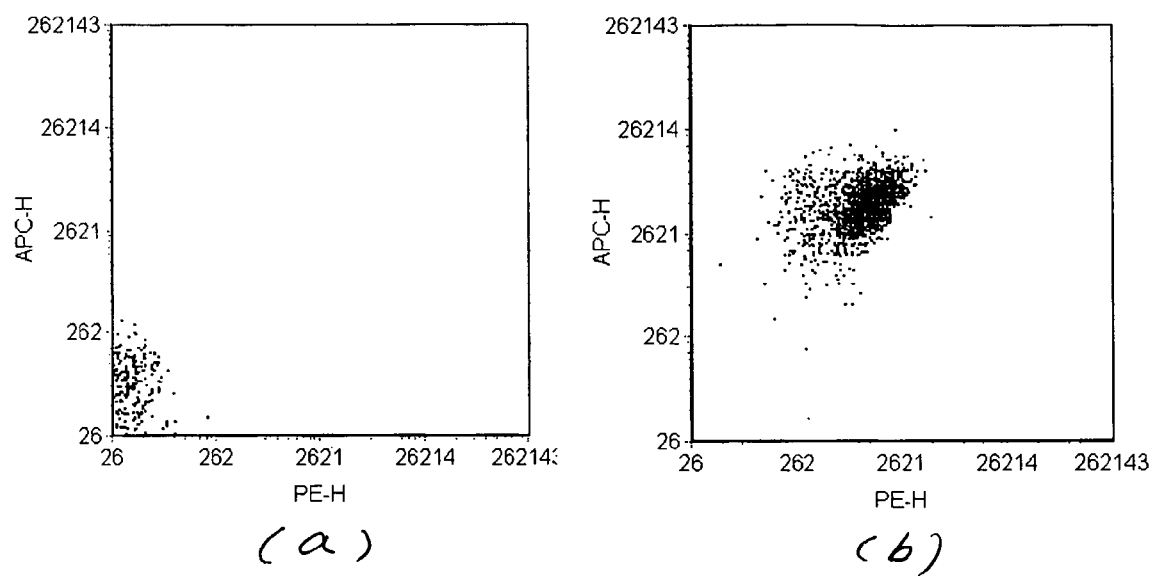
FIGS. 7(a) and 7(b) show dot plots of PE versus APC immunofluorescence intensities of unstained Hela cells (7(a)) and Hela cells stained with PE-p16INK4a and APC-Mcm5 antibodies (7(b)). The cells were analyzed by flow cytometry. The average intensities of PE and APC for unstained Hela cells are 19.8 and 38.2 (arbitrary unit), respectively. The average intensities of PE and APC for antibody-stained Hela cells are 1295.9 and 5537.5 (arbitrary unit), respectively. The x axis represents PE band fluorescence intensity (arbitrary unit). The y axis represents APC band fluorescence intensity (arbitrary unit).

The dot plots in FIGS. 7(a) and 7(b) illustrate the PE versus APC immunofluorescence intensities of the cells in the unstained Hela cells (left) and the antibody-stained Hela cells (right). Non-cell debris has been excluded from the plots using a FSC and SSC gating (not shown in the plots). These two plots clearly show the contrast of intensity distribution between unstained and antibody stained Hela cells.

Example 5

Flow Cytometry Measurement of a Negative and an HSIL Cervical Specimen Stained with a Cocktail of PE-p16INK4a and APC-Mcm5 Antibodies In this experiment, two cervical specimens (S7338 and S7314) were measured with a flow cytometer. Each specimen was divided into two tubes. One was unstained and the other was stained with a cocktail of PE-p16INK4a and APC-Mcm5 antibodies. The sample preparation and immunofluorescence staining of these specimens followed the same procedures described above. The concentration of the two antibodies used in the experiment was 0.25 μg per $10^6$ cells (suspended in one milliliter staining buffer).

Five parameters including forward light scattering (FSC), side light scattering (SSC), FITC, PE, and APC were measured by the flow cytometer. The flow cytometer was first calibrated with CaliBRIGHT beads (BD Bioscience). The COMP-beads (BD Bioscience) stained with the same antibodies used for cells, were then measured to determine the compensation ratios among the fluorescence bands. After calibration, the unstained samples were measured to estimate the cell autofluorescence in the FITC, PE, and APC bands. In the following analysis, the autofluorescence and spillover fluorescence intensities were subtracted from the total fluorescence intensities of each cell to obtain the immunofluorescence intensity in the PE and APC bands.

Figure 8:
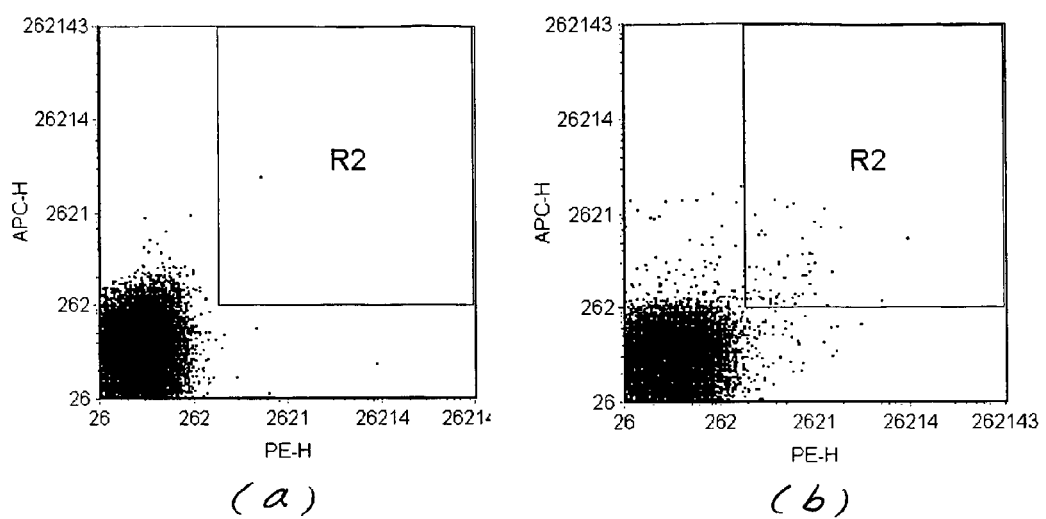
FIGS. 8(a) and 8(b) show dot plots of PE versus APC immunofluorescence intensities of cells in the cervical specimen S7338 (negative, 8(a)) and S7314 (HSIL, 8(b)). The cells were stained with PE-p16INK4a and APC-Mcm5 antibodies and analyzed by flow cytometry. About 50,000 cells were included in each plot. The x axis represents PE band fluorescence intensity (arbitrary unit). The y axis represents APC band fluorescence intensity (arbitrary unit).
Figure 9:
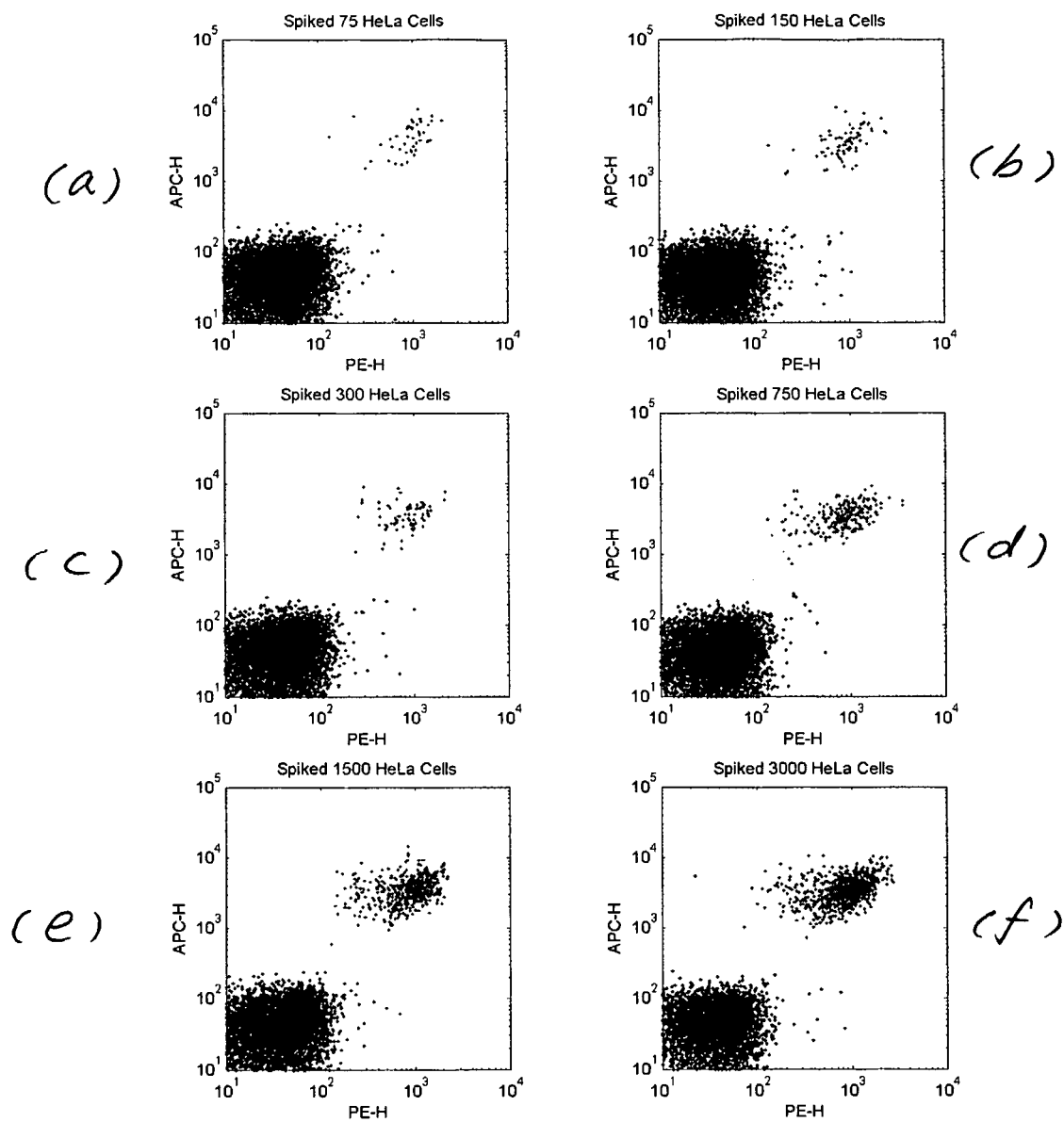
FIGS. 9(a)-9(f) show dot plots of PE versus APC immunofluorescence intensities of unstained cervical specimen spiked with Hela cells that were stained with PE-p16INK4a and APC-Mcm5 antibodies. The cells were analyzed by flow cytometry. Approximately 75 (9(a)), 150 (9(b)), 300 (9(c)), 750 (9(d)), 1500(9(e)), and 3000 (9(f)) Hela cells were added into about 100,000 cervical cells. The x axis represents PE band fluorescence intensity (arbitrary unit). The y axis represents APC band fluorescence intensity (arbitrary unit).

The dot plots in FIGS. 8(a) and 8(b) illustrate the PE versus APC immunofluorescence intensities of the cells in the antibody-stained cervical specimens S7338 (left) and S7314 (right). Non-cell debris has been excluded from the plots by using a FSC and SSC gating (not shown in the plots). About 50,000 cells were included in each plot. In the R2 region where both PE and APC have high intensity, there are only three cells for the negative specimen S7338. In contrast, there are 77 cells for the HSIL specimen S7314. This clearly shows that there were more dysplastic cells in the HSIL specimen than in the negative specimen.

Example 6

Flow Cytometry Measurement of an Unstained Negative Cervical Specimen Spiked with Antibody-Stained Hela Cells This experiment shows the sensitivity and accuracy of detection using a flow cytometer.

In this experiment, HeLa cells were stained by a cocktail of PE-p16INK4a and APC-Mcm5 antibodies. The concentration of both antibodies was 0.5 μg/$10^6$ cell (in milliliter volume). After staining, the cell density was estimated using a hemocytometer. The HeLa sample, with known cell density, was then diluted to different concentrations. An appropriate volume, with the number of HeLa cells being approximately 75, 150, 300, 750, 1500, or 3000, was taken from the different concentrations of HeLa samples and added to six tubes containing unstained negative cervical specimen S7339. Each tube contained about 100,000 S7339 cells.

The mixed samples were then measured by a flow cytometer. The spiked HeLa cells were identified from the mixture based on the antibody staining intensity and were counted.

FIGS. 9(a)-9(f) illustrate the PE versus APC band staining intensities of all the cells in the six tubes. The highly stained HeLa cells are on the upper-right corner, while the unstained cervical cells are on the bottom-left corner.

Figure 10:
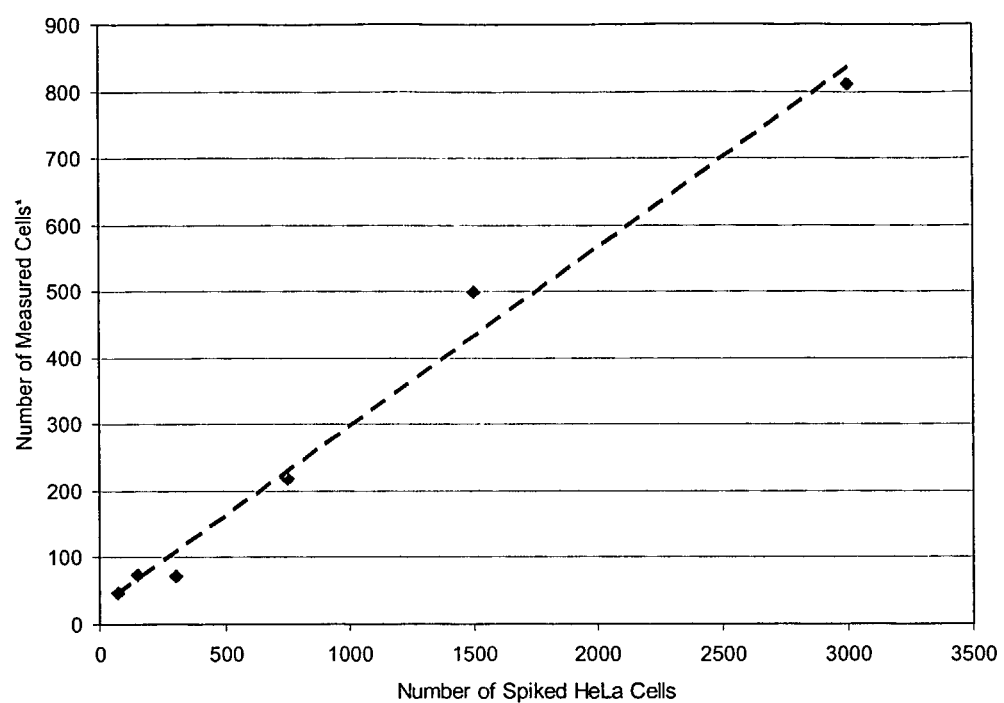
FIG. 10 shows the linear relationship between the spiked Hela cells and the measured Hela cells in the spiking experiment. The x axis represents the number of spiked Hela cells. The y axis represents the number of measured Hela cells.

The number of HeLa cells measured using flow cytometry was compared with the number of spiked HeLa cells. The relationship is shown in FIG. 10. The measured number of HeLa cells is linearly related to the number of HeLa cells added to the mixture. This linear relationship shows the accuracy of flow measurement.

The minimum number of spiked HeLa cells was 75. The corresponding measurement of the HeLa cells was 45. This indicates that the flow cytometer is able to detect a positive cervical specimen with as few as 100 precancerous or cancerous cells out of about 100,000 cells (a 0.1% rare event). This shows that the measurement used in the present experiment is very sensitive.

Example 7

Flow Cytometry Analysis of Negative, ASCUS, LSIL, and HSIL Specimens Stained with a Cocktail of PE-p16INK4a and APC-Mcm5 Antibodies In this experiment, twelve cervical specimens were studied. They included five negative, two ASCUS, one LSIL, and four HSIL specimens that were pre-classified with Pap tests by experienced cytopathologists.

Each specimen was split into two aliquots. One aliquot was unstained and used to measure the cell autofluorescence in the three fluorescence bands—FITC, PE, and APC. The other aliquot was stained with a cocktail of PE conjugated p16$^{INK4a}$ and APC conjugated Mcm5 antibodies. The same five-parameter flow cytometry measurement and similar data analysis procedures described previously were performed for each sample.

FIGS. 11(a) and 11(b) compare the PE versus APC dot plots between a negative (left) and a HSIL (right) cervical specimen. These two plots clearly show that the HSIL specimen has significantly more cells with high intensities in both PE and APC bands than the negative specimen. The high intensity in the PE and APC bands indicates that both biomarkers p16INK4a and Mcm5 are overexpressed.

The detection threshold to separate "negative' from "positive" specimens were set arbitrarily in this experiment. In Table 3, the classification of the twelve specimens determined by multi-parameter flow cytometry is compared with the classification by the Pap tests. Using Pap tests as the reference, the sensitivity and specificity of the flow cytometry methods for cervical cancer screening are 100% and 80%, respectively. Although the results were based on the test of a small number of specimens, this experiment demonstrated the promise of using multi-parameter flow cytometry for cervical cancer screening. The detection threshold used in this proof-of-concept study, however, will be further adjusted based on the results from a large-scale clinical study to be performed upon the development of prototype instruments. By then, the reference method of choice will be biopsy, the current gold standard. The definition the detection threshold will also consider the trade-off between the sensitivity and specificity of the screening.

TABLE 3

Comparison of the classification of the twelve specimens between flow cytometry and Pap tests

|  | Positive in Pap test | Negative in Pap test |  |
| --- | --- | --- | --- |
| Positive in flow cytometry | TP = 7 | FP = 1 | Specificiy = TN/ (TN + FP) = 80% |
| Negative in flow cytometry | FN = 0 | TN = 4 | Sensitivity = TP/ (TP + FN) = 100% |

Although the foregoing invention has been described in some detail by way of illustration and example for purpose of clarity and understanding, it will be apparent to those skilled in the art that certain changes and modifications will be practiced. Therefore, the description and examples should not be construed as limiting the scope of the invention, which is delineated by the appended claims.

We claim:

1. A method of determining the presence of a cervical abnormality in cells of a cervical sample, said sample including cell debris that contains non-cellular materials including parts of cells independent of an intact cell, fibrous but non-cellular tissues, dusts, contaminants, or pieces of any collector used to collect the cervical cell sample, comprising:

a) multiparametrically measuring a fluorescent signal emitted from a cervical sample contacted with at least one fluorescently labelled probing agent that specifically binds at least one biomarker specifically indicative of the cervical cell abnormality using flow cytometry, wherein said parameters comprise at least one numerical value of the signal attributed to at least one fluorescent activity produced by the at least one fluorescently labelled probing agent bound to said at least one biomarker if said at least one biomarker is present in said sample and by autofluorescence of said sample, wherein the at least one fluorescently labeled probe is differently labeled from another fluorescently labeled probe bound to another distinct biomarker; and a reference numerical value of the signal attributed to at least one fluorescent activity produced by autofluorescence of said sample;

b) calibrating the at least one numerical value by subtracting the reference numerical value from the at least one numerical value to produce at least one calibrated numerical value attributed to the fluorescent activity produced by said at least one fluorescently labelled probing agent bound to said at least one biomarker; and c) determining whether the cervical sample is positive or negative for the presence of the cervical cell abnormality by comparing the at least one calibrated numerical value to a predetermined threshold value, such that if the calibrated numerical value is at or above the threshold value the calibrated numerical value is indicative of the presence of the cervical cell abnormality or if the calibrated numerical value is below the threshold value the calibrated numerical value is indicative of the absence of the cervical cell abnormality.

2. The method according to claim 1, wherein the at least one of the probing agents recognizes p16INK4a.

3. The method according to claim 1, wherein the at least one of the probing agents recognizes a biomarker selected from the group consisting of: minichromosome maintenance complex component 5 (Mcm5), cell division cycle 6 (Cdc6), proliferating cell nuclear antigen (PCNA), Ki-67, epidermal growth factor receptor (EGFR), minichromosome maintenance complex component 2 (Mcm2), cyclin E, cyclin-kinase inhibitor WAF1 (CKI WAF1), cyclin-kinase inhibitor KIP1 (CKI KIP1), or telomerase.

4. The method according to claim 1, wherein the multiple parameters comprise at least two numerical values attributed to fluorescent activities produced by at least two fluorescently labelled probing agents, each labelled probing agents recognizing a different biomarker.

5. The method according to claim 4, wherein one of the probing agents recognizes p16INK4a and another one of the probing agents recognizes Mcm5.

6. The method according to claim 5, wherein the probing agent specifically recognizing p16INK4a is an anti-p16INK4a antibody and the probing agent specifically recognizing Mcm5 is an anti-Mcm5 antibody.

7. The method of claim 1 wherein said determining the presence of at least one biomarker specific to the cervical cell abnormality comprises determining the presence or absence of precancerous or cancerous cells.

8. The method according to claim 1, wherein said fluorescently labelled probing agent is labeled with quantum dots.

* * * * *